US008101192B2

(12) United States Patent
Lewinsohn et al.

(10) Patent No.: US 8,101,192 B2
(45) Date of Patent: Jan. 24, 2012

(54) METHODS FOR PRODUCING AN IMMUNE RESPONSE TO TUBERCULOSIS

(75) Inventors: David Lewinsohn, Portland, OR (US); Deborah Lewinsohn, Portland, OR (US)

(73) Assignees: Oregon Health & Science University, Portland, OR (US); The United States of America as represented by the Department of Veterans Affairs, Washington, DC (US)

(*) Notice: Subject to any disclaimer, the term of this patent is extended or adjusted under 35 U.S.C. 154(b) by 0 days.

(21) Appl. No.: 12/894,051

(22) Filed: Sep. 29, 2010

(65) Prior Publication Data

US 2011/0014224 A1 Jan. 20, 2011

Related U.S. Application Data

(62) Division of application No. 12/282,865, filed as application No. PCT/US2007/006472 on Mar. 14, 2007, now Pat. No. 7,842,299.

(60) Provisional application No. 60/782,364, filed on Mar. 14, 2006.

(51) Int. Cl.
*A61K 39/38* (2006.01)
*A61K 39/00* (2006.01)
*A61K 39/02* (2006.01)
*A61K 39/385* (2006.01)
*A61K 39/04* (2006.01)

(52) U.S. Cl. ............... 424/248.1; 424/184.1; 424/185.1; 424/190.1; 424/193.1; 424/197.11; 424/234.1

(58) Field of Classification Search .................... None
See application file for complete search history.

(56) References Cited

U.S. PATENT DOCUMENTS

| | | | |
|---|---|---|---|
| 6,294,328 B1 | 9/2001 | Fleischmann et al. | |
| 6,384,018 B1 | 5/2002 | Content et al. | |
| 6,555,653 B2 | 4/2003 | Alderson et al. | |
| 7,074,559 B2 | 7/2006 | Kapur et al. | |
| 7,332,340 B2 | 2/2008 | Tyagi et al. | |
| 7,364,869 B2 | 4/2008 | Nixon et al. | |
| 7,424,370 B2* | 9/2008 | Sachdeva et al. | 702/19 |
| 7,510,718 B2 | 3/2009 | Krohn et al. | |
| 7,767,209 B2 | 8/2010 | Staib et al. | |
| 7,842,299 B2* | 11/2010 | Lewinsohn et al. | 424/248.1 |
| 7,867,704 B2* | 1/2011 | Kapur et al. | 435/6 |
| 2002/0098200 A1 | 7/2002 | Campos-Neto et al. | |
| 2002/0176867 A1 | 11/2002 | Anderson et al. | |
| 2002/0192229 A1 | 12/2002 | Flyer et al. | |
| 2003/0147897 A1 | 8/2003 | Anderson et al. | |
| 2003/0175725 A1 | 9/2003 | Kapur et al. | |
| 2004/0029129 A1* | 2/2004 | Wang et al. | 435/6 |
| 2004/0057963 A1 | 3/2004 | Anderson et al. | |
| 2004/0141985 A1 | 7/2004 | Lalvani et al. | |
| 2005/0074822 A1 | 4/2005 | Nixon et al. | |
| 2005/0123511 A1 | 6/2005 | McCreavy et al. | |
| 2005/0288866 A1* | 12/2005 | Sachdeva et al. | 702/19 |
| 2007/0026020 A1* | 2/2007 | Ernst et al. | 424/248.1 |
| 2007/0036816 A1 | 2/2007 | Campos-Neto et al. | |
| 2007/0042383 A1 | 2/2007 | Kapur et al. | |
| 2008/0124549 A1 | 5/2008 | Lee et al. | |
| 2009/0070897 A1 | 3/2009 | Goldman et al. | |
| 2009/0124549 A1 | 5/2009 | Lewinsohn et al. | |
| 2009/0324503 A1 | 12/2009 | Lewinsohn et al. | |
| 2010/0129391 A1 | 5/2010 | Reed et al. | |
| 2011/0014224 A1* | 1/2011 | Lewinsohn et al. | 424/190.1 |
| 2011/0150932 A1* | 6/2011 | Singh et al. | 424/248.1 |
| 2011/0183342 A1* | 7/2011 | Lewinsohn et al. | 435/6.12 |

FOREIGN PATENT DOCUMENTS

| | | |
|---|---|---|
| EP | 1 484 405 | 12/2004 |
| WO | WO 98/53075 | 11/1998 |
| WO | WO 99/24577 | 5/1999 |
| WO | WO 01/51639 A2 | 7/2001 |
| WO | WO 01/62893 | 8/2001 |
| WO | WO 01/74130 | 10/2001 |
| WO | WO 01/79257 A2 | 10/2001 |
| WO | WO 03/033530 A2 | 4/2003 |
| WO | WO 2005/076010 A2 | 8/2005 |
| WO | WO 2005/090988 A2 | 9/2005 |
| WO | WO 2007/106536 | 9/2007 |
| WO | WO 2007/106560 | 9/2007 |
| WO | WO 2009/039854 | 4/2009 |
| WO | WO 2010/034007 | 3/2010 |

OTHER PUBLICATIONS

Greenspan et al, Nature Biotechnology 7: 936-937, 1999.*
Burgess et al., JCB, 1990, 111:2129-2138.*
Lazar et al., Molecular and Cellular Biology, 1988, 8:1247-1252.*
Thomas E. Creighton, in his book, "Proteins: Structures and Molecular Properties, 1984", (pp. 314-315).*
Houghten et al (Vaccine 86, 1986, pp. 21-25).*
Bixler et al, Synthetic Vaccines, vol. 1, 1987, pp. 39-71.*
Bowie et al., Science, 1990, vol. 247, pp. 1306-1310.*
Kumar et al. PNAS 87: 1337-1341 Feb. 1991.*
Thomas E. Creighton, in his book Protein Structure: A Practical Approach, 1989; pp. 184-186.*
Nosoh, Y. et al in "Protein Stability and Stabilization through Protein Engineering, 1991" (chapter 7, p. 197.* Grotzke et al, J. Immunology, 2010, 185:4336-4343.*
Wang et al, Immunology, 2011, 132:482-491.*
Hokey et al, Tuberculosis, 2011, 91:82-85.*
Abebe et al, Clinical and Developmental Immunology, 2011, vol. 2011, 11 pages.*
Ahmad, Clinical and Developmental Immunolgy, 2011, vol. 2011, 17 pages.*
Chaitra et al., "Defining Putative T Cell Epitopes from PE and PPE Families of Proteins of *Mycobacterium tuberculosis* with Vaccine Potential," *Vaccine* 23:1265-1272 (2005).
Cho et al., "Current Issues on Molecular and Immunological Diagnosis of Tuberculosis," *Yonsei Medical Journal* 48(3):347-359 (2007).
Database UniProt Accession No. Q6MWX8, "Rv3350c/PPE56," (Jul. 5, 2004).
Database UniProt Accession No. Q73X11_MYCPA, "MAP_2499," (Jul. 5, 2004).

(Continued)

*Primary Examiner* — Nita M Minnifield
(74) *Attorney, Agent, or Firm* — Klarquist Sparkman, LLP

(57) ABSTRACT

Methods for producing an immune response to *Mycobacterium tuberculosis* (Mtb) are disclosed herein. In several examples, the immune response is a protective immune response. In additional embodiments, methods are disclosed for preventing an infection with Mtb, or treating an infection with Mtb. Pharmaceutical compositions for the prevention and/or treatment of tuberculosis are also disclosed.

18 Claims, 8 Drawing Sheets

OTHER PUBLICATIONS

Database UniProt Accession No. Q79FS8, "Rv1088/PE9," (Jul. 5, 2004).

Database UniProt Accession No. Q7D724, "Rv2847c/PE_PGRS42/MT2561," (Jul. 5, 2004).

Database UniProt Entry: Y1273_MYCTU, "Rv1273cMT1311," (Mar. 15, 2005).

Database UniProt Entry: Y1304_MYCBO, "Mb1304c," (Mar. 15, 2005).

Khan et al., "Profiling Antibodies to *Mycobacterium tuberculosis* by Multiplex Microbead Suspension Arrays for Serodiagnosis of Tuberculosis," *Clinical and Vaccine Immunology* 15(3):433-438 (Mar. 2008).

Krueger et al., "Identification of Human Antigen-Specific T Cells Using MHC Class I and Class II Tetramers," *Current Protocols in Cemtometry* 1-6 (2004).

Lewinsohn et al., "Embracing Interferon-γ Release Assays for Diagnosis of Latent Tuberculosis Infection," *Pediatric Infectious Disease Journal* 28(8):674-675 (Aug. 2009).

Lewinsohn et al., "Interferon-γ Release Assays: New Diagnostic Tests for *Mycobacterium tuberculosis* Infection, and Their Use in Children," *Curr. Opin. Peditar.* 22:71-76 (2010).

Lewinsohn et al., "*Mycobacterium tuberculosis*-Reactive CD8 + T Lymphocytes: The Relative Contribution of Classical Versus Nonclassical HLA Restriction," *J. Immunol.* 165:925-930 (2000).

Mazurek et al., "Guidelines for Using the QuantiFERON®-TB Gold Test for Detecting *Mycobacterium tuberculosis* Infection, United States," *MMWR, Recommendations and Reports* 54(RR15):49-55 (Dec. 16, 2005).

Nyendak et al., "New Diagnostic Methods for Tuberculosis," *Curr. Opin. Infect. Dis.* 22:174-182 (2009).

Pai et al., "Interferon-65 Assays in the Immunodiagnosis of Tuberculosis: a Systematic Review," *Lancet Infectious Diseases* 4:761-776 (2004).

Winthrop et al., "Interferon-Release Assays for Diagnosing *Mycobacterium tuberculosis* Infection in Renal Dialysis Patients," *Clin. J. Am. Soc. Nephrol.* 3:1357-1363 (2008).

Arend et al., "Antigentic Equivalence of Human T-Cell Responses to *Mycobacterium tuberculosis*-Specific RD1-Encoded Protein Antigens ESAT-6 and Culture Filtrate Protein 10 and to Mixtures of Synthetic Peptides," *Infection and Immunity* 68(6):3314-3321 (Jun. 2000).

Berzofsky et al., "Progress on New Vaccine Strategies for the Immunotherapy and Prevention of Cancer," *J. Clin. Invest.* 113:1515-1525 (Jun. 2004).

Bixler et al., *Synthetic Vaccines* 1:39-71 (1987).

Blythe et al., "An Analysis of the Epitope Knowledge Related to Mycobacteria," *Immunome Research* 3(10) 14 pages (2007).

Bowie et al., "Deciphering the Message in Protein Sequences: Tolerance to Science Amino Acid Substitutions," *Science* 247:1306-1310 (1990).

Braibant et al., "The ATP Binding Cassette (ABC) Transport Systems of *Mycobacterium tuberculosis*," *FEMS Microbiol. Rev.* 24(4):449-467 (Oct. 2000).

Brosch et al., "Genome Plasticity of BCG and Impact on Vaccine Efficacy," *PNAS* 104:5596-5601 (Mar. 19, 2007).

Burgess et al., "Possible Dissociation of the Heparin-binding and Mitogenic Activities of Heparin-binding (Acidic Fibroblast) Growth Factor-1 from its Receptor-binding Activities by Site-directed Mutagenesis of a Single Lysine Residue," *Journal of Cell Biology* 111:2129-2138 (1990).

Camus et al., "Re-annotation of the Genome Sequence of *Mycocaterium tuberculosis* H37Rv," *Microbiology* 148:2967-2973 (2002).

Cole et al., "Deciphering the Biology of *Mycobaterium tuberculosis* from the Complete Genome Sequence," *Nature* 393:537-544 (Jun. 1998).

Creighton, *Protein Structure: A Practical Approach*, pp. 184-186 (1989).

Creighton, *Proteins: Structures and Molecular Properties*, pp. 314-315 (1984).

Database Accession No. P0A4W4, "Uncharacterized ABC Transporter ATP-Binding Protein Rv1273c/MT1311," 3pp. (Mar. 2005).

Delogu and Fadda, "The Quest for a New Vaccine Against Tuberculosis," *Journal Infection in Developing Countries* 3(1):5-15 (2009) (Abstract only).

Doherty et al., "Tuberculosis Subunit Vaccines: From Basic Science to Clinical Testing," *Expert Opin. Biol. Ther.* 7(10):1539-1549 (2007).

Ellner, "The Emergence of Extensively Drug-Resistant Tuberculosis: A Global Health Crisis Requiring New Interventions: Part II: Scientific Advances that May Provide Solutions," *CTS* 2(1):80-84 (2008).

Fleishmann et al., "Whole-Genome Comparison of *Mycobacterium tuberculosis* Clinical and Laboratory Strains," *Journal of Bacteriology*, 184(19):5479-5490, (Oct. 2002).

Fleishmann et al., Whole genome comparison of *Mycobacterium tuberculosis* clinical and laboratory strains, Entry C137_MYCTU, *EMBL*, (2002).

Garnier et al., "The Complete Genome Sequence of *Mycobacterium bovis*," *PNAS* 100:7877-7882 (Jun. 3, 2003).

Greenspan and Di Cera, "Defining Epitopes: It's Not as Easy as it Seems," *Nature Biotechnology*, 17:936-937 (Oct. 1999).

Grotzke and Lewinsohn, "Role of CD8+ T lymphocytes in control of *Mycobacterium tuberculosis* infection," *Microbes and Infection*, 7(4):776-788, (Apr. 4, 2005).

Grotzke et al., "Role of CD8+ T lymphocytes in Control of *Mycobacterium Tuberculosis* Infection," *Microbes and Infection* 7:776-788 (2005).

Gupta et al., "Current Status of TB Vaccines," *Vaccine* 25:3742-3751 (Feb. 16, 2007).

Gura et al., "Systems for Identifying New Drugs are Often Faulty," *Science* 278:1041-1042 (Nov. 1997).

Houghten et al., "Relative Importance of Position and Individual Amino Acid Residues in Peptide Antigen-Antiboy Interactions: Implications in the Mechanism of Antigenic Drift and Antigenic Shift," *Vaccines* 86:21-25 (1986).

International Search report for PCT Application No. PCT/US2007/006534; 6 pp., (Oct. 2, 2007).

International Search report for PCT Application No. PCT/US2007/006472; 7 pp., (Nov. 23, 2007).

Kawamura, "Protective Immunity Against *Mycobacterium tuberculosis*," *Kekkaku* 81(11):6887-691 (Nov. 2006) (Abstract only).

Kumar et al., "Amino Acid Variations at a Single Residue in an Autoimmune Peptide Profoundly Affect its Properties: T-Cell Activation, Major Histocompatibility Complex Binding, and Ability to Block Experimental Allergic Encephalomyelitis," *PNAS* 87(4):1337-1341 (Feb. 1990).

Lazar et al., "Transforming Growth Factor α: Mutation of Aspartic Acid 47 and Leucine 48 Results in Different Biological Activities," *Molecular and Cellular Biology*, 8:1247-1252 (Mar. 1988).

Lewinsohn et al., "Immunodominant Tuberculosis CD8 Antigens Preferentially Restricted by HLA-B," *PLoS Pathogens* 3(9):1240-1249 (Sep. 2007).

Lewinsohn et al., "Tuberculosis Immunology in Children: Diagnostic and Therapeutic Challenges and Opportunities," *Int. J. Tuberc. Lung Dis.* 8(5):658-674 (2004).

Lewinsohn, David et al., "Characterization of Human CD8[+] T Cells Reactive with *Mycobacterium tuberculosis*-infected Antigen-presenting Cells," *Journal of Experimental Medicine*, 187(10):1633-1640, (May 18, 1998).

Lewinsohn, Deborah et al., "Human Dendritic Cells Presenting Adenovirally Expressed Antigen Elicit *Mycobacterium tuberculosis*-Specific CD8+ T Cells," American Journal of Respiratory and Critical Care Medicine, 166(6):843-848, (Sep. 15, 2002).

Li et al., "The Complete Genome Sequence of *Mycobacterium avium* Subspecies Paratuberculosis," *PNAS* 102:12344-12349 (Aug. 22, 2005).

Nosoh et al., *Protein Stability and Stabilization Through Protein Engineering*, pp. 197-217 (1991).

Ottenhoff "Overcoming the Global Crisis: "Yes, We Can," but also for TB . . . ?" *Eur. J. Immunol.* 39:2014-2020 (2009).

Ottenhoff et al., "Human CD4 and CD8 T Cell Response to *Mycobacterium tuberculosis*: Antigen Specifically, Function, Implications and Applications," *Handbook of Tuberculosis: Immunology and Cell Biology, eds.* Kaufman et al., 119-155 (2008) (Abstract only).

Rengarajan et al., "Genome-wide Requirements for *Mycobacterium tuberculosis* Adaptation and Survival in Macophages," *PNAS* 102(23):8324-8332 (Jun. 7, 2005).

Restifo et al., "The Promise of Nucleic Acid Vaccines," *Gene Therapy,* 7:89-92 (Jan. 2000).

Sassetti et al., "Genes Required for Mycobacterial Growth Defined by High Density Mutagenesis," *Mol. Microbiol.* 48(1):77-84 (2003).

Seki et al., "Whole Genome Sequence Analysis of *Mycobacterium bovis* Bacillus Calmette-Guérin (BCG) Tokyo 172: A Comparative Study of BCG Vaccine Substrains," *Vaccine* 27:1710-1716 (Feb. 4, 2009).

Smith et al., "Human CD8$^+$ CTL Specific for the Mycobacterial Major Secreted Antigen 85A," *Journal of Immunology,* 165:7088-7095, (2000).

Steinman et al., "Immunotherapy: Bewitched, Bothered, and Bewildered No More," *Science* 305:197-200 (Jul. 2004).

Stinear et al., "Reductive Evolution and Niche Adaptation Inferred from the Genome of *Mycobacterium ulcerans*, the Causative Agent of Buruli Ulcer," *Genome Research* 17:192-200 (Jan. 8, 2007).

Stinear et al., "Insights from the Complete Genome Sequence of *Mycobacterium marinum* on the Evolution of *Mycobacterium tuberculosis*," *Genome Research* 18:729-741 (Apr. 10, 2008).

* cited by examiner a) Identification of Antigen b) Identification of 15mer Peptide c) Identification of Minimal Epitopes d) Identification of Restricting Allele

METHODS FOR PRODUCING AN IMMUNE RESPONSE TO TUBERCULOSIS

CROSS REFERENCE TO RELATED APPLICATIONS

This is a divisional of U.S. patent application Ser. No. 12/282,865, filed Sep. 12, 2008, now U.S. Pat. No. 7,842,299, which is the U.S. national stage of International Application No. PCT/US2007/006472, filed Mar. 14, 2007, which was published in English under PCT Article 21(2), which in turn claims the benefit of U.S. Provisional Application No. 60/782,364, filed Mar. 14, 2006. The prior applications are incorporated herein by reference in their entirety.

STATEMENT OF GOVERNMENT SUPPORT

This invention was made with United States government support pursuant to Grant No. NIH-R01-AI48090 and Grant No. NIH NIAID HHSN266200400081C N01-AI-40081 from the National Institutes of Health. This invention was also made with support from the Department of Veteran's Affairs. The United States government has certain rights in the invention.

FIELD

This application relates to the field of immunology, more specifically to methods for the production of an immune response to tuberculosis antigens.

BACKGROUND

*Mycobacteria* are a genus of aerobic intracellular bacterial organisms that, upon infection of a host, survive within endosomal compartments of monocytes and macrophages. Human mycobacterial diseases include tuberculosis (caused by *M. tuberculosis*), leprosy (caused by *M. leprae*), Bairnsdale ulcers (caused by *M. ulcerans*), and various infections caused by *M. marinum, M. kansasii, M. scrofulaceum, M. szulgai, M. xenopi, M. fortuitum, M. chelonei, M. haemophilum* and *M. intracellulare* (see Wolinsky, E., Chapter 37 in Microbiology: Including Immunology and Molecular Genetics, 3rd Ed., Harper & Row, Philadelphia, 1980).

One third of the world's population harbors *M. tuberculosis* and is at risk for developing tuberculosis (TB). In immunocompromised patients, tuberculosis is increasing at a nearly logarithmic rate, and multidrug resistant strains are appearing. In addition, Mycobacterial strains which were previously considered to be nonpathogenic strains (e.g., *M. avium*) have now become major killers of immunosuppressed AIDS patients. Moreover, current Mycobacterial vaccines are either inadequate (such as the BCG vaccine for *M. tuberculosis*) or unavailable (such as for *M. leprae*) (Kaufmann, S., *Microbiol. Sci.* 4:324-328, 1987; U.S. Congress, Office of Technology Assessment, The Continuing Challenge of Tuberculosis, pp. 62-67, OTA-H-574, U.S. Government Printing Office, Washington, D.C., 1993).

*Mycobacterium tuberculosis* (Mtb)-specific $CD4^+$ and $CD8^+$ T cells are critical for the effective control of Mtb infection. In the mouse model, passive transfer of $CD4^+$ T cells to sublethally irradiated animals renders them less susceptible to Mtb infection (Orme, *J Immunol.* 140:3589-3593, 1988). Mice in which the gene(s) for CD4 ($CD4^{-/-}$) or for MHC Class II molecules are disrupted as well as wild-type mice depleted of $CD4^+$ T cells demonstrate increased susceptibility to Mtb infection (Flory et al., *J Leukoc Biol.* 51:225-229, 1992). In humans, human immunodeficiency virus-infected individuals are exquisitely susceptible to developing tuberculosis (TB) after exposure to Mtb, supporting an essential role for $CD4^+$ T cells (Hirsch et al., *J Infect Dis.* 180:2069-2073, 1999). $CD8^+$ T cells are also important for effective T cell immunity (see Lazarevic and Flynn, *Am J Respir Crit Care Med.* 166:1116-1121, 2002). In humans, Mtb-specific $CD8^+$ T cells have been identified in Mtb-infected individuals and include $CD8^+$ T cells that are both classically HLA-Ia restricted (see, for example, Lewinsohn et al., *J Immunol.* 165:925-930, 2000) and nonclassically restricted by the HLA-Ib molecules HLA-E (Lewinsohn et al., *J Exp Med* 187:1633-1640, 1998). However, there are no vaccines or therapeutic strategies that effectively induce an immune response, such as a CD8 response, to Mtb. Thus, a need remains for agents that can produce an immune response to Mtb that can be used for treatment and/or protection from an Mtb infection.

SUMMARY

Methods for producing an immune response to *Mycobacterium tuberculosis* (Mtb) are disclosed herein. Methods for treating an Mtb infection, or preventing an Mtb infection in a subject, are also disclosed herein. The Mtb infection can be latent or active.

In several embodiments, the methods include administering to the subject a therapeutically effective amount of a polypeptide, or a polynucleotide encoding the polypeptide, wherein the polypeptide comprises at least one of the amino acid sequences set forth as SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11 or SEQ ID NO: 12. In additional embodiments, the methods include administering to the subject a therapeutically effective amount of a polypeptide comprising at least nine to twenty consecutive amino acids of at least one of the amino acid sequences set forth as SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 7, SEQ ID NO: 8, SEQ ID NO: 9, SEQ ID NO: 10, SEQ ID NO: 11 or SEQ ID NO: 12, wherein the nine to twenty consecutive amino acids specifically bind major histocompatibility complex (MHC) class I. In several examples, the immune response is a protective immune response. In additional embodiments, methods are disclosed for preventing an infection with Mtb, or treating an infection with Mtb.

Isolated polypeptides are described herein that include nine to twenty consecutive amino acids of at least one of the amino acid sequences set forth as SEQ ID NOs: 1-12, wherein the nine to twenty consecutive amino acids specifically bind major histocompatibility complex (MHC) class I, wherein the isolated polypeptide does not include any of the full length amino acid sequences set forth as SEQ ID NOs: 1-12. Nucleic acids encoding these polypeptides, vectors including these nucleic acids, host cells including these nucleic acids, and immunogenic compositions including these polypeptides, nucleic acids and/or host cells are also disclosed. Pharmaceutical compositions including a therapeutically effective amount of these polypeptides, nucleic acids, and/or host cells are also described.

The foregoing and other features and advantages will become more apparent from the following detailed description of several embodiments, which proceeds with reference to the accompanying figures.

SEQUENCE LISTING

Figure 1:
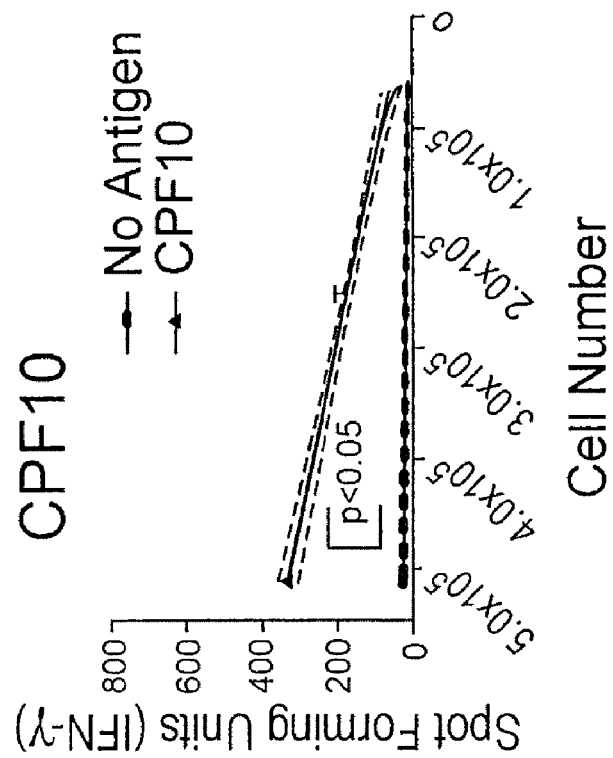
FIG. 1 is two graphs showing the determination of human effector cell frequencies ex vivo using the IFN-γ ELISPOT assay. Magnetic bead-purified CD8+ T cells were cultured with DC (20,000/well) either infected with Mtb (H37Rv, MOI=50) or pulsed with peptide pool representing CFP10 (5 µg/ml each peptide; 15-mers overlap 11 aa) in an IFN-γ ELISPOT assay. Each responding T cell population was tested in duplicate at four different cell concentrations. To determine the effector cell frequency of antigen-specific T cells, the average number of spots per well for each duplicate was plotted against the number of responder cells per well. Linear regression analysis was used to determine the slope of the line, which represents the frequency of antigen-specific T cells. The assay was considered positive (reflecting the presence of a primed T cell response), if the binomial probability for the number of spots was significantly different by experimental and control assays.
Figure 1:
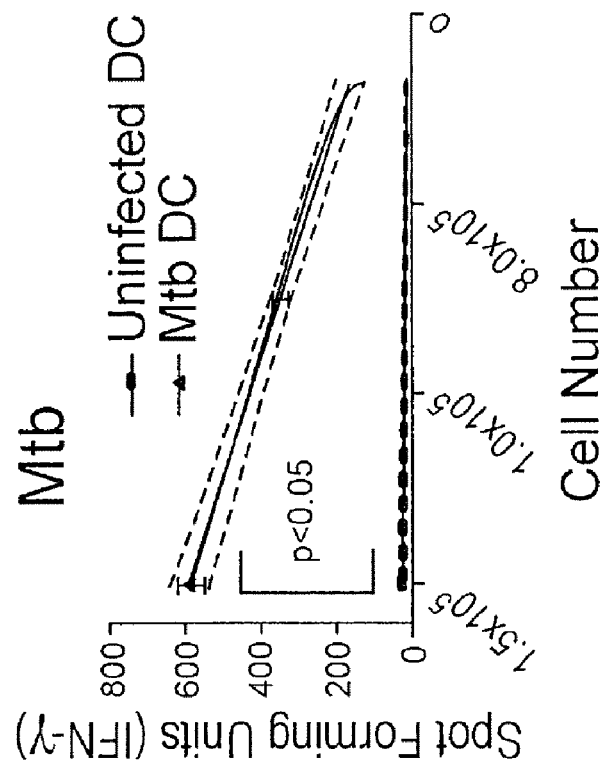

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. In the accompanying sequence listing:

The Sequence Listing is submitted as an ASCII text file [899-77364-19-09_Sequence_Listing.txt, Sep. 29, 2010, 84.4 KB], which is incorporated by reference herein.

SEQ ID NOs: 1-12 are the amino acid sequence of Mtb polypeptides.

SEQ ID NOs: 13-14 are amino acids of Mtb peptides.

SEQ ID NOs: 15-25 are the nucleic acid sequences of polynucleotides encoding the Mtb polypeptides.

SEQ ID NOs: 26-38 are the amino acid sequences of specific Mtb epitopes.

DETAILED DESCRIPTION

Methods for producing an immune response to *Mycobacterium tuberculosis* (Mtb) are disclosed herein. In several examples, the immune response is a protective immune response. In additional embodiments, methods are disclosed for preventing an infection with Mtb, or treating an infection with Mtb. Pharmaceutical compositions for the prevention and/or treatment of tuberculosis are also disclosed.

Terms

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN[1]-56081-569-8).

In order to facilitate review of the various embodiments of this disclosure, the following explanations of specific terms are provided:

Adjuvant: A vehicle used to enhance antigenicity. Adjuvants include a suspension of minerals (alum, aluminum hydroxide, or phosphate) on which antigen is adsorbed; or water-in-oil emulsion in which antigen solution is emulsified in mineral oil (Freund incomplete adjuvant), sometimes with the inclusion of killed mycobacteria (Freund's complete adjuvant) to further enhance antigenicity (inhibits degradation of antigen and/or causes influx of macrophages). Immunostimulatory oligonucleotides (such as those including a CpG motif) can also be used as adjuvants (for example see U.S. Pat. Nos. 6,194,388; 6,207,646; 6,214,806; 6,218,371; 6,239,116; 6,339,068; 6,406,705; and 6,429,199). Adjuvants include biological molecules (a "biological adjuvant"), such as costimulatory molecules. Exemplary adjuvants include IL-2, RANTES, GM-CSF, TNF-α, IFN-γ, G-CSF, LFA-3, CD72, B7-1, B7-2, OX-40L and 41 BBL.

Antigen: A compound, composition, or substance that can stimulate the production of antibodies or a T cell response in an animal, including compositions that are injected or absorbed into an animal. An antigen reacts with the products of specific humoral or cellular immunity, including those induced by heterologous immunogens. The term "antigen" includes all related antigenic epitopes. "Epitope" or "antigenic determinant" refers to a site on an antigen to which B and/or T cells respond. In one embodiment, T cells respond to the epitope, when the epitope is presented in conjunction with an MHC molecule. Epitopes can be formed both from contiguous amino acids or noncontiguous amino acids juxtaposed by tertiary folding of a protein. Generally, T cells recognize epitopes of continuous amino acids. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5, about 9, or about 8-10 amino acids in a unique spatial conformation. Methods of determining spatial conformation of epitopes include, for example, x-ray crystallography and 2-dimensional nuclear magnetic resonance.

An antigen can be a tissue-specific antigen, or a disease-specific antigen. These terms are not exclusive, as a tissue-specific antigen can also be a disease specific antigen. A tissue-specific antigen is expressed in a limited number of tissues, such as a single tissue. A tissue specific antigen may be expressed by more than one related type of tissue, such as alveolar and bronchial tissue. A disease-specific antigen is expressed coincidentally with a disease process. Specific non-limiting examples of a disease-specific antigen are an antigen whose expression correlates with, or is predictive of, tuberculosis. A disease-specific antigen can be an antigen recognized by T cells or B cells.

Amplification: Of a nucleic acid molecule (e.g., a DNA or RNA molecule) refers to use of a technique that increases the number of copies of a nucleic acid molecule in a specimen. An example of amplification is the polymerase chain reaction, in which a biological sample collected from a subject is contacted with a pair of oligonucleotide primers, under conditions that allow for the hybridization of the primers to a nucleic acid template in the sample. The primers are extended under suitable conditions, dissociated from the template, and then re-annealed, extended, and dissociated to amplify the number of copies of the nucleic acid. The product of amplification can be characterized by electrophoresis, restriction endonuclease cleavage patterns, oligonucleotide hybridization or ligation, and/or nucleic acid sequencing using standard techniques. Other examples of amplification include strand displacement amplification, as disclosed in U.S. Pat. No. 5,744,311; transcription-free isothermal amplification, as disclosed in U.S. Pat. No. 6,033,881; repair chain reaction amplification, as disclosed in WO 90/01069; ligase chain reaction amplification, as disclosed in EP-A-320 308; gap filling ligase chain reaction amplification, as disclosed in U.S. Pat. No. 5,427,930; and NASBA™ RNA transcription-free amplification, as disclosed in U.S. Pat. No. 6,025,134.

Antibody: Immunoglobulin molecules and immunologically active portions of immunoglobulin molecules, i.e., molecules that contain an antigen binding site that specifically binds (immunoreacts with) an antigen.

A naturally occurring antibody (e.g., IgG, IgM, IgD) includes four polypeptide chains, two heavy (H) chains and two light (L) chains interconnected by disulfide bonds. However, it has been shown that the antigen-binding function of an antibody can be performed by fragments of a naturally occurring antibody. Thus, these antigen-binding fragments are also intended to be designated by the term "antibody." Specific, non-limiting examples of binding fragments encompassed within the term antibody include (i) a Fab fragment consisting of the $V_L$, $V_H$, $C_L$ and $C_{H1}$ domains; (ii) an $F_d$ fragment consisting of the $V_H$ and $C_{H1}$ domains; (iii) an Fv fragment consisting of the $V_L$ and $V_H$ domains of a single arm of an antibody, (iv) a dAb fragment (Ward et al., *Nature* 341:544-546, 1989) which consists of a $V_H$ domain; (v) an isolated complementarity determining region (CDR); and (vi) a $F(ab)_2$ fragment, a bivalent fragment comprising two Fab fragments linked by a disulfide bridge at the hinge region.

Immunoglobulins and certain variants thereof are known and many have been prepared in recombinant cell culture (e.g., see U.S. Pat. Nos. 4,745,055; 4,444,487; WO 88/03565; EP 256,654; EP 120,694; EP 125,023; Faoulkner et al., *Nature* 298:286, 1982; Morrison, *J. Immunol.* 123:793, 1979; Morrison et al., *Ann Rev. Immunol* 2:239, 1984).

Animal: Living multi-cellular vertebrate organisms, a category that includes, for example, mammals and birds. The term mammal includes both human and non-human mammals. Similarly, the term "subject" includes both human and veterinary subjects.

Antigen presenting cell (APC): A cell that can present an antigen to a T cell, such that the T cells are activated. Dendritic cells are the principle antigen presenting cells (APCs) involved in primary immune responses. Their major function is to obtain antigen in tissues, migrate to lymphoid organs and present the antigen in order to activate T cells.

When an appropriate maturational cue is received, dendritic cells are signaled to undergo rapid morphological and physiological changes that facilitate the initiation and development of immune responses. Among these are the up-regulation of molecules involved in antigen presentation; production of pro-inflammatory cytokines, including IL-12, key to the generation of Th1 responses; and secretion of chemokines that help to drive differentiation, expansion, and migration of surrounding naive Th cells. Collectively, these up-regulated molecules facilitate the ability of dendritic cells to coordinate the activation and effector function of other surrounding lymphocytes that ultimately provide protection for the host.

cDNA (complementary DNA): A piece of DNA lacking internal, non-coding segments (introns) and regulatory sequences that determine transcription. cDNA is synthesized in the laboratory by reverse transcription from messenger RNA extracted from cells.

CD4: Cluster of differentiation factor 4, a T cell surface protein that mediates interaction with the MHC Class II molecule. CD4 also serves as the primary receptor site for HIV on T cells during HIV infection. Cells that express CD4 are often helper T cells.

CD8: Cluster of differentiation factor 8, a T cell surface protein that mediates interaction with the MHC Class I molecule. Cells that express CD8 are often cytotoxic T cells. "CD8+ T cell mediated immunity" is an immune response implemented by presentation of antigens to CD8+ T cells.

cDNA (complementary DNA): A piece of DNA lacking internal, non-coding segments (introns) and regulatory sequences that determine transcription. cDNA is synthesized in the laboratory by reverse transcription from messenger RNA extracted from cells.

Conservative variants: "Conservative" amino acid substitutions are those substitutions that do not substantially affect or decrease an activity or antigenicity of the *Mycobacterium* polypeptide. Specific, non-limiting examples of a conservative substitution include the following examples:

| Original Residue | Conservative Substitutions |
|---|---|
| Ala | Ser |
| Arg | Lys |
| Asn | Gln, His |
| Asp | Glu |
| Cys | Ser |
| Gln | Asn |
| Glu | Asp |
| His | Asn; Gln |
| Ile | Leu, Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

The term conservative variation also includes the use of a substituted amino acid in place of an unsubstituted parent amino acid, provided that antibodies raised to the substituted polypeptide also immunoreact with the unsubstituted polypeptide, or that an immune response can be generated against the substituted polypeptide that is similar to the immune response against and unsubstituted polypeptide, such a *Mycobacterium* antigen. Thus, in one embodiment, non-conservative substitutions are those that reduce an activity or antigenicity.

Consists Essentially Of/Consists Of: With regard to a polypeptide, a polypeptide that consists essentially of a specified amino acid sequence if it does not include any additional amino acid residues. However, the polypeptide can include additional non-peptide components, such as labels (for example, fluorescent, radioactive, or solid particle labels), sugars or lipids. With regard to a polypeptide, a polypeptide that consists of a specified amino acid sequence does not include any additional amino acid residues, nor does it include additional non-peptide components, such as lipids, sugars or labels.

Contacting: The process of incubating one agent in the presence of another. Thus, when a cell is contacted with an agent, the cell is incubated with the agent for a sufficient period of time for the agent and the cell to interact.

Costimulatory molecule: Although engagement of the TCR with peptide-MHC delivers one signal to the T cell, this signal alone can be insufficient to activate the T cell. Costimulatory molecules are molecules that, when bound to their ligand, deliver a second signal required for the T cell to become activated. The most well-known costimulatory molecule on the T cell is CD28, which binds to either B7-1 (also called CD80) or B7-2 (also known as CD86). An additional costimulatory molecule is B7-3. Accessory molecules that also provide a second signal for the activation of T cells include intracellular adhesion molecule (ICAM-1 and ICAM-2), and leukocyte function associated antigen (LFA-1, LFA-2 and LFA-3). Integrins and tumor necrosis factor (TNF) superfamily members can also serve as co-stimulatory molecules.

Cytokine: Proteins made by cells that affect the behavior of other cells, such as lymphocytes. In one embodiment, a cytokine is a chemokine, a molecule that affects cellular trafficking. Specific, non-limiting examples of cytokines include the interleukins (IL-2, IL-4, IL-6, IL-10, IL-21, etc.), and IFN-γ.

Degenerate variant: A polynucleotide encoding an epitope of an Mtb polypeptide that includes a sequence that is degenerate as a result of the genetic code. There are 20 natural amino acids, most of which are specified by more than one codon. Therefore, all degenerate nucleotide sequences are included in this disclosure as long as the amino acid sequence of the Mtb polypeptide encoded by the nucleotide sequence is unchanged.

Dendritic cell (DC): Dendritic cells are the principle antigen presenting cells (APCs) involved in primary immune responses. Dendritic cells include plasmacytoid dendritic cells and myeloid dendritic cells. Their major function is to obtain antigen in tissues, migrate to lymphoid organs and present the antigen in order to activate T cells. Immature dendritic cells originate in the bone marrow and reside in the periphery as immature cells.

Diagnostic: Identifying the presence or nature of a pathologic condition, such as, but not limited to, tuberculosis. Diagnostic methods differ in their sensitivity and specificity. The "sensitivity" of a diagnostic assay is the percentage of diseased individuals who test positive (percent of true positives). The "specificity" of a diagnostic assay is 1 minus the false positive rate, where the false positive rate is defined as the proportion of those without the disease who test positive. While a particular diagnostic method may not provide a definitive diagnosis of a condition, it suffices if the method provides a positive indication that aids in diagnosis. "Prognostic" means predicting the probability of development (for example, severity) of a pathologic condition, such as tuberculosis.

Displaying: The process of localizing a peptide:antigen complex, or a peptide, on the outer surface of a cell where the peptide:antigen complex or peptide is accessible to a second cell, molecules displayed by a second cell, or soluble factors. A peptide, or a peptide:antigen complex, is "displayed" by a cell when it is present on the outer surface of the cell and is accessible to a second cell, to molecules displayed by the second cell, or to soluble factors.

Epitope: An antigenic determinant. These are particular chemical groups or peptide sequences on a molecule that are antigenic, i.e. that elicit a specific immune response. An antibody specifically binds a particular antigenic epitope on a polypeptide, such a *Mycobacterium* polypeptide.

Expression Control Sequences: Nucleic acid sequences that regulate the expression of a heterologous nucleic acid sequence to which it is operatively linked. Expression control sequences are operatively linked to a nucleic acid sequence when the expression control sequences control and regulate the transcription and, as appropriate, translation of the nucleic acid sequence. Thus expression control sequences can include appropriate promoters, enhancers, transcription terminators, a start codon (i.e., ATG) in front of a protein-encoding gene, splicing signal for introns, maintenance of the correct reading frame of that gene to permit proper translation of mRNA, and stop codons. The term "control sequences" is intended to include, at a minimum, components whose presence can influence expression, and can also include additional components whose presence is advantageous, for example, leader sequences and fusion partner sequences. Expression control sequences can include a promoter.

A promoter is a minimal sequence sufficient to direct transcription. Also included are those promoter elements which are sufficient to render promoter-dependent gene expression controllable for cell-type specific, tissue-specific, or inducible by external signals or agents; such elements may be located in the 5' or 3' regions of the gene. Both constitutive and inducible promoters, are included (see e.g., Bitter et al., *Methods in Enzymology* 153:516-544, 1987). For example, when cloning in bacterial systems, inducible promoters such as pL of bacteriophage lambda, plac, ptrp, ptac (ptrp-lac hybrid promoter) and the like may be used. In one embodiment, when cloning in mammalian cell systems, promoters derived from the genome of mammalian cells (e.g., metallothionein promoter) or from mammalian viruses (e.g., the retrovirus long terminal repeat; the adenovirus late promoter; the vaccinia virus 7.5K promoter) can be used. Promoters produced by recombinant DNA or synthetic techniques may also be used to provide for transcription of the nucleic acid sequences. In one embodiment, the promoter is a cytomegalovirus promoter.

Fractionating: Subjecting a sample to conditions or procedures which separate the components of the sample based on physical or chemical properties such as, but not limited to, size, charge, solubility, or composition. Example of fractionation procedures include, but are not limited to, selective precipitation, organic extraction, size exclusion dialysis or chromatography, such as ion exchange chromatography. In one embodiment, a fraction is a soluble extract or an organic extract of an organism, such as a *Mycobacterium*.

Functionally Equivalent Sequence alterations, such as in an epitope of an antigen, that yield the same results as described herein. Such sequence alterations can include, but are not limited to, conservative substitutions, deletions, mutations, frameshifts, and insertions.

Heterologous: Originating from separate genetic sources or species. A polypeptide that is heterologous to an Mtb polypeptide originates from a nucleic acid that does not encode the Mtb polypeptide. In one specific, non-limiting example, a polypeptide comprising nine consecutive amino acids from an Mtb polypeptide, or at most 20 consecutive amino acids from the Mtb polypeptide, and a heterologous amino acid sequence includes a β-galactosidase, a maltose binding protein, albumin, hepatitis B surface antigen, or an immunoglobulin amino acid sequence. Generally, an antibody that specifically binds to a protein of interest will not specifically bind to a heterologous protein.

Host cells: Cells in which a vector can be propagated and its DNA expressed. The cell may be prokaryotic or eukaryotic. The cell can be mammalian, such as a human cell. The term also includes any progeny of the subject host cell. It is understood that all progeny may not be identical to the parental cell since there may be mutations that occur during replication. However, such progeny are included when the term "host cell" is used.

Human Leukocyte Antigen (HLA): A genetic designation of the human major histocompatibility complex (MHC). Individual loci are designated by uppercase letters, as in HLA-E, and alleles are designated by numbers, as in HLA-A*0201. The three main MHC class I genes are called HLA-A, HLA-B, and HLA-C. However, there are many genes that encode 132 microglobulin-associated cell surface molecules that are linked to the MHC class I genes. The expression of these genes is variable, both in the tissue distribution and the amount expressed on cells; these genes have been termed the MHC class IB genes.

Immune response: A response of a cell of the immune system, such as a B cell, natural killer cell, or a T cell, to a stimulus. In one embodiment, the response is specific for a particular antigen (an "antigen-specific response"). In one embodiment, an immune response is a T cell response, such as a Th1, Th2, or Th3 response. In another embodiment, an immune response is a response of a suppressor T cell.

Immunogenic peptide: A peptide which comprises an allele-specific motif or other sequence such that the peptide will bind an MHC molecule and induce a cytotoxic T lymphocyte ("CTL") response, or a B cell response (e.g. antibody production) against the antigen from which the immunogenic peptide is derived.

In one embodiment, immunogenic peptides are identified using sequence motifs or other methods, such as neural net or polynomial determinations, known in the art. Typically, algorithms are used to determine the "binding threshold" of peptides to select those with scores that give them a high probability of binding at a certain affinity and will be immunogenic. The algorithms are based either on the effects on MHC binding of a particular amino acid at a particular position, the effects on antibody binding of a particular amino acid at a particular position, or the effects on binding of a particular substitution in a motif-containing peptide. Within the context of an immunogenic peptide, a "conserved residue" is one which appears in a significantly higher frequency than would be expected by random distribution at a particular position in a peptide. In one embodiment, a conserved residue is one where the MHC structure may provide a contact point with the immunogenic peptide.

Immunogenic peptides can also be identified by measuring their binding to a specific MHC protein and by their ability to stimulate CD4 and/or CD8 when presented in the context of the MHC protein.

In one example, an immunogenic "Mtb peptide" is a series of contiguous amino acid residues from the Mtb protein generally between 9 and 20 amino acids in length, such as about 9 to 12 residues in length. Specific immunogenic polypeptides are disclosed herein that are 9 or 10 amino acid residues in length, or at most 12 amino acids in length. Generally, immunogenic Mtb polypeptides can be used to induce an immune response in a subject, such as a B cell response or a T cell response. In one example, an immunogenic Mtb polypeptide, when bound to a MHC Class I molecule, activates cytotoxic T lymphocytes (CTLs) against Mtb. Induction of CTLs using synthetic peptides and CTL cytotoxicity assays are known in the art, see U.S. Pat. No. 5,662,907, which is incorporated herein by reference. In one example, an immunogenic peptide includes an allele-specific motif or other sequence such that the peptide will bind an MHC molecule and induce a cytotoxic T lymphocyte ("CTL") response against the antigen from which the immunogenic peptide is derived.

Immunogenic composition: A composition comprising an immunogenic Mtb polypeptide or a nucleic acid encoding the immunogenic Mtb polypeptide that induces a measurable CTL response against Mtb, or induces a measurable B cell response (such as production of antibodies that specifically bind an Mtb polypeptide). For in vitro use, the immunogenic composition can consist of the isolated nucleic acid, vector including the nucleic acid/or immunogenic peptide. For in vivo use, the immunogenic composition will typically comprise the nucleic acid, vector including the nucleic acid, and or immunogenic polypeptide, in pharmaceutically acceptable carriers, and/or other agents. An immunogenic composition can optionally include an adjuvant, a costimulatory molecule, or a nucleic acid encoding a costimulatory molecule. An Mtb polypeptide, or nucleic acid encoding the polypeptide, can be readily tested for its ability to induce a CTL by art-recognized assays.

Inhibiting or treating a disease: Inhibiting a disease, such as tuberculosis, refers to inhibiting the full development of a disease. In several examples, inhibiting a disease refers to lessening symptoms of a tuberculosis. "Treatment" refers to a therapeutic intervention that ameliorates a sign or symptom of a disease or pathological condition related to the disease, such as tuberculosis.

Interferon gamma (γ): IFN-γ is a dimeric protein with subunits of 146 amino acids. The protein is glycosylated at two sites, and the pI is 8.3-8.5. IFN-γ is synthesized as a precursor protein of 166 amino acids including a secretory signal sequence of 23 amino acids. Two molecular forms of the biologically active protein of 20 and 25 kDa have been described. Both of them are glycosylated at position 25. The 25 kDa form is also glycosylated at position 97. The observed differences of natural IFN-γ with respect to molecular mass and charge are due to variable glycosylation patterns. 40-60 kDa forms observed under non-denaturing conditions are dimers and tetramers of IFN-γ. The human gene has a length of approximately 6 kb. It contains four exons and maps to chromosome 12q24.1.

IFN-γ can be detected by sensitive immunoassays, such as an ELISPOT test that allows detection of individual cells producing IFN-γ. Minute amounts of IFN-γ can be detected indirectly by measuring IFN-induced proteins such as Mx protein. The induction of the synthesis of IP-10 has been used also to measure IFN-γ concentrations. In addition, bioassays can be used to detect IFN-γ, such as an assay that employs induction of indoleamine 2,3-dioxygenase activity in 2D9 cells. The production of IFN-γ can be used to assess T cell activation, such as activation of a T cell by an HLA-E presented *Mycobacterium* antigen.

Isolated: An "isolated" nucleic acid has been substantially separated or purified away from other nucleic acid sequences in the cell of the organism in which the nucleic acid naturally occurs, i.e., other chromosomal and extrachromosomal DNA and RNA. The term "isolated" thus encompasses nucleic acids purified by standard nucleic acid purification methods. The term also embraces nucleic acids prepared by recombinant expression in a host cell as well as chemically synthesized nucleic acids.

Label: A detectable compound or composition that is conjugated directly or indirectly to another molecule to facilitate detection of that molecule. Specific, non-limiting examples of labels include fluorescent tags, enzymatic linkages, and radioactive isotopes.

Linker sequence: A linker sequence is an amino acid sequence that covalently links two polypeptide domains. Linker sequences can be included in between the Mtb epitopes disclosed herein to provide rotational freedom to the linked polypeptide domains and thereby to promote proper domain folding and presentation to the MHC. By way of example, in a recombinant polypeptide comprising two Mtb domains, linker sequences can be provided between them, such as a polypeptide comprising Mtb polypeptide-linker-Mtb polypeptide. Linker sequences, which are generally between 2 and 25 amino acids in length, are well known in the art and include, but are not limited to, the glycine(4)-serine spacer (GGGGS x3) described by Chaudhary et al., *Nature* 339:394-397, 1989.

Lymphocytes: A type of white blood cell that is involved in the immune defenses of the body. There are two main types of lymphocytes: B cells and T cells.

Mammal: This term includes both human and non-human mammals. Similarly, the term "patient" or "subject" includes both human and veterinary subjects.

*Mycobacteria*: A genus of aerobic intracellular bacterial organisms. Upon invasion of a host, these organisms survive within endosomal compartments of monocytes and macrophages. Human mycobacterial diseases include tuberculosis (cause by *M. tuberculosis*), Leprosy (caused by *M. leprae*), Bairnsdale ulcers (caused by *M. ulcerans*), and other infections that can be caused by *M. marinum, M. kansasii, M. scrofulaceum, M. szulgai, M. xenopi, M. fortuitum, M. haemophilum, M. chelonei*, and *M. intracelluare. Mycobacterium* strains that were previously considered to be nonpathogenic (such as *M. avium*) are also now known to be major killers of immunosuppressed AIDS patients.

An immune response to mycobacteria can involve cell mediated hypersensitivity (DTH) reactions with T cells and macrophages playing major roles in the intracellular killing and walling off (or containing) of the organism (granuloma formation). A T cell response can involve $CD4^+$ lymphocytes that recognize myocbacterial heat shock proteins and immunodominant antigens as well as $CD8^+$ cells.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter effects the transcription or expression of the coding sequence. Generally, operably linked DNA sequences are contiguous and, where necessary to join two protein coding regions, the open reading frames are aligned.

ORF (open reading frame): A series of nucleotide triplets (codons) coding for amino acids without any termination codons. These sequences are usually translatable into a polypeptide.

Peptide Modifications: *Mycobacterium* polypeptides include synthetic embodiments of peptides described herein. In addition, analogues (non-peptide organic molecules), derivatives (chemically functionalized peptide molecules obtained starting with the disclosed peptide sequences) and variants (homologs) of these proteins can be utilized in the methods described herein. Each polypeptide of the invention is comprised of a sequence of amino acids, which may be either L- and/or D-amino acids, naturally occurring and otherwise.

Peptides may be modified by a variety of chemical techniques to produce derivatives having essentially the same activity as the unmodified peptides, and optionally having other desirable properties. For example, carboxylic acid groups of the protein, whether carboxyl-terminal or side chain, may be provided in the form of a salt of a pharmaceutically-acceptable cation or esterified to form a $C_1$-$C_{16}$ ester, or converted to an amide of formula $NR_1R_2$ wherein $R_1$ and $R_2$ are each independently H or $C_1$-$C_{16}$ alkyl, or combined to form a heterocyclic ring, such as a 5- or 6-membered ring. Amino groups of the peptide, whether amino-terminal or side chain, may be in the form of a pharmaceutically-acceptable acid addition salt, such as the HCl, HBr, acetic, benzoic, toluene sulfonic, maleic, tartaric and other organic salts, or may be modified to $C_1$-$C_{16}$ alkyl or dialkyl amino or further converted to an amide.

Hydroxyl groups of the peptide side chains may be converted to $C_1$-$C_{16}$ alkoxy or to a $C_1$-$C_{16}$ ester using well-recognized techniques. Phenyl and phenolic rings of the peptide side chains may be substituted with one or more halogen atoms, such as fluorine, chlorine, bromine or iodine, or with $C_1$-$C_{16}$ alkyl, $C_1$-$C_{16}$ alkoxy, carboxylic acids and esters thereof, or amides of such carboxylic acids. Methylene groups of the peptide side chains can be extended to homologous $C_2$-$C_4$ alkylenes. Thiols can be protected with any one of a number of well-recognized protecting groups, such as acetamide groups. Those skilled in the art will also recognize methods for introducing cyclic structures into the peptides of this invention to select and provide conformational constraints to the structure that result in enhanced stability.

Peptidomimetic and organomimetic embodiments are envisioned, whereby the three-dimensional arrangement of the chemical constituents of such peptido- and organomimetics mimic the three-dimensional arrangement of the peptide backbone and component amino acid side chains, resulting in such peptido- and organomimetics of a *Mycobacterium* polypeptide having measurable or enhanced ability to generate an immune response. For computer modeling applications, a pharmacophore is an idealized, three-dimensional definition of the structural requirements for biological activity. Peptido- and organomimetics can be designed to fit each pharmacophore with current computer modeling software (using computer assisted drug design or CADD). See Walters, "Computer-Assisted Modeling of Drugs", in Klegerman & Groves, eds., 1993, *Pharmaceutical Biotechnology*, Interpharm Press: Buffalo Grove, Ill., pp. 165-174 and *Principles of Pharmacology* Munson (ed.) 1995, Ch. 102, for descriptions of techniques used in CADD. Also included are mimetics prepared using such techniques.

Pharmaceutical agent or drug: A chemical compound or composition capable of inducing a desired therapeutic or prophylactic effect when properly administered to a subject.

Pharmaceutically acceptable carriers: The pharmaceutically acceptable carriers useful with the polypeptides and nucleic acids described herein are conventional. *Remington's Pharmaceutical Sciences*, by E. W. Martin, Mack Publishing Co., Easton, Pa., 15th Edition (1975), describes compositions and formulations suitable for pharmaceutical delivery of the fusion proteins herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Polynucleotide: A linear nucleotide sequence, including sequences of greater than 100 nucleotide bases in length.

Polypeptide: Any chain of amino acids, regardless of length or post-translational modification (e.g., glycosylation or phosphorylation). A "peptide" is a chain of amino acids that is less than 100 amino acids in length. In one embodiment, a "peptide" is a portion of a polypeptide, such as at about 10, 20, 30, 40, 50, or 100 contiguous amino acids of a polypeptide that is greater than 100 amino acids in length.

Portion of a nucleic acid sequence: At least 10, 20, 30 or 40 contiguous nucleotides of the relevant sequence, such as a sequence encoding an antigen. In some instances it would be advantageous to use a portion consisting of 50 or more nucleotides. For instance, when describing a portion of an antigen (such as an antigenic epitope), it may be advantageous to remove a portion of the relevant sequence comprising at least 10, 20, 30, 40 or 50 nucleotides up to a length.

Probes and primers: Nucleic acid probes and primers may readily be prepared based on the nucleic acids provided by this invention. A probe comprises an isolated nucleic acid attached to a detectable label or reporter molecule. Typical labels include radioactive isotopes, ligands, chemiluminescent agents, and enzymes. Methods for labeling and guidance in the choice of labels appropriate for various purposes are discussed, e.g., in Sambrook et al. (1989) and Ausubel et al. (1987).

Primers are short nucleic acids, preferably DNA oligonucleotides 15 nucleotides or more in length. Primers may be annealed to a complementary target DNA strand by nucleic acid hybridization to form a hybrid between the primer and the target DNA strand, and then extended along the target DNA strand by a DNA polymerase enzyme. Primer pairs can be used for amplification of a nucleic acid sequence, e.g., by the polymerase chain reaction (PCR) or other nucleic-acid amplification methods known in the art.

Methods for preparing and using probes and primers are described, for example, in *Molecular Cloning: A Laboratory Manual,* 2nd ed., vol. 1-3, ed. Sambrook et al., Cold Spring Harbor Laboratory Press, Cold Spring Harbor, N.Y., 1989, and *Current Protocols in Molecular Biology*, ed. Ausubel et al., Greene Publishing and Wiley-Interscience, New York, 1987 (with periodic updates). PCR primer pairs can be derived from a known sequence, for example, by using computer programs intended for that purpose such as Primer (Version 0.5, © 1991, Whitehead Institute for Biomedical Research, Cambridge, Mass.).

Preventing or treating a disease: "Preventing" a disease refers to inhibiting the full development of a disease, for example in a person who is known to be at risk of infection with *M. tuberculosis*, or *M. leprae*. An example of a person with a known predisposition is someone living with a person diagnosed with tuberculosis, health care professionals, or someone otherwise known to have been exposed to *M. tuberculosis*. "Treatment" refers to a therapeutic intervention that ameliorates a sign or symptom of a disease or pathological condition, such as tuberculosis, after it has begun to develop.

Promoter: A promoter is an array of nucleic acid control sequences which direct transcription of a nucleic acid. A promoter includes necessary nucleic acid sequences near the start site of transcription, such as, in the case of a polymerase II type promoter, a TATA element. A promoter also optionally includes distal enhancer or repressor elements which can be located as much as several thousand base pairs from the start site of transcription. The promoter can be a constitutive or an inducible promoter. A specific, non-limiting example of a promoter is the HCMV IE promoter.

Purified: The term purified does not require absolute purity; rather, it is intended as a relative term. Thus, for example, a purified antigen preparation is one in which the antigen is more pure than the protein in its originating environment within a cell. A preparation of an antigen is typically purified such that the antigen represents at least 50% of the total protein content of the preparation. However, more highly purified preparations may be required for certain applications. For example, for such applications, preparations in which the antigen comprises at least 75% or at least 90% of the total protein content may be employed.

Recombinant: A recombinant nucleic acid or polypeptide is one that has a sequence that is not naturally occurring or has a sequence that is made by an artificial combination of two or more otherwise separated segments of sequence. This artificial combination is often accomplished by chemical synthesis or, more commonly, by the artificial manipulation of isolated segments of nucleic acids, e.g., by genetic engineering techniques.

Sequence identity: The similarity between amino acid sequences is expressed in terms of the similarity between the sequences, otherwise referred to as sequence identity. Sequence identity is frequently measured in terms of percentage identity (or similarity or homology); the higher the percentage, the more similar the two sequences are. Variants of antigen polypeptides will possess a relatively high degree of sequence identity when aligned using standard methods.

Methods of alignment of sequences for comparison are well known in the art. Altschul et al. (1994) presents a detailed consideration of sequence alignment methods and homology calculations. The NCBI Basic Local Alignment Search Tool (BLAST) (Altschul et al., 1990) is available from several sources, including the National Center for Biotechnology Information (NCBI, Bethesda, Md.) and on the Internet, for use in connection with the sequence analysis programs blastp, blastn, blastx, tblastn and tblastx. It can be accessed at the NCBI website. A description of how to determine sequence identity using this program is available at the NCBI website, as are the default parameters.

Variants of antigenic polypeptides, such as a *Mycobacterium* polypeptide, are typically characterized by possession of at least 50% sequence identity counted over the full length alignment with the amino acid sequence of a native antigen sequence using the NCBI Blast 2.0, gapped blastp set to default parameters. Proteins with even greater similarity to the reference sequences will show increasing percentage identities when assessed by this method, such as at least 60%, at least 65%, at least 70%, at least 75%, at least 80%, at least 90% or at least 95% sequence identity. When less than the entire sequence is being compared for sequence identity, variants will typically possess at least 75% sequence identity over short windows of 10-20 amino acids, and may possess sequence identities of at least 85% or at least 90% or 95% depending on their similarity to the reference sequence. Methods for determining sequence identity over such short windows are described at the NCBI website. Variants of MHC domain polypeptides also retain the biological activity of the native polypeptide.

Therapeutically active polypeptide: An agent, such as an epitope of Mtb that causes induction of an immune response, as measured by clinical response (such as an increase in a population of immune cells, increased cytolytic activity against Mtb, or measurable reduction of a symptom of an infection). Therapeutically active molecules can also be made from nucleic acids. Examples of a nucleic acid based therapeutically active molecule is a nucleic acid sequence that encodes a Mtb epitope, wherein the nucleic acid sequence is operably linked to a control element such as a promoter.

Therapeutically effective dose: A dose sufficient to prevent advancement, or to cause regression of the disease, or which is capable of relieving symptoms caused by the disease. In one embodiment, a therapeutically effective dose is a dose sufficient to prevent advancement or relieve symptoms of tuberculosis.

Transduced and Transformed: A virus or vector "transduces" a cell when it transfers nucleic acid into the cell. A cell is "transformed" by a nucleic acid transduced into the cell when the DNA becomes stably replicated by the cell, either by incorporation of the nucleic acid into the cellular genome, or by episomal replication. As used herein, the term transformation encompasses all techniques by which a nucleic acid molecule might be introduced into such a cell, including transfection with viral vectors, transformation with plasmid vectors, and introduction of naked DNA by electroporation, lipofection, and particle gun acceleration.

Tuberculosis (TB): A disease that is generally caused by *Mycobacterium tuberculosis* that usually infects the lungs. However, other "atypical" mycobacteria such as *M. kansasii* may produce a similar clinical and pathologic appearance of disease.

Transmission of *M. tuberculosis* occurs by the airborne route in confined areas with poor ventilation. In more than 90% of cases, following infection with *M. tuberculosis*, the immune system prevents development of disease from *M. tuberculosis*, often called, active tuberculosis. However, not all of the *M. tuberculosis* is killed, and thus tiny, hard capsules are formed. "Primary tuberculosis" is seen disease that develops following an initial infection, usually in children. The initial focus of infection is a small subpleural granuloma accompanied by granulomatous hilar lymph node infection. Together, these make up the Ghon complex. In nearly all cases, these granulomas resolve and there is no further spread of the infection. "Secondary tuberculosis" is seen mostly in adults as a reactivation of previous infection (or reinfection), particularly when health status declines. The granulomatous inflammation is much more florid and widespread. Typically, the upper lung lobes are most affected, and cavitation can occur. Dissemination of tuberculosis outside of lungs can lead to the appearance of a number of uncommon findings with characteristic patterns that include skeletal tuberculosis, genital tract tuberculosis, urinary tract tuberculosis, central nervous system (CNS) tuberculosis, gastrointestinal tuberculosis, adrenal tuberculosis, scrofula, and cardiac tuberculosis. "Latent" tuberculosis is an Mtb infection in an individual that can be detected by a diagnostic assay, such as, but not limited to a tuberculin skin test (TST) wherein the infection does not produce symptoms in that individual. "Active" tuberculosis is a symptomatic Mtb infection in a subject.

Microscopically, the inflammation produced with TB infection is granulomatous, with epithelioid macrophages and Langhans giant cells along with lymphocytes, plasma cells, maybe a few polymorphonuclear cells, fibroblasts with collagen, and characteristic caseous necrosis in the center. The inflammatory response is mediated by a type IV hypersensitivity reaction, and skin testing is based on this reaction. In some examples, tuberculosis can be diagnosed by a skin test, an acid fast stain, an auramine stain, or a combination thereof. The most common specimen screened is sputum, but the histologic stains can also be performed on tissues or other body fluids.

TB is a frequent complication of HIV infection. TB infection in subjects infected with a human immunodeficiency virus (HIV) can spread readily and progress rapidly to active disease. Specific symptoms of lung disease due to Mtb infection include chronic cough and spitting blood. Other symptoms of TB disease include fatigue, loss of appetite, weight loss, fever and drenching night sweats.

Vector: A nucleic acid molecule as introduced into a host cell, thereby producing a transduced or transformed host cell. A vector may include nucleic acid sequences that permit it to replicate in a host cell, such as an origin of replication. A vector may also include one or more selectable marker gene and other genetic elements known in the art. Vectors include plasmid vectors, including plasmids for expression in gram negative and gram positive bacterial cells. Exemplary vectors include those for expression in *E. coli* and *Salmonella*. Vectors also include viral vectors, such as, but are not limited to, retrovirus, orthopox, avipox, fowlpox, capripox, suipox, adenoviral, herpes virus, alpha virus, baculovirus, Sindbis virus, vaccinia virus and poliovirus vectors. Vectors also include vectors for expression in yeast cells.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." All publications, patent applications, patents, and other references mentioned herein are incorporated by reference in their entirety. In case of conflict, the present specification, including explanations of terms, will control. In addition, the materials, methods, and examples are illustrative only and not intended to be limiting.

*Mycobacterium* Polypeptides

It is disclosed herein that several *Mycobacterium* polypeptides can be used to induce an immune response to Mtb, such as a T cell response. In several embodiments, the polypeptide comprises or consists of the amino acid sequence set forth as:

1. MX1SRFMTDPHAMRDMAGRFEVHAQTVEDEARRMWASAQNISG

AGWSGMAEATSLDTMX<sub>2</sub>X<sub>3</sub>MNQAFRNIVNMLHGVRDGLVRDANNY

EQQEQASQQILS,
(SEQ ID NO: 1, wherein X1 is A or T, X<sub>2</sub> is
T or A and X<sub>3</sub> is any amino acid, such as Q
or no amino acid)

In several examples, the polypeptide comprises or consists of the amino acid sequence set forth as:

a. MASRFMTDPHAMRDMAGRFEVHAQTVEDEARRMWASAQNISGA

GWSGMAEATSLDTMTQMNQAFRNIVNMLHGVRDGLVRDANNYEQ

QEQASQQILS
(SEQ ID NO: 2) (See also TUBERCULIST No.
Rv1038c, as available on Mar. 1, 2007,
incorporated herein by reference, known as
EsxJ, ES6_2, TB11.0, QILSS)

b. MASRFMTDPHAMRDMAGRFEVHAQTVEDEARRMWASAQNISG

AGWSGMAEATSLDTMAQMNQAFRNIVNMLHGVRDGLVRDANNYE

QQEQASQQILSS
(SEQ ID NO: 3, TUBERCULIST No. Rv1197, as
available on Mar. 1, 2007, incorporated
herein by reference, also know as EsxK,
ES6_3, TB11.0, QILSS)

c. MASRFMTDPHAMRDMAGRFEVHAQTVEDEARRMWASAQNISG

AGWSGMAEATSLDTMT + MNQAFRNIVNMLHGVRDGLVRDANNYE

QQEQASQQILSS
(SEQ ID NO: 4, TUBERCULIST No. Rv 1992,
as available on Mar. 1, 2007, incorporated
herein by reference, as known as EsxM,
TB11.0, QILSS.

-continued d. MATRFMTDPHAMRDMAGRFEVHAQTVEDEARRMWASAQNISG

AGWSGMAEATSLDTMAQMNQAFRNIVNMLHGVRDGLVRDANNYE

QQEQASQQILSS
(SEQ ID NO: 5, TUBERCULIST No. Rv 2347c,
as available on Mar. 1, 2007, incorporated
herein by reference, also known as EsxP,
ES6_7, QILSS)

e. MTSRFMTDPHAMRDMAGRFEVHAQTVEDEARRMWASAQNISG

AGWSGMAEATSLDTMTQMNQAFRNIVNMLHGVRDGLVRDANNYE

QQEQASQQILSS
(SEQ ID NO: 6, TUBERCULIST No. Rv3620c,
as available on Mar. 1, 2007, incorporated
herein by reference, also known as
EsxW, ES6_10, QILSS).

In additional embodiments, the polypeptide comprises or consists of the amino acid sequence set forth as:

2. MSYMIATPAALTAAATDIDGIGSAVSVANAAAVAATTGVLAAGG

DEVLAAIARLFNANAEEYHALSAQVAAFQTLFVRTLTGGCGVFRRR

RGRQCVTAAEHRAAGAGRRQRRRRSGDGQW

RLRQQRHFGCGGQPEFRQHSEHRR
(SEQ ID NO: 7, TUBERCULIST NO. Rv1088, as
available on Mar. 1, 2007, incorporated
herein by reference, also known as PE9).

3. VSLVIATPQLLATAALDLASIGSQVSAANAAAAMPTTEVVAAAA

DEVSAAIAGLFGAHARQYQALSVQVAAFHEQFVQALTAAAGRYAST

EAAVERSLLGAVNAPTEALLGRPLIGNGADGTAPGQPGAAGGLLFG

NGGNGAAGGFGQTGGSGGAAGLIGNGGNGGAGGTGAAGGAGGNG

GWLWGNGGNGGVGGTSVAAGIGGAGGNGGNAGLFGHGGAGGTG

GAGLAGANGVNPTPGPAASTGDSPADVSGIGDQTGGDGGTGGHGTA

GTPTGGTGGDGATATAGSGKATGGAGGDGGTAAAGGGGGNGGDG

GVAQGDIASAFGGDGGNGSDGVAAGSGGGSGGAGGGAFVHIATAT

STGGSGGFGGNGAASAASGADGGAGGAGGNGGAGGLLFGDGGNG

GAGGAGGIGGDGATGGPGGSGGNAGIARFDSPDPEAEPDVVGGKGG

DGGKGGSGLGVGGAGGTGGAGGNGGAGGLLFGNGGNGGNAGAGG

DGGAGVAGGVGGNGGGGGTATFHEDPVAGVWAVGGVGGDGGSG

GSSLGVGGVGGAGGVGGKGGASGMLIGNGGNGGSGGVGGAGGVG

GAGGDGGNGGSGGNASTFGDENSIGGAGGTGGNGGNGANGGNGG

AGGIAGGAGGSGGFLSGAAGVSGADGIGGAGGAGGAG

GAGGSGGEAGAGGLTNGPGSPGVSGTEGMAGAPG
(SEQ ID NO: 8, TUBERCULIST NO. Rv2487, as
available on Mar. 1, 2007, incorporated
herein by reference, also known as PE_PGRS42)

4. MHQVDPNLTRRKGRLAALAIAAMASASLVTVAVPATANADPEPA

PPVPTTAASPPSTAAAPPAPATPVAPPPPAAANTPNAQPGDPNAAPPP

ADPNAPPPPVIAPNAPQPVRIDNPVGGFSFALPAGWVESDAAHFDYG

SALLSKTTGDPPFPGQPPPVANDTRIVLGRLDQKLYASAEATDSKAA

ARLGSDMGEFYMPYPGTRINQETVSLDANGVSGSASYYEVKFSDPSK

-continued
PNGQIWTGVIGSPAANAPDAGPPQRWFVVWLGTANNPVDKGAAKA

LAESIRPLVAPPPAPAPAPAEP APAPAPAGEVAPTPTTPTPQRTLPA
(SEQ ID NO: 9, TUBERCULIST No. Rv1860, as
available on Mar. 1, 2007, incorporated herein
by reference, also known as Apa, modD, mpt32)

5. MLLALLRQHIRPYRRLVAMLMMLQLVSTLASLYLPTVNAAIVDD

GVAKGDTATIVRLGAVMLGVTGLQVLCAIGAVYLGSRTGAGFGRDL

RSAMFEHIITFSERETARFGAPTLLTRSTNDVRQILFLVQMTATVLVT

APIMCVGGIIMAIHQEAALTWLLLVSVPILAVANYWIISHMLPLFRRM

QSLIDGINRVMRDQLSGVRVVRAFTREGYERDKFAQANTALSNAAL

SAGNWQALMLPVTTLTINASSVALIWFGGLRIDSGQMQVGSLIAFLS

YFAQILMAVLMATMTLAVLPRASVCAERITEVLSTPAALGNPDNPKF

PTDGVTGVVRLAGATFTYPGADCPVLQDISLTARPGTTTAIVGSTGS

GKSTLVSLICRLYDVTAGAVLVDGIDVREYHTERLWSAIGLVPQRSY

LFSGTVADNLRYGGGPDQVVTEQEMWEALRVAAADGFVQTDGLQT

RVAQGGVNFSGGQRQRLAIARAVIRRPAIYVFDDAFSALDVHTDAK

VHASLRQVSGDATIIVVTQRISNAAQADQVIVVDNGKIVGTGTHETL

LADCPTYAEFAASQSLSATVGGVG
(SEQ ID NO: 10, TUBERCULIST NO. Rv1273c, as
available Mar. 1, 2007, incorporated herein
by reference).

6. MSYVIAAPEMLATTAADVDGIGSAIRAASASAAGPTTGLLAAAA

DEVSSAAAALFSEYARECQEVLKQAAAFHGEFTRALAAAGAAYAQ

AEASNTAAMSGTAGSSGALGSVGMLSGNPLTALMMGGTGEPILSDR

VLAIIDSAYIRPIFGPNNPVAQYTPEQWWPFIGNLSLDQSIAQGVTLLN

NGINAELQNGHDVVVFGYSQSAAVATNEIRALMALPPGQAPDPSRL

AFTLIGNINNPNGGVLERYVGLYLPFLDMSFNGATPPDSPYQTYMYT

GQYDGYAHNPQYPLNILSDLNAFMGIRWVHNAYPFTAAEVANAVPL

PTSPGYTGNTHYYMFLTQDLPLLQPIRAIPFVGTPIAELIQPDLRVLVD

LGYGYGYADVPTPASLFAPINPIAVASALATGTVQGPQAALVSIGLLP

QSALPNTYPYLPSANPGLMFNFGQSSVTELSVLSGALGSVARLIPPIA
(SEQ ID NO: 11, TUBERCULIST NO. Rv0159c,
available Mar. 1, 2007, incorporated herein by
reference, also know as PE3 or PE).

7. MEFPVLPPEINSVLMYSGAGSSPLLAAAAAWDGLAEELGSAAVSF

GQVTSGLTAGVWQGAAAAAMAAAAAPYAGWLGSVAAAAEAVAG

QARVVVGVFEAALAATVDPALVAANRARLVALAVSNLLGQNTPAIA

AAEAEYELMWAADVAAMAGYHSGASAAAAALPAFSPPAQALGGG

VGAFLTALFASPAKALSLNAGLGNVGNYNVGLGNVGVFNLGAGNV

GGQNLGFGNAGGTNVGFGNLGNGNVGFGNSGLGAGLAGLGNIGLG

NAGSSNYGFANLGVGNIGFGNTGTNNVGVGLTGNHLTGIGGLNSGT

GNIGLFNSGTGNVGFFNSGTGNFGVFNSGNYNTGVGNAGTASTGLF

NAGNFNTGVGNVGSYNTGSFNAGDTNTGGFNPGGVNTGWLNTGNT

NTGIANSGNVNTGAFISGNFNNGVLWVGDYQGLFGVSAGSSIPAIPIG

LVLNGDIGPITIQPIPILPTIPLSIHQTVNLGPLVVPDIVIPAFGGGIGI

-continued
PINIGPLTITPITLFAQQTFVNQLPFPTFSLGKTTIPQIQTFDSNGQLVS

FIGPIVIDTTIPGPTNPQIDLTIRWDTPPITLFPNGISAPDNPLGLLVSV

SISNPGFTIPGFSVPAQPLPLSIDIEGQIDGFSTPPITIDRIPLTVGGGV

TIGPITIQGLHIPAAPGVGNYITAPSSGFFNSGAGGVSGFGNVGAGSSGW

WNQAPSALLGAGSGVGNVGTLGSGVLNLGSGISGFYNTSVLPFGTPAAVS

GIGNLGQQLSGVSAAGTTLRSMLAGNGLANVGNFNTGFGNVGDVNL

GAANIGGHNLGLGNVGDGNLGLGNIGHGNLGFANLGLTAGAAGVG

NVGFGNAGINNYGLANMGVGNIGFANTGTGNIGIGLVGDHRTGIGG

LNSGIGNIGLFNSGTGNVGFFNSGTGNFGIGNSGRFNTGIGNSGTAST

GLFNAGSFSTGIANTGDYNTGSFNAGDTNTGGFNPGGINTGWFNTGH

ANTGLANAGTFGTGAFMTGDYSNGLLWRGGYEGLVGVRVGPTISQF

PVTVHAIGGVGPLHVAPVPVPAVHVEITDATVGLGPFTVPPISIPSLP

IASITGSVDLAANTISPIRALDPLAGSIGLFLEPFRLSDPFITIDAFQVV

AGVLFLENIIVPGLTVSGQILVTPTPIPLTLNLDTTPWTLFPNGFTIPAQ

TPVTVGMEVANDGFTFFPGGLTFPRASAGVTGLSVGLDAFTLLPDGFT

LDTVPATFDGTILIGDIPIPIIDVPAVPGFGNTTTAPSSGFFNTGGGGGS

GFANVGAGTSGWWNQGHDVLAGAGSGVANAGTLSSGVLNVGS

GISGWYNTSTLGAGTPAVVSGIGNLGQQLSGFLANGTVLNRSPIVNIG

WADVGAFNTGLGNVGDLNWGAANIGAQNLGLGNLGSGNVGFGNIG

AGNVGFANSGPAVGLAGLGNVGLSNAGSNNWGLANLGVGNIGLAN

TGTGNIGIGLVGDYQTGIGGLNSGSGNIGLFNSGTGNVGFFNTGTGNF

GLFNSGSFNTGIGNSGTGSTGLFNAGNFNTGIANPGSYNTGSFNVGDT

NTGGFNPGDINTGWFNTGIMNTGTRNTGALMSGTDSNGMLWRGDH

EGLFGLSYGITIPQFPIRITTTGGIGPIVIPDTTILPPLHLQITGDADYS

FTVPDIPIPAIHIGINGVVTVGFTAPEATLLSALKNNGSFISFGPITLSN

IDIPPMDFTLGLPVLGPITGQLGPIHLEPIVVAGIGVPLEIEPIPLDAIS

LSESIPIRIPVDIPASVIDGISMSEVVPIDASVDTPAVTITGTTISAIPL

GFDIRTSAGPLNIPIIDIPAAPGFGNSTQMPSSGFFNTGAGGGSGIGNLG

AGVSGLLNQAGAGSLVGTLSGLGNAGTLASGVLNSGTAISGLFNVSTLDA

TTPAVISGFSNLGDHMSGVSIDGLIAILTFPPAESVFDQIIDAAIAELQH

LDIGNALALGNVGGVNLGLANVGEFNLGAGNVGNINVGAGNLGGSNLGL

GNVGTGNLGFGNIGAGNFGFGNAGLTAGAGGLGNVGLGNAGS

GSWGLANVGVGNIGLANTGTGNIGIGLTGDYRTGIGGLNSGTGNLGL

FNSGTGNIGFFNTGTGNFGLFNSGSYSTGVGNAGTASTGLFNAGNFN

TGLANAGSYNTGSLNVGSFNTGGVNPGTVNTGWFNTGHTNTGLFNT

GNVNTGAFNSGSFNNGALWTGDYHGLVGFSFSIDIAGSTLLDLNETL

NLGPIHIEQIDIPGMSLFDVHEIVEIGPFTIPQVDVPAIPLEIHESIHMD

PIVLVPATTIPAQTRTIPLDIPASPGSTMTLPLISMRFEGEDWILGSTAA

IPNFGDPFPAPTQGITIHTGPGPGTTGELKISIPGFEIPQIATTRFLLDV

NISGGLPAFTLFAGGLTIPTNAIPLTIDASGALDPITIFPGGYTIDPLPL

HLALNLTVPDSSIPIIDVPPTPGFGNTTATPSSGFFNSGAGGVSGFGNVG

-continued

```
SNLSGWWNQAASALAGSGSGVLNVGTLGSGVLNVGSGVSGIYN

TSVLPLGTPAVLSGLGNVGHQLSGVSAAGTALNQIPILNIGLADVGNF

NVGFGNVGDVNLGAANLGAQNLGLGNVGTGNLGFANVGHGNIGFG

NSGLTAGAAGLGNTGFGNAGSANYGFANQGVRNIGLANTGTGNIGI

GLVGDNLTGIGGLNSGAGNIGLFNSGTGNIGFFNSGTGNFGIGNSGSF

NTGIGNSGTGSTGLFNAGSFNTGVANAGSYNTGSFNAGDTNTGGFNP

GTINTGWFNTGHTNTGIANSGNVGTGAFMSGNFSNGLLWRGDHEGL

FSLFYSLDVPRITIVDAHLDGGFGPVVLPPIPVPAVNAHLTGNVAMGA

FTIPQIDIPALTPNITGSAAFRIVVGSVRIPPVSVIVEQIINASVGAEMR

IDPFEMWTQGTNGLGITFYSFGSADGSPYATGPLVFGAGTSD

GSHLTISASSGAFTTPQLETGPITLGFQVPGSVNAITLFPGGLTFPATSL

LNLDVTAGAGGVDEPAITWPEIAASADGSVYVLASSIPLINEPPTPGIG

NSTITPSSGFFNAGAGGGSGFGNFGAGTSGWWNQAHTALAGAGSGF

ANVGTLHSGVLNLGSGVSGIYNTSTLGVGTPALVSGLGNVGHQLSG

LLSGGSAVNPVTVLNIGLANVGSHNAGFGNVGEVNLGAANLGAHNL

GFGNIGAGNLGFGNIGHGNVGVGNSGLTAGVPGLGNVGLGNAGGN

NWGLANVGVGNIGLANTGTGNIGIGLTGDYQTGIGGLNSGAGNLGL

FNSGAGNVGFFNTGTGNFGLFNSGSFNTGVGNSGTGSTGLFNAGSFN

TGVANAGSYNTGSFNVGDTNTGGFNPGSINTGWLNAGNANTGVAN

AGNVNTGAFVTGNFSNGILWRGDYQGLAGFAVGYTLPLFPAVGAD

VSGGIGPITVLPPIHIPPIPVGFAAVGGIGPIAIPDISVPSIHLGLDPAV

HVGSITVNPITVRTPPVLVSYSQGAVTSTSGPTSEIWVKPSFFPGIRIAP

SSGGGATSTQGAYFVGPISIPSGTVTFPGFTIPLDPIDIGLPVSLTIPGF

TIPGGTLIPTLPLGLALSNGIPPVDIPAIVLDRILLDLHADTTIGPINVP

IAGFGGAPGFGNSTTLPSSGFFNTGAGGGSGFSNTGAGMSGLLNAMSDPL

LGSASGFANFGTQLSGILNRGAGISGVYNTGALGVVTAAVVSGFGNVGQQ

LSGLLFTGVGP
(SEQ ID NO: 12, TUBERCULIST No. 3350c, as
available Mar. 1, 2007, herein incorporated
by reference, also known as PPE56 or PPE.
```

In a second embodiment, an Mtb polypeptide of use in the methods disclosed herein has a sequence at least 75%, 85%, 90%, 95%, 96%, 97%, 98% or 99% homologous to the amino acid sequence set forth in one of SEQ ID NOs: 1-12. For example, the polypeptide can have an amino acid sequence, at least 85%, 90%, 95%, 96%, 97%, 98% or 99% homologous to one of the amino acid sequences set forth in SEQ ID NOs: 1-12. Exemplary sequences can be obtained using computer programs that are readily available on the internet and the amino acid sequences set forth herein. In one example, the polypeptide retains a function of the Mtb protein, such as binding to an antibody that specifically binds the Mtb epitope.

Minor modifications of an Mtb polypeptide primary amino acid sequences may result in peptides which have substantially equivalent activity as compared to the unmodified counterpart polypeptide described herein. Such modifications may be deliberate, as by site-directed mutagenesis, or may be spontaneous. All of the polypeptides produced by these modifications are included herein. Thus, a specific, non-limiting example of a Mtb polypeptide is a conservative variant of the Mtb polypeptide. A table of conservative substitutions is provided herein. Substitutions of the amino acids sequence shown in SEQ ID NOs: 1-12 can be made based on this table.

Mtb polypeptides are disclosed herein that can be used to induce an immune response (immunogenic). These peptides include or consist of at least nine amino acids, such as nine to twenty amino acids consecutive amino acids of an Mtb polypeptide set forth above. Specific, non-limiting examples are twelve, eleven, ten amino acids, or nine consecutive amino acids of one of the Mtb polypeptides set forth above. In these examples, the Mtb polypeptide does not include the full-length amino acid sequences set forth as SEQ ID NOs: 1-12.

An isolated polypeptide is disclosed that includes nine to twelve consecutive amino acids from an Mtb polypeptide, wherein the isolated polypeptide comprises the amino acid sequence set forth as QTVEDEARRMW (SEQ ID NO: 13). In some embodiments, the polypeptide is nine, ten or eleven amino acids in length. In additional embodiments, the polypeptide consists of the amino acid sequence set forth as SEQ ID NO: 13. An isolated polypeptide is disclosed that includes nine to twelve consecutive amino acids from an Mtb polypeptide, wherein the isolated polypeptide comprises the amino acid sequence set forth as VSAAIAGLF (SEQ ID NO: 14). In some embodiments, the polypeptide is nine, ten or eleven amino acids in length. In additional embodiments, the polypeptide consists of the amino acid sequence set forth as SEQ ID NO: 14.

In several embodiments, the isolated Mtb polypeptide is included in a fusion protein. Thus, the fusion protein can include the Mtb polypeptide (see above) and a second heterologous moiety, such as a myc protein, an enzyme or a carrier (such as a hepatitis carrier protein or bovine serum albumin) covalently linked to the Mtb polypeptide. In several examples, a polypeptide consisting of nine to twelve amino acids of one of the amino acid sequences set forth as SEQ ID NOs: 1-14 that bind MHC class I is covalently linked to a carrier. In additional example, a polypeptide consisting of one of the amino acid sequences set forth as one of SEQ ID NOs: 1-14 is covalently linked to a carrier.

In additional examples, the polypeptide can be a fusion protein and can also include heterologous sequences to Mtb (such as amino acid sequences of at least nine amino acids in length that are not included in SEQ ID NO: 1). Thus, in several specific non-limiting examples, the immunogenic peptide is a fusion polypeptide, for example the polypeptide includes six sequential histidine residues, a β-galactosidase amino acid sequence, or an immunoglobulin amino acid sequence. The polypeptide can also be covalently linked to a carrier. Suitable carriers include, but are not limited to, a hepatitis B small envelope protein HBsAg. This protein has the capacity to self assemble into aggregates and can form viral-like particles. The preparation of HBsAg is well known, see for example European Patent Application Publication No. EP-A-0 226 846, European Patent Application Publication No. EP-A-0 299 108 and PCT Publication No. WO 01/117554, and the amino acid sequence disclosed, for example, in Tiollais et al., Nature, 317: 489, 1985, and European Patent Publication No. EP-A-0 278 940, and PCT Publication No. WO 91/14703, all of which are incorporated herein by reference.

In additional embodiments, the protein consists of the Mtb polypeptide. A second heterologous moiety can be non-covalently linked to the Mtb polypeptide. For example, a polypeptide consisting of nine to twelve consecutive amino acids of one of the proteins set forth as one of SEQ ID NO: 1-14 can be non-covalently linked to a carrier.

The polypeptide can optionally include repetitions of one or more of the Mtb polypeptides disclosed herein. In one specific, non-limiting example, the polypeptide includes two, three, four, five, or up to ten repetitions of one of the Mtb polypeptides described above. Alternatively, more than one polypeptide can be included in a fusion polypeptide. Thus, in several examples, the polypeptide can include at least two, at least three, at least four, at least five or at least six of the amino acid sequences set forth as SEQ ID NOs: 1-14. A linker sequence can optionally be included between the Mtb polypeptides.

The Mtb polypeptides disclosed herein can be chemically synthesized by standard methods, or can be produced recombinantly. An exemplary process for polypeptide production is described in Lu et al., *Federation of European Biochemical Societies Letters*. 429:31-35, 1998. They can also be isolated by methods including preparative chromatography and immunological separations.

If desired, polypeptides can also be chemically synthesized by emerging technologies. One such process is described in W. Lu et al., *Federation of European Biochemical Societies Letters*. 429:31-35, 1998. Polypeptides can also be produced using molecular genetic techniques, such as by inserting a nucleic acid encoding Mtb or an epitope thereof into an expression vector, introducing the expression vector into a host cell, and isolating the polypeptide (see below).

An Mtb polypeptide can be covalently linked to a carrier, which is an immunogenic macromolecule to which an antigenic molecule can be bound. Carriers are chosen to increase the immunogenicity of the bound molecule and/or to elicit higher titers of antibodies against the carrier which are diagnostically, analytically, and/or therapeutically beneficial. Covalent linking of a molecule to a carrier can confer enhanced immunogenicity and T cell dependence (see Pozsgay et al., *PNAS* 96:5194-97, 1999; Lee et al., *J. Immunol.* 116:1711-18, 1976; Dintzis et al., *PNAS* 73:3671-75, 1976). Useful carriers include polymeric carriers, which can be natural (for example, polysaccharides, polypeptides or proteins from bacteria or viruses), semi-synthetic or synthetic materials containing one or more functional groups to which a reactant moiety can be attached. Bacterial products and viral proteins (such as hepatitis B surface antigen and core antigen) can also be used as carriers, as well as proteins from higher organisms such as keyhole limpet hemocyanin, horseshoe crab hemocyanin, edestin, mammalian serum albumins, and mammalian immunoglobulins. Additional bacterial products for use as carriers include bacterial wall proteins and other products (for example, streptococcal or staphylococcal cell walls and lipopolysaccharide (LPS)).

Polynucleotides encoding the Mtb polypeptides disclosed herein are also provided. Exemplary nucleic acid sequences are set forth below:

```
ESXJ (ESAT-6 LIKE PROTEIN 2)
                                  (SEQ ID NO: 15)
atggcctcgcgttttatgacggatccgcacgcgatgcgggacatggcggg ccgttttgaggtgcacgcccagacggtggaggacgaggctcgccggatgt gggcgtccgcgcaaaacatctcgggcgcgggctggagtggcatggccgag gcgacctcgctagacaccatgacccagatgaatcaggcgtttcgcaacat cgtgaacatgctgcacggggtgcgtgacgggctggttcgcgacgccaaca
```

-continued

```
actacgaacagcaagagcaggcctcccagcagatcctcagcagctga

ESXK (ESAT-6 LIKE PROTEIN 3)
                                  (SEQ ID NO: 16)
atggcctcacgttttatgacggatccgcacgcgatgcgggacatggcggg ccgttttgaggtgcacgcccagacggtggaggacgaggctcgccggatgt gggcgtccgcgcaaaacatttccggtgcgggctggagtggcatggccgag gcgacctcgctagacaccatggcccagatgaatcaggcgtttcgcaacat cgtgaacatgctgcacggggtgcgtgacgggctggttcgcgacgccaaca actacgagcagcaagagcaggcctcccagcagatcctcagcagctaa ESXM (ESAT-6 LIKE PROTEIN ESXM)
                                  (SEQ ID NO: 17)
atggcctcacgttttatgacggatccgcatgcgatgcgggacatggcggg ccgttttgaggtgcacgcccagacggtggaggacgaggctcgccggatgt gggcgtccgcgcaaaacatttccggtgcgggctggagtggcatggccgag gcgacctcgctagacaccatgacctagatgaatcaggcgtttcgcaacat cgtgaacatgctgcacggggtgcgtgacgggctggttcgcgacgccaaca actacgaacagcaagagcaggcctcccagcagatcctgagcagctag ESXP (ESAT-6 LIKEK PROTEIN 7)
                                  (SEQ ID NO: 18)
atggcaacacgttttatgacggatccgcacgcgatgcgggacatggcggg ccgttttgaggtgcacgcccagacggtggaggacgaggctcgccggatgt gggcgtccgcgcaaaacatctcgggcgcgggctggagtggcatggccgag gcgacctcgctagacaccatggcccagatgaatcaggcgtttcgcaacat cgtgaacatgctgcacggggtgcgtgacgggctggttcgcgacgccaaca actacgagcagcaagagcaggcctcccagcagatcctcagcagctaa ESXW (ESAT-6 LIKE PROTEIN 10)
                                  (SEQ ID NO: 19)
atgacctcgcgttttatgacggatccgcacgcgatgcgggacatggcggg ccgttttgaggtgcacgcccagacggtggaggacgaggctcgccggatgt gggcgtccgcgcaaaacatttccggcgcgggctggagtggcatggccgag gcgacctcgctagacaccatgacccagatgaatcaggcgtttcgcaacat cgtgaacatgctgcacggggtgcgtgacgggctggttcgcgacgccaaca actacgaacagcaagagcaggcctcccagcagatcctcagcagctga PE9 (PE FAMILY PROTEIN)
                                  (SEQ ID NO: 20)
atgtcatacatgattgccacaccagcggcgttgacggcggcggcaacgga tatcgacgggattggctcggcggttagcgttgcgaacgccgcggcggtcg ccgcgacaaccggagtgctggccgccggtggcgatgaagtgttggcggcc atcgctaggctgttcaacgcaaacgccgaggaatatcacgccctcagcgc gcaggtggcggcgtttcaaaccctgtttgtgcgcaccttgactgggggt gcggagtctttcgccggcgccgaggccgccaatgcgtcacagctgcagag catcgcgcggcaggtgcggggcgccgtcaacgccgtcgccggtcaggtga cgggcaatggcggctccggcaacagcggcacttcggctgcggcggccaac ccgaattccgacaacacagcGagcatcgccgatag PE_PGRS42 (PE-PGRS FAMILY PROTEIN)
                                  (SEQ ID NO: 21)
gtgtcgttggtgatcgcgacgccgcagctgctggcaactgcggctttgga
```

-continued tttagcgagtattggttcgcaggtgagcgcggctaatgcggccgcggcga
tgccgacgacggaagtggtggctgcggctgccgatgaagtgtcggcggcg
attgcggggttgttcggggcccatgctcggcagtatcaggcgctcagcgt
acaggtggcagcgtttcacgagcagtttgtgcaggcgttgactgcggccg
cgggtcggtatgccagcactgaggccgctgttgagcggagtctgctgggt
gcggtgaatgcgccaccgaggcgcttttggggcgcccgttgatcggaaa
cggcgccgacgggacggcacccgggcagcctggcgcggccggcgggttgc
tgtttggcaacggtggcaacgcgcggctggcgggttcggtcaaaccggc
ggcagcggaggcgcggccgggttgatcggcaacggcggcaacggcgggc
cggtggtaccggcgcggccggcggtgccggtgggaacggggggtggttgt
ggggcaacggcggcaacggcggtgtcggcggcaccagcgtggccgcaggc
atcgggggtgcgggcggtaacggcggcaacgccgggctgttcggccatgg
cggcgccggtggtaccggcggcgccggcctcgccggggcaaacgggtca
atcccacgcccggccccgcggccagcaccggggacagcccggcagatgtg
tccggcatcggtgatcaaaccggcggcgacggcggcacgggcggccatgg
cactgccggcacgccgaccggtggcaccggcggcgacggtgccaccgcga
cggcaggctcgggcaaggccaccggcggtgccggtggtgacggcggtacc
gccgctgccggtggcggcggcggcaacggcgcggacggcggagtcgcgca
gggcgacattgcgagcgcctttggcggtgatggtggcaacgggtccgacg
gtgtagccgccggcagtgggggtggtagcggcggcgccggaggcggcgct
ttcgtacacatcgccactgccacctctaccggtggtagcggcggtttcgg
tggtaacggggctgccagtgccgcctccggcgccgacggtggcgcagggg
gagctggcgcaatggtggccgcgcgggttgctattcggtgatggcggc
aacggtggcgccggtggcgcgggtggtatcggtggtgacggcgccacggg
ggggcccggggggaagcggcggcaacgctggcatcgcgaggtttgacagcc
cagaccccgaggcagaacccgatgtggtcggcggcaagggtggtgatggc
ggcaagggcggcagcggccttggcgtcggcggcgccggcgggaccggcgg
cgcgggcggcaacggcggcgccggcgggttgttgttcggcaacggcggca
acggcggcaacgccggggcggcggggatggcggcgccgcgttgccggt
ggggttggcggtaacggcggcggtggtggcaccgcgacgtttcacgaaga
cccggtcgctggtgtctgggcggtcggtggcgtaggtggtgatggtggct
ccggcggcagctcgcttggtgtcggcggggtgggcggagccggtggcgtg
ggtggcaagggtggcgccagcggcatgttgatcggcaacggcggcaacgg
tggcagcggcggagtcggtggggccggtggagtcggcggggctggcggtg
acggcggcaacggcggctccggtggcaacgccagtactttggcgatgag
aactccatcggcggggccggcgggacgggcggcaacgggggcaacggcgc
aaacggcggtaacggtggcgctggcggtattgccggcggtgcgggtgggt
ccggagggttcctcagcggtgccgcaggagtcagcggcgctgacggtatc
ggtggcgcgggcggcaggcggtgccggtgcgcgggcggtagcggcg
tgaggcaggcgcgggggggcctcaccaacggccccgggtcccctggcgttt
ccggcaccgaaggcatggccggcgcgcccggctag Rv1860 (FIBRONECTIN ATTACHMENT PROTEIN)
(SEQ ID NO: 22)
atgcatcaggtggaccccaacttgacacgtcgcaagggacgattggcggc
actggctatcgcggcgatggccagcgccagcctggtgaccgttgcggtgc
ccgcgaccgccaacgccgatccggagccagcgccccggtacccacaacg
gccgcctcgccgccgtcgaccgctgcagcgccacccgcaccggcgacacc
tgttgccccccaccaccggccgccgccaacacgccgaatgcccagccgg
gcgatcccaacgcagccacctccgccgccgaccccgaacgcaccgccgcca
cctgtcattgccccaaacgcaccccaacctgtccggatcgacaaccccggt
tggaggattcagcttcgcgctgcctgctggctgggtggagtctgacgccg
cccacttcgactacggttcagcactcctcagcaaaaccaccggggacccg
ccatttcccggacagccgcgccggtggccaatgacacccgtatcgtgct
cggccggctagaccaaaagctttacgccagcgccgaagccaccgactcca
aggccgcggcccggttgggctcggacatgggtgagttctatatgccctac
ccgggcacccggatcaaccaggaaaccgtctcgctcgacgccaacggggt
gtctggaagcgcgtcgtattacgaagtcaagttcagcgatccgagtaagc
cgaacggccagatctggacgggcgtaatcggctcgcccgcggcgaacgca
ccggacgccggccccctcagcgctggtttgtggtatggctcgggaccgc
caacaacccggtggacaagggcgcggccaaggcgctggccgaatcgatcc
ggcctttggtcgccccgccgccggcgccggcaccggctcctgcagagccc
gctccggccgcggccggccggggaagtcgctcctaccccgacgacacc
gacaccgcagCggaccttaccggcctga Rv1273c (PROBABLE DRUGS-TRANSPORT TRNASMEMBRANE
ATP-BINDING PROTEIN ABC TRANSPROTER)
(SEQ ID NO: 23)
atgctcctggccctgctgcgccagcacatccgaccgtaccgccggctggt
cgcgatgctgatgatgctgcagctggtcagcaccctggcttcgctataccc
tcccgacggtcaacgccgcaatcgtcgacgacggcgtcgccaagggcgac
accgccaccatcgtacggctgggtgcggtgatgcttggggtgaccggatt
gcaggtgctgtgcgcgatcgggcggtctatctgggctcccggaccggggg
cgggttcggccgtgacctgcgctcggcaatgttcgaacacatcatcacc
ttctcggaacgcgagaccgcccgattcggcgctccgacgttgttgacccg
cagcaccaacgacgtccggcagatcctgttcctggtccagatgaccgcca
ccgtgctggtcaccgcaccgatcatgtgcgtcggcggaatcatcatggcc
atccaccaggaggccgcgctgacatggctgctgctggtcagcgttccgat
tctggccgtagcaaactactggatcatctcccacatgctgccgctcttcc
gccgcatgcagagcctgatcgacggcatcaaccgggtgatgcgcgatcag
ctgtccggggtgcgagtggtccgcgccttcacccgcgaaggctatgaacg
cgacaagttcgcgcaggccaatacggcgctgtcgaatgccgcactgagcg
ccggcaactggcaagcactgatgctgccggtgaccacgctgaccatcaac
gcatccagcgtcgcactgatctgttcggtgggctacgcatcgacagcgg
ccagatgcaggtcggctccctgatcgccttcctgtcctacttcgcccaga

```
tcctgatggcggtgttgatggcgaccatgacgctggccgtgctgccacga
gcgtcggtctgcgccgaacgcatcaccgaggtgctttccacgcccgccgc
actcggtaaccccgacaatcccaagttcccgacggacggggtcacgggcg
tagtgcgcttggctggcgcaaccttttacctatcctggcgccgactgcccg
gtgctgcaggacatttcgttgactgcgcggcccggtaccaccaccgcgat
cgtcggcagtaccggttcgggcaagtcgacactggtgtcgttgatctgcc
ggctctacgacgtcaccgctggcgcggtcttggttgacggtatcgacgtc
cgcgagtaccacaccgagcggctctggtcagcgatcgggctggtgcccca
gcgcagctacctcttctccggaaccgtcgcggacaacctgcgctacggcg
ggggcccagaccaggtagtcaccgagcaggagatgtgggaggcgctgcgg
gtcgccgcggccgacggctttgtacaaacagacgggctgcagacgcgtgt
cgcccaaggtggtgtcaacttctccggcgggcagcgccaacggctggcga
tagcccgagcggtcatccgacgtccggccatctatgtgttcgacgacgcg
ttctccgcacttgacgtgcacaccgacgccaaagtccacgcatcgctgcg
acaggtatctggtgatgcaaccatcattgttgttacacaacggatttcga
atgccgctcaggccgaccaggtcatcgttgtcgataacggtaagatcgtc
ggcacgggcacccacgaaacgctgctggccgattgccccacctatgccga
attcgccgcctcacaatcgctgagcgccacggtcgggggtGtagggtga
Rv0159c (PE FAMILY PROTEIN)
                          (SEQ ID NO: 24)
atgtcctacgtcatcgcggccccggagatgttggcaacgacggccgcgga
cgtggacgggatcggttcggcgatacgagcggccagcgcgtccgctgcgg
gtccaacgaccggactgctggccgcgccgccgatgaggtgtcgtcggcc
gctgcagcgctgttcagcgaatacgcgcgcgaatgtcaagaggtcctaaa
gcaggctgcggcgttccatggcgagttcacccgggcgctggctgccgccg
gggccgcctatgcccaggctgaagccagcaacaccgctgctatgtcgggc
accgccgggtccagcggcgccctcggttctgtcgggatgctgtcaggcaa
cccgctaaccgcgttgatgatgggcggcaccggggaaccgatccttagtg
accgcgtcttggcgatcattgacagcgcatacattcggcccattttcggg
cccaacaacccggtcgcccagtacacgcccgagcagtggtggccgtttat
cgggaacctgtcactggaccaatccatcgcccagggtgtcacgctgctga
caacgcgcatcaacgcggaactacaaaatgggcatgacgtcgtcgttttc
ggctactcgcaaagcgccgcggtagcgaccaatgaaatacgcgctcttat
ggcgttaccaccgggccaagcccccagatccaagccggctggctttcacgt
tgatcggtaatatcaataaccccaacggcggcgtcctcgagcgttacgtg
ggcctttacctcccgttcttggatatgtcgttcaacggtgcgactccacc
ggattccccctaccagacctacatgtacaccggccaatacgacggctacg
cccacaacccgcagtacccgctcaatatcttgtcggacctcaacgccttc
atgggcatcagatgggtgcacaacgcgtacccttcaccgcggccgaggt
tgccaatgccgccgttgcccacgtctccgggctacaccggcaacaccc
attactacatgtttctgacccaggacctgccgctgttgcagccgattcgc
gccatcccttcgtagggaccccaatagccgagctgattcagcccgacct
```

```
acgggtgctagtcgacttgggctatggctacggctacgccgacgtaccca
ccccggccagcctgttcgcgccaatcaacccgatcgccgtggcctcggcc
ctggcgaccgggaccgtgcaaggcccccaagccgccctagtaagcatcgg
attgttaccgcagtccgcgctacccaatacgtatccgtatcttccgtcgg
cgaatccgggcctgatgttcaacttcggtcaatccagtgtgacggagttg
tcggtgctcagtggcgccctcgggtccgtagcgagattgattccaccgat
cgcgtga
Rv3350c (PPE FAMILY PROTEIN)
                          (SEQ ID NO: 25)
atggagtttccggtgttgccaccggaaatcaactccgtgctgatgtattc
gggtgcggggtcgagcccgttgctggcggcggccgcggcgtgggatgggc
tggctgaggagttggggtcggcggcggtgtcgtttgggcaggtgacgtcg
ggcctgacggcggggtgtggcagggtgcggcggcggcggcgatggcggc
cgcggcggcgccgtatgcggggtggttgggttcggtggcggccgcggccg
aggcggtggccgggcaggcgcgggtggtggtgggggtctttgaggcggcg
ttggcggcgacggtggatccggcgctggtggcggccaaccgggcgcggct
ggtggcgttggcggtgtcgaatctgttggggcagaacacgccggcgatcg
cggccgccgaggccgagtacgagctgatgtgggccgccgatgtggcggcg
atggccggctaccattccggcgcgtcggctgctgccgcggcgttgccggc
gttcagcccaccgcgcaggcgctggggggaggtgtcggcgcgttccta
ccgccctgttcgccagccctgcgaaggcgctgagcctgaatgcgggtttg
ggcaatgtcggcaattacaacgtcggttgggcaatgtcggggtgttcaa
cctgggcgcggggcaatgtgggtgggcagaatctgggtttcgggaatgccg
gtggcaccaatgtcgggttcggcaacctcggtaacgggaatgtcgggttc
ggcaactccggtctgggggcgggcctggccggcttgggcaatatcgggtt
gggcaatgcgggcagcagcaactatggtttcgcaaacctgggtgtgggca
acatcggtttcggcaacaccggcaccaacaacgtcggcgtcgggctcacc
ggcaaccacctgacgggtatcggggggctgaattcgggcaccgggaatat
cggggttgttcaactccggcaccgggaatgtggggttcttcaattcgggga
ccgggaacttcggggtgttcaactcgggtaattacaacaccggtgtcggt
aatgcggggacggccagcacggggttgttcaatgccggcaatttcaacac
cggcgtggtgaacgtgggcagttacaacaccggcagtttcaacgccggcg
acaccaacaccggtggcttcaaccccggcggtgtgaacaccggctggctg
aacaccggcaacaccaacaccggcatcgccaactcgggcaacgtcaacac
cggcgcgttcatctcgggcaacttcaacaacggcgtgctgtgggtgggtg
actaccagggcctgttcggcgtctccgccggctcgtcgatcccgcaatt
cccatcggcctggtgctcaacggcgacatcggcccgatcaccatccagcc
catcccgatcctgcccaccatcccgctcagcattcaccaaaccgtcaact
tgggccgctggtggttcccgacatcgtgatccccgccttcggcggcgt
atcggcatacccatcaacatcggcccgctgaccatcacacccatcaccct
gtttgcccaacagacatttgtcaaccaattgcccttcccaccttcagtt
```

-continued tagggaaaatcacaattccacaaatccaaacctttgattctaacggtcag
cttgtcagctttatcggccctatcgttatcgacaccaccattcccggacc
caccaatccacagattgatttaacgatcagatgggataccctccgatca
cgctgttcccgaatggcatcagtgctcccgataatcctttggggttgctg
gtgagtgtgtcgatcagtaacccgggctttaccatcccgggatttagtgt
tcccgcgcagccgttgccgttgtcgatcgatatcgagggccagatcgacg
ggttcagcaccccgccgatcacgatcgatcgcatcccctgaccgtgggg
ggcggggtcacgatcggccccatcacgatccagggccttcatatcccggc
ggcgccgggagtggggaacaccaccacggccccgtcgtcgggattcttca
actccggtgcgggtggggtgtcgggtttcggcaacgtcggcgcgggcagc
tcgggctggtggaaccaggcgccgagcgcgctgttggggggccggttcgg
tgttggcaacgtgggcaccctgggctcgggtgtgctcaacctgggctcag
ggatctcggggttctacaacaccagcgtgttgcctttcgggacaccggcg
gcggtgtcgggcatcggcaacctgggccagcagctgtcggggggtgtcggc
ggcgggaaccacgctgcgctcgatgctcgccggcaacctcggggttggcca
atgtgggcaacttcaacacccggggttcggaaatgtcggggacgtcaacctg
ggtgcggccaacatcggtgggcacaacctgggcctgggcaatgtcgggga
cggcaacctggggtttgggcaacatcggccatggcaacctggggtttgcca
acttgggcctgaccgccggcgcggcggggggtgggcaatgttggttttggc
aatgccggcatcaacaactatggcttggcgaacatgggtgtgggcaatat
tgggttttgccaacaccggcacgggcaacatcgggatcgggctggtcgggg
accatcggaccgggatcgggggcttgaactccggcatcggcaatatcggg
ttgttcaactccggcaccggcaacgtcgggttcttcaattccggaccgg
caacttcggcatcgggaactccggccgcttcaacaccgggatcggtaata
gcggaacggccagcaccgggctcttcaatgccggcagcttcagcaccggc
atcgccaacactggtgactacaacacgggcagcttcaacgccggcgacac
caacaccggtggcttcaacccgggcggcatcaacaccggctggttcaaca
ccgggcatgccaacaccgggttggccaacgcgggcaccttcggcaccggc
gccttcatgacgggcgactacagcaacggcctgttgtggcggggcggcta
cgagggcctggtcggcgtccgcgtcgggcccacgatctcccaattcccgg
tcaccgtgcacgcgatcggcggggtgggcccgctgcatgtggcgcccgtc
ccggtacccgccgtgcacgtcgagatcaccgacgccaccgtcggcctggg
tccgttcaccgtcccaccgatcagcattcctcacttcccatcgccagca
tcaccggaagcgtggacctggccgcaaacaccatctcgccgattcgcgct
cttgacccgctcgccggttcgatagggcttttctcgagccgttccgcct
cagtgacccatttatcaccattgatgcgttccaagttgttgccggtgtct
tgttcctagagaacatcattgtgcccggcctcacggttagcggtcagata
ttggtcaccccgacaccaattcccctaaccctcaacttggacaccacccc
gtggacgcttttcccgaatggtttcaccattcccgcgcaaaccccgtga
cggtgggtatggaggtcgccaacgacgggttcaccttcttcccgggtggg
ctgacctttccgcgggcctccgccggggtcaccggactgtccgtgggct -continued ggacgcgttcacgctgttgcccgacgggttcaccctcgacaccgtgccgg
cgaccttcgacggcaccatcctcatcggcgatatcccgatcccgatcatc
gatgtgccggcggtgccggggttcggcaacaccaccacggcccccatcgtc
ggggttcttcaacaccggcggcggcggtggatcggggttcgccaacgtcg
gcgcgggcacgtcgggctggtggaaccaggggcacgacgtgttagcaggg
gcgggctcgggagttgccaatgccggcacgctgagctcgggcgtgctgaa
cgtcggctcggggatctccgggtggtacaacaccagcaccctgggagcgg
gcacccgcgtggtctcgggcatcggcaacctcggccagcagctgtcg
gggttcttggcaaatgggaccgtgctcaaccggagcccattgtcaatat
cgggtgggccgatgtgggcgcgttcaacaccgggttgggcaatgtggggg
acctcaactgggggtgcggccaacatcggcgcgcagaacctgggcctgggc
aatctcggcagcgggaacgtcgggttcggcaacatcggtgccggcaacgt
cgggttcgccaactcgggtccggcggtgggcctggccggcctgggcaacg
tggggttgagcaatgccggcagcaacaactgggggctggccaacctgggt
gtgggcaacatcggggttggccaacaccggcacgggcaacatcgggatcgg
gctggtcggcgactaccagaccggcatcggcggcctcaactcgggtagtg
gcaatatcggattgttcaattccggcaccggcaatgtcgggttcttcaac
accggcaccggcaacttcggactgttcaactccggtagtttcaacaccgg
catcggtaatagcggaaccggcagtactgggctcttcaatgccggcaatt
caacaccggcatcgccaaccccgggtcgtacaacacgggcagcttcaat
gtcggtgataccaacaccggtggttttcaacccgggcgacatcaacaccgg
ctggttcaacaccggcattatgaatacgggcacccgcaacaccggcgccc
tcatgtcggggaccgacagcaacggcatgctgtggcgcggcgaccacgag
ggcctgttcggcctgtcctatggcatcacgatcccgcaattcccgatccg
catcaccacgactggcggtatcggccccatcgtcatcccggacaccacga
tccttccgccgctgcacctgcagatcaccggcgacgcggactacagcttc
accgtgcccgacatccccatccccgccatccacatcggcatcaatggcgt
cgtcaccgtcggcttcaccgccccggaagccaccctgctgtccgccctga
agaataacggtagcttcatcagcttcggccccatcacgcgctctcgaatatc
gatattccgcccatggatttcacgttaggcctgcccgttcttggtcctat
cacgggccaactcggaccaattcatcttgagccaatcgtggtggccggga
tcggtgtgcccctggagatcgagcccatcccctggatgcgatttcgttg
agtgagtcgattcctatccgcataccttgtgatattccggcctcggtcat
cgatgggattttcaatgtcggaagtggtgccgatcgatgcgtccgtggaca
tcccggcggtcacgatcacaggcaccaccatttccgcgatcccgctgggc
ttcgacattcgcaccagtgccggacccctcaacatcccgatcatcgacat
cccggcggcgccgggcttcgggaactcgacccagatgccgtcgtcggggt
tcttcaacaccggtgccggcggcggatcgggcatcggcaacttgggtgcg
ggcgtgtcgggcctgctcaaccaggccggcgcggggtcactggtggggac
actctcggggctgggcaatgccggcaccctggcctcgggtgtgctgaact -continued ccggcaccgccatctccgggctgttcaacgtgagcacgctggacgccacc
accccggcggtgatctcggggttcagcaacctcggcgaccatatgtcggg
ggtgtccatcgatggcctgatcgcgatcctcaccttcccacctgccgagt
ccgtgttcgatcagatcatcgacgcggccatcgccgagctgcagcacctc
gacatcggcaacgctttggccttgggcaatgtcggcggggtgaacctcgg
tttggctaacgtcggtgagttcaacctgggtgcgggcaacgtcggcaaca
tcaacgtcggcgccggcaacctcggcggcagcaacttgggggttgggcaac
gtcgggaccggcaacctcgggttcggcaacatcggtgccggcaatttcgg
attcggcaacgcgggcctgaccgcgggcgcggggggcctgggcaatgtgg
ggttgggtaacgccggcagcggcagctgggggttggccaacgtgggtgtg
ggcaatatcgggttggccaacaccggcaccggcaacatcgggatcgggct
gaccggggactatcggaccgggatcggcggcctgaactcgggcaccggga
acctcggggttgttcaactcgggcaccggcaacatcggttcttcaacacc
gggaccgggaacttcgggctgttcaactcgggcagttacagcaccggtgt
ggggaatgcgggcacggccagcaccgggttgttcaacgcggggaacttca
acaccggtctggccaatgccggctcctacaacaccggcagcctcaacgtg
ggcagcttcaacaccggcgcgtcaacccgggcaccgtcaacaccggctg
gttcaacaccggccacaccaacaccggcctgttcaacaccggcaacgtca
acaccggcgcgttcaactccggcagcttcaacaacggggcgctgtggacc
ggtgactaccacgggctggtcggcttctccttcagcatcgacatcgccgg
cagcaccctgctggacctcaacgaaaaccctcaacctgggcccatccaca
tcgagcagatcgacatccccggcatgtcgctgttcgacgtccacgaaatc
gtcgagatcggaccccttcaccatcccgcaggtcgatgttcccgcgatacc
gctagagatccacgaatcgatccacatggatcccatcgtcctggtgcccg
ccaccacaattcccgcacagacgagaaccattccgctggacatccccgcc
tcacccgggtcaaccatgacgcttccgctcatcagcatgcgcttcgaagg
cgaggactggatcctcgggtcgaccgcggcgattcccaatttcggagacc
ccttcccggcgcccacccagggcatcaccattcacaccggccctggcccc
ggaacgaccggcgagctcaagatatctattccggggtttcgagattccgca
aatcgctaccacgagattcctgttggacgtgaacatcagcggtggtctgc
cggccttcaccttgttcgcgggtggcctgacgatccccacgaacgccatc
ccgttaacgatcgatgcgtccggcgcgctggatccgatcacgattttccc
gggtggggtacacgatcgacccgctgccgctgcacctggcgctgaatctca
ccgtgcccgacagcagcatcccgatcatcgatgtcccgccgacgccaggg
ttcggcaacaccacggcgacccgtcgtcggggttcttcaactccggcgc
cggtggggtgtcggggttcggaaacgtcgggtcgaacctgtcgggctggt
ggaaccaggcggcgagcgcgctggcggggtcgggatcggggtgttgaat
gtcggcacgctgggctcgggtgtgctcaacgtcggctcgggtgtctcggg
gatctacaacaccagcgtgttgccgctcggggacgccggcggtgctgtcgg
gcctcggcaacgtcggccatcagctgtcgggcgtgtctgcggccgggacc
gcgttgaaccagatccccatcctcaacatcggggttggcggatgtgggcaa -continued cttcaacgtcgggttcggcaacgtcggggacgttaacctgggcgcggcca
acctcggtgcgcaaaacctggggctgggcaacgtcggcaccggcaacctc
ggcttcgccaacgtcggccacggcaatatcggtttcggcaattcgggtct
gaccgccggcgcggccggcctgggcaacacggggttcggcaatgccggca
gcgccaactatggtttcgccaaccagggcgtgcgcaacatcgggttggcc
aacaccggcaccggcaacatcgggatcgggctggtggggacaacctcac
cggcatcggggcctgaactccggtgccggcaatatcggcttgttcaact
ccggcaccggcaacatcggttcttcaactccgggaccggcaacttcggc
atcggtaactcgggcagcttcaacaccggcatcggcaatagcggaacggg
cagcactgggctcttcaatgccggcagcttcaacaccggcgtggccaacg
ccggcagctacaacaccggcagcttcaatgccggcgacaccaacaccggg
gggttcaacccggcaccatcaacaccggctggttcaacaccggccacac
caataccggcatcgccaactcgggcaacgtcggcaccggcgcgttcatgt
cgggcaacttcagcaacgcctgttgtggcggggtgatcacgagggcctg
ttcagcctgttctacagcctcgacgtgccccggatcaccatcgtggacgc
ccacctcgacggcggcttcggacccgtggtcctcccgcccatcccggtgc
cggccgttaatgcgcacctgaccggaaacgtcgcgatgggcgcattcacc
attccgcagatcgacatccccgcactcaccccaaacatcaccggaagcgc
cgccttccgcatcgttgtggggtccgtgcgcattccgccggtgagtgtca
ttgtggagcaaataatcaacgcctcggttggggcggagatgaggatagat
cccttcgaaatgtggactcaaggcactaatggccttggtataaccttcta
ttcattcggatcggccgacggttcgccctacgccaccggcccactcgttt
tcggcgccggcacgagcgacggaagccatctcaccatttccgcgtccagc
ggggcgtttaccactccgcagctcgaaactggcccgatcacgttgggctt
ccaggtgcccggcagcgtcaacgcgatcaccctcttccccggtggtttga
cgttcccggcgacctcgctgctgaacctggacgtgaccgccggcgccggc
ggcgtggacatcccggccatcacctggcccgagatcgcggcgagcgccga
cggctcggtgtatgtcctcgccagcagcatcccgctgatcaacatcccgc
ccaccccgggcattgggaacagcaccatcaccccgtcgtcgggcttcttc
aacgccggcgcggggcggggatcgggcttcggcaacttcggcgcgggcac
ctcgggctggtggaaccaggcgcacaccgcgctggcggggcgggctcgg
gtttttgccaacgttggcacgctgcattccggtgtgctcaacctgggctcg
ggtgtctcggggatctacaacaccagcacgctgggggtggggaccccggc
gctggtctcaggcctgggcaacgtcggccaccaactgtcggggctgcttt
ccggcgggtccgcggtgaacccggtgaccgttctgaatatcgggttggcc
aacgtcggcagccacaacgccggtttcggcaatgtcggggaggtcaacct
gggcgcggccaacctcggcgcgcacaacctgggcttcggaaatatcggcg
ccggcaacctgggggttcggcaatattggccacgcaatgtcggagtcggc
aactcgggtctgaccgcgggcgtgccgggcctgggcaatgtggggttggg
caatgccggcggcaacaactgggggttggccaacgtgggcgtgggcaata -continued

```
tcgggttggccaacaccggcaccggcaacattgggatcgggctgaccggc gactaccagaccggcatcggcggcctaaattccggtgccggcaacctggg gttgttcaactccggcgccggcaacgtcgggttcttcaacaccgggaccg gcaacttcgggttgttcaactccggcagcttcaacaccggcgtcggcaat agcggaacgggcagcactgggctcttcaatgccggcagtttcaacaccgg tgtggccaacgccggcagctacaacacgggcagcttcaatgtcggtgaca ccaacaccgggggcttcaacccgggcagcatcaacaccggctggctcaac gccggcaacgccaacaccggggtggccaacgcgggcaatgtcaacaccgg cgccttcgtcaccggcaacttcagcaacggcatcctgtggcgcggcgact accagggcctggccggcttcgccgtgggctacaccctcccgctgttcccc gcggtgggcgccgacgtcagcggcgggatcggcccgattaccgtgctgcc gcccatccacatcccgcccattccggtcggcttcgccgcggtcggtggca tcggcccgatcgccatcccggacatctctgttccatccattcacttgggc ctcgaccccgccgtccatgtcggctccatcaccgtcaaccccattaccgt caggaccccgcccgtgctcgtcagttactcccaaggagccgtcaccagca cgtccggaccaacctcagagatttgggtcaagcccagcttcttccccgga atccggatcgcgccctctagcggcgggggtgcaacgtccacgcaaggggc atactttgtggggcccatctccatcccctccggcacggtgaccttcccgg gattcaccatcccccctcgacccgatcgacatcggcctgccggtgtcgctg accatcccggggttcaccatcccgggcggcaccctgatccccaccctccc gctgggcctcgcgttgtccaatggcatcccgcccgtcgacatcccggcca tcgttctcgaccggatcttgctggacctgcacgccgacaccactatcggc ccgatcaacgtcccgatcgccgggttcggcggggcgccgggtttcgggaa ctcgaccacgctgccgtcgtcgggcttcttcaacaccggagctggcggcg gttcgggctttagcaacaccggcgcgggcatgtcgggattgctcaacgcg atgtcggatccgctgctcgggtcggcgtcgggcttcgccaacttcggcac ccagctctecggcatcctcaaccgcggcgccggcatctcgggcgtgtaca acaccggcgcgctgggtgttgtcaccgcggccgtcgtctcgggtttcggc aacgtcggccagcaactgtcgggcttgctcttcaccggcgtcgggcccta a
```

These polynucleotides include DNA, cDNA and RNA sequences which encode the polypeptide of interest. Silent mutations in the coding sequence result from the degeneracy (i.e., redundancy) of the genetic code, whereby more than one codon can encode the same amino acid residue. Thus, for example, leucine can be encoded by CTT, CTC, CTA, CTG, TTA, or TTG; serine can be encoded by TCT, TCC, TCA, TCG, AGT, or AGC; asparagine can be encoded by AAT or AAC; aspartic acid can be encoded by GAT or GAC; cysteine can be encoded by TGT or TGC; alanine can be encoded by GCT, GCC, GCA, or GCG; glutamine can be encoded by CAA or CAG; tyrosine can be encoded by TAT or TAC; and isoleucine can be encoded by ATT, ATC, or ATA. Tables showing the standard genetic code can be found in various sources (e.g., L. Stryer, 1988, Biochemistry, 3.sup.rd Edition, W.H. 5 Freeman and Co., NY).

A nucleic acid encoding a Mtb polypeptide can be cloned or amplified by in vitro methods, such as the polymerase chain reaction (PCR), the ligase chain reaction (LCR), the transcription-based amplification system (TAS), the self-sustained sequence replication system (3SR) and the Qβ replicase amplification system (QB). For example, a polynucleotide encoding the protein can be isolated by polymerase chain reaction of cDNA using primers based on the DNA sequence of the molecule. A wide variety of cloning and in vitro amplification methodologies are well known to persons skilled in the art. PCR methods are described in, for example, U.S. Pat. No. 4,683,195; Mullis et al., *Cold Spring Harbor Symp. Quant. Biol.* 51:263, 1987; and Erlich, ed., *PCR Technology*, (Stockton Press, NY, 1989). Polynucleotides also can be isolated by screening genomic or cDNA libraries with probes selected from the sequences of the desired polynucleotide under stringent hybridization conditions.

The polynucleotides encoding a Mtb polypeptide include a recombinant DNA which is incorporated into a vector, into an autonomously replicating plasmid or virus, or into the genomic DNA of a prokaryote or eukaryote, or which exists as a separate molecule (such as a cDNA) independent of other sequences. The nucleotides of the invention can be ribonucleotides, deoxyribonucleotides, or modified forms of either nucleotide. The term includes single and double forms of DNA.

In one embodiment, vectors are used for expression in yeast such as *S. cerevisiae* or *Kluyveromyces lactis*. Several promoters are known to be of use in yeast expression systems such as the constitutive promoters plasma membrane $H^+$-ATPase (PMA1), glyceraldehyde-3-phosphate dehydrogenase (GPD), phosphoglycerate kinase-1 (PGK1), alcohol dehydrogenase-1 (ADH1), and pleiotropic drug-resistant pump (PDR5). In addition, may inducible promoters are of use, such as GAL1-10 (induced by galactose), PHO5 (induced by low extracellular inorganic phosphate), and tandem heat shock HSE elements (induced by temperature elevation to 37° C.). Promoters that direct variable expression in response to a titratable inducer include the methionine-responsive MET3 and MET25 promoters and copper-dependent CUP1 promoters. Any of these promoters may be cloned into multicopy (20 or single copy (CEN) plasmids to give an additional level of control in expression level. The plasmids can include nutritional markers (such as URA3, ADE3, HIS1, and others) for selection in yeast and antibiotic resistance (AMP) for propagation in bacteria. Plasmids for expression on *K. lactis* are known, such as pKLAC1. Thus, in one example, after amplification in bacteria, plasmids can be introduced into the corresponding yeast auxotrophs by methods similar to bacterial transformation.

The Mtb polypeptides can be expressed in a variety of yeast strains. For example, seven pleiotropic drug-resistant transporters, YOR1, SNQ2, PDR5, YCF1, PDR10, PDR11, and PDR15, together with their activating transcription factors, PDR1 and PDR3, have been simultaneously deleted in yeast host cells, rendering the resultant strain sensitive to drugs. Yeast strains with altered lipid composition of the plasma membrane, such as the erg6 mutant defective in ergosterol biosynthesis, can also be utilized. Proteins that are highly sensitive to proteolysis can be expressed in a yeast lacking the master vacuolar endopeptidase Pep4, which controls the activation of other vacuolar hydrolases. Heterologous expression in strains carrying temperature-sensitive (ts) alleles of genes can be employed if the corresponding null mutant is inviable.

Viral vectors can also be prepared encoding the Mtb polypeptides disclosed herein. A number of viral vectors have been constructed, including polyoma, SV40 (Madzak et al., 1992, J. Gen. Virol., 73:15331536), adenovirus (Berkner, 1992, Cur. Top. Microbiol. Immunol., 158:39-6; Berliner et al., 1988, Bio Techniques, 6:616-629; Gorziglia et al., 1992, J. Virol., 66:4407-4412; Quantin et al., 1992, Proc. Nad. Acad. Sci. USA, 89:2581-2584; Rosenfeld et al., 1992, Cell, 68:143-155; Wilkinson et al., 1992, Nucl. Acids Res., 20:2233-2239; Stratford-Perricaudet et al., 1990, Hum. Gene Ther., 1:241-256), vaccinia virus (Mackett et al., 1992, Biotechnology, 24:495-499), adeno-associated virus (Muzyczka, 1992, Curr. Top. Microbiol. Immunol., 158:91-123; On et al., 1990, Gene, 89:279-282), herpes viruses including HSV and EBV (Margolskee, 1992, Curr. Top. Microbiol. Immunol., 158:67-90; Johnson et al., 1992, J. Virol., 66:29522965; Fink et al., 1992, Hum. Gene Ther. 3:11-19; Breakfield et al., 1987, Mol. Neurobiol., 1:337-371; Fresse et al., 1990, Biochem. Pharmacol., 40:2189-2199), Sindbis viruses (H. Herweijer et al., 1995, Human Gene Therapy 6:1161-1167; U.S. Pat. Nos. 5,091,309 and 5,2217,879), alphaviruses (S. Schlesinger, 1993, Trends Biotechnol. 11:18-22; I. Frolov et al., 1996, Proc. Natl. Acad. Sci. USA 93:11371-11377) and retroviruses of avian (Brandyopadhyay et al., 1984, Mol. Cell. Biol., 4:749-754; Petropouplos et al., 1992, J. Virol., 66:3391-3397), murine (Miller, 1992, Curr. Top. Microbiol. Immunol., 158:1-24; Miller et al., 1985, Mol. Cell. Biol., 5:431-437; Sorge et al., 1984, Mol. Cell. Biol., 4:1730-1737; Mann et al., 1985, J. Virol., 54:401-407), and human origin (Page et al., 1990, J. Virol., 64:5370-5276; Buchschalcher et al., 1992, J. Virol., 66:2731-2739). Baculovirus (*Autographa californica* multinuclear polyhedrosis virus; AcMNPV) vectors are also known in the art, and may be obtained from commercial sources (such as PharMingen, San Diego, Calif.; Protein Sciences Corp., Meriden, Conn.; Stratagene, La Jolla, Calif.).

Thus, in one embodiment, the polynucleotide encoding an Mtb polypeptide is included in a viral vector. Suitable vectors include retrovirus vectors, *orthopox* vectors, avipox vectors, fowlpox vectors, capripox vectors, suipox vectors, adenoviral vectors, herpes virus vectors, alpha virus vectors, baculovirus vectors, Sindbis virus vectors, vaccinia virus vectors and poliovirus vectors. Specific exemplary vectors are poxvirus vectors such as vaccinia virus, fowlpox virus and a highly attenuated vaccinia virus (MVA), adenovirus, baculovirus and the like.

Pox viruses useful in practicing the present methods include orthopox, suipox, avipox, and capripox virus. Orthopox include vaccinia, ectromelia, and raccoon pox. One example of an orthopox of use is vaccinia. Avipox includes fowlpox, canary pox and pigeon pox. Capripox include goatpox and sheeppox. In one example, the suipox is swinepox. Examples of pox viral vectors for expression as described for example, in U.S. Pat. No. 6,165,460, which is incorporated herein by reference. Other viral vectors that can be used include other DNA viruses such as herpes virus and adenoviruses, and RNA viruses such as retroviruses and polio.

In some cases, vaccinia viral vectors may elicit a strong antibody response. Thus, while numerous boosts with vaccinia vectors are possible, its repeated use may not be useful in certain instances. However, this sensitivity problem can be minimized by using pox from different genera for boosts. In one example, when the first or initial pox virus vector is vaccinia, the second and subsequent pox virus vectors are selected from the pox viruses from a different genus such as suipox, avipox, capripox or an orthopox immunogenically distinct from vaccinia.

The vaccinia virus genome is known in the art. It is composed of a HIND F13L region, TK region, and an HA region. Recombinant vaccinia virus has been used to incorporate an exogenous gene for expression of the exogenous gene product (see, for example, Perkus et al. *Science* 229:981-984, 1985; Kaufman et al. *Int. J. Cancer* 48:900-907, 1991; Moss *Science* 252:1662, 1991). A gene encoding an antigen of interest, such as an immunogenic Mtb polypeptide, can be incorporated into the HIND F13L region or alternatively incorporated into the TK region of recombinant vaccinia virus vector (or other nonessential regions of the vaccinia virus genome). Baxby and Paoletti (*Vaccine* 10:8-9, 1992) disclose the construction and use as a vector, of the non-replicating poxvirus, including canarypox virus, fowlpox virus and other avian species. Sutter and Moss (*Proc. Nat'l. Acad. Sci. U.S.A.* 89:10847-10851, 1992) and Sutter et al. (*Virology* 1994) disclose the construction and use as a vector, the non-replicating recombinant Ankara virus (MVA, modified vaccinia Ankara) in the construction and use of a vector.

Suitable vectors are disclosed, for example, in U.S. Pat. No. 6,998,252, which is incorporated herein by reference. In one example, a recombinant poxvirus, such as a recombinant vaccinia virus is synthetically modified by insertion of a chimeric gene containing vaccinia regulatory sequences or DNA sequences functionally equivalent thereto flanking DNA sequences which in nature are not contiguous with the flanking vaccinia regulatory DNA sequences that encode a Mtb polypeptide. The recombinant virus containing such a chimeric gene is effective at expressing the Mtb polypeptide. In one example, the vaccine viral vector comprises (A) a segment comprised of (i) a first DNA sequence encoding a Mtb polypeptide and (ii) a poxvirus promoter, wherein the poxvirus promoter is adjacent to and exerts transcriptional control over the DNA sequence encoding an Mtb polypeptide; and, flanking said segment, (B) DNA from a nonessential region of a poxvirus genome. The viral vector can encode a selectable marker. In one example, the poxvirus includes, for example, a thymidine kinase gene (see U.S. Pat. No. 6,998,252, which is incorporated herein by reference).

Viral vectors, such as poxviral vectors, that encode an Mtb polypeptide include at least one expression control element operationally linked to the nucleic acid sequence encoding the Mtb polypeptide. The expression control elements are inserted in the viral vector to control and regulate the expression of the nucleic acid sequence. Examples of expression control elements of use in these vectors includes, but is not limited to, lac system, operator and promoter regions of phage lambda, yeast promoters and promoters derived from polyoma, adenovirus, retrovirus or SV40. Additional operational elements include, but are not limited to, leader sequence, termination codons, polyadenylation signals and any other sequences necessary for the appropriate transcription and subsequent translation of the nucleic acid sequence encoding the Mtb polypeptide in the host system. The expression vector can contain additional elements necessary for the transfer and subsequent replication of the expression vector containing the nucleic acid sequence in the host system. Examples of such elements include, but are not limited to, origins of replication and selectable markers. It will further be understood by one skilled in the art that such vectors are easily constructed using conventional methods (Ausubel et al., (1987) in "Current Protocols in Molecular Biology," John Wiley and Sons, New York, N.Y.) and are commercially available.

Basic techniques for preparing recombinant DNA viruses containing a heterologous DNA sequence encoding the one or more Mtb polypeptides are known in the art. Such techniques involve, for example, homologous recombination between the viral DNA sequences flanking the DNA sequence in a donor plasmid and homologous sequences present in the parental virus (Mackett et al., 1982, Proc. Natl. Acad. Sci. USA 79:7415-7419). In particular, recombinant viral vectors such as a poxyviral vector can be used in delivering the gene.

The vector can be constructed for example by steps known in the art, such as steps analogous to the methods for creating synthetic recombinants of the fowlpox virus described in U.S. Pat. No. 5,093,258, incorporated herein by reference. Other techniques include using a unique restriction endonuclease site that is naturally present or artificially inserted in the parental viral vector to insert the heterologous DNA.

Generally, a DNA donor vector contains the following elements: (i) a prokaryotic origin of replication, so that the vector may be amplified in a prokaryotic host; (ii) a gene encoding a marker which allows selection of prokaryotic host cells that contain the vector (e.g., a gene encoding antibiotic resistance); (iii) at least one DNA sequence encoding the one or more Mtb polypeptide located adjacent to a transcriptional promoter capable of directing the expression of the sequence; and (iv) DNA sequences homologous to the region of the parent virus genome where the foreign gene(s) will be inserted, flanking the construct of element (iii). Methods for constructing donor plasmids for the introduction of multiple foreign genes into pox virus are described in PCT Publication No. WO 91/19803, incorporated herein by reference.

Generally, DNA fragments for construction of the donor vector, including fragments containing transcriptional promoters and fragments containing sequences homologous to the region of the parent virus genome into which foreign DNA sequences are to be inserted, can be obtained from genomic DNA or cloned DNA fragments. The donor plasmids can be mono, di-, or multivalent (i.e., can contain one or more inserted foreign DNA sequences). The donor vector can contain an additional gene that encodes a marker that will allow identification of recombinant viruses containing inserted foreign DNA. Several types of marker genes can be used to permit the identification and isolation of recombinant viruses. These include genes that encode antibiotic or chemical resistance (e.g., see Spyropoulos et al., 1988, J. Virol. 62:1046; Falkner and Moss, 1988, J. Virol. 62:1849; Franke et al., 1985, Mol. Cell. Biol. 5:1918), as well as genes such as the *E. coli* lacZ gene, that permit identification of recombinant viral plaques by colorimetric assay (Panicali et al., 1986, Gene 47:193-199).

The DNA gene sequence to be inserted into the virus can be placed into a donor plasmid, such as an *E. coli* or a *Salmonella* plasmid construct, into which DNA homologous to a section of DNA such as that of the insertion site of the poxvirus where the DNA is to be inserted has been inserted. Separately the DNA gene sequence to be inserted is ligated to a promoter. The promoter-gene linkage is positioned in the plasmid construct so that the promoter-gene linkage is flanked on both ends by DNA homologous to a DNA sequence flanking a region of pox DNA that is the desired insertion region. With a parental pox viral vector, a pox promoter is used. The resulting plasmid construct is then amplified by growth within *E. coli* bacteria and isolated. Next, the isolated plasmid containing the DNA gene sequence to be inserted is transfected into a cell culture, for example chick embryo fibroblasts, along with the parental virus, for example poxvirus. Recombination between homologous pox DNA in the plasmid and the viral genome respectively results in a recombinant poxvirus modified by the presence of the promoter-gene construct in its genome, at a site that does not affect virus viability.

As noted above, the DNA sequence is inserted into a region (insertion region) in the virus that does not affect virus viability of the resultant recombinant virus. One of skill in the art can readily identify such regions in a virus by, for example, randomly testing segments of virus DNA for regions that allow recombinant formation without seriously affecting virus viability of the recombinant. One region that can readily be used and is present in many viruses is the thymidine kinase (TK) gene. The TK gene has been found in all pox virus genomes examined, including leporipoxvirus (Upton et al., 1986, J. Virology 60:920); shope fibromavirus; capripoxvirus (Gershon et al., 1989, J. Gen. Virol. 70:525) Kenya sheep-1; orthopoxvirus (Weir et al., 1983, J. Virol. 46:530) vaccinia (Esposito et al., 1984, Virology 135:561); monkeypox and variola virus (Hruby et al., 1983, PNAS 80:3411) vaccinia (Kilpatrick et al., 1985, Virology 143:399); Yaba monkey tumor virus; avipoxvirus (Binns et al., 1988, J. Gen. Virol. 69:1275); fowipox; (Boyle et al., 1987, Virology 156:355); fowlpox (Schnitzlein et al., 1988, J. Virological Methods 20:341); fowlpox, quailpox; entomopox (Lytvyn et al., 1992, J. Gen. Virol. 73:3235-3240). In vaccinia, in addition to the TK region, other insertion regions include, for example, the Hind111 M fragment. In fowlpox, in addition to the TK region, other insertion regions include, for example, the BamHI J fragment (Jenkins et al., 1991, AIDS Research and Human Retroviruses 7:991-998) the EcoRI-Hind111 fragment, EcoRV-HindIII fragment, BamHI fragment and the Hind111 fragment set forth in EPO Application No. 0 308220 A1 (see also Calvert et al., 1993, J. Virol. 67:3069-3076; Taylor et al., 1988, Vaccine 6:497-503; Spehner et al., 1990; Boursnell et al., 1990, J. Gen. Virol. 71:621-628).

In swinepox, insertion sites include the thymidine kinase gene region. In addition to the requirement that the gene be inserted into an insertion region, successful expression of the inserted gene by the modified poxvirus requires the presence of a promoter operably linked to the desired gene. Generally, the promoter is placed so that it is located upstream from the gene to be expressed. Promoters are well known in the art and can readily be selected depending on the host and the cell type you wish to target. In one example, in poxviruses, pox viral promoters are used, such as the vaccinia 7.5K, 40K or fowlpox promoters such as FPV C1A. Enhancer elements can also be used in combination to increase the level of expression. Furthermore, inducible promoters can be utilized.

Homologous recombination between donor plasmid DNA and viral DNA in an infected cell can result in the formation of recombinant viruses that incorporate the desired elements. Appropriate host cells for in vivo recombination are generally eukaryotic cells that can be infected by the virus and transfected by the plasmid vector. Examples of such cells suitable for use with a pox virus are chick embryo fibroblasts, HuTK143 (human) cells, and CV-1 and BSC-40 (both monkey kidney) cells. Infection of cells with pox virus and transfection of these cells with plasmid vectors is accomplished by techniques standard in the art (see U.S. Pat. No. 4,603,112 and PCT Publication No. WO 89/03429).

Following in vivo recombination, recombinant viral progeny can be identified by one of several techniques. For example, if the DNA donor vector is designed to insert foreign genes into the parent virus thymidine kinase (TK) gene, viruses containing integrated DNA will be TK- and can be selected on this basis (Mackett et al., 1982, Proc. Natl. Acad. Sci. USA 79:7415). Alternatively, co-integration of a gene encoding a marker or indicator gene with the foreign gene(s) of interest, as described above, can be used to identify recombinant progeny. One specific non-limiting example of an indicator gene is the *E. coli* lacZ gene. Recombinant viruses expressing beta-galactosidase can be selected using a chromogenic substrate for the enzyme (Panicali et al., 1986, Gene 47:193). Once a recombinant virus has been identified, a variety of well-known methods can be used to assay the expression of the Mtb sequence encoded by the inserted DNA fragment. These methods include black plaque assay (an in situ enzyme immunoassay performed on viral plaques), Western blot analysis, radioimmunoprecipitation (RIPA), and enzyme immunoassay (EIA).

This disclosure encompasses a recombinant virus comprising more than one antigen of interest for the purpose of having a multivalent vaccine. For example, the recombinant virus may comprise the virus genome or portions thereof, the nucleic acid sequence encoding the Mtb polypeptide and a nucleic acid sequence encoding a hepatitis B surface antigen or any other carrier protein.

In one embodiment, a composition is provided that includes a recombinant virus comprising a vaccinia virus genome or portions thereof, the nucleic acid sequence encoding an Mtb polypeptide and a recombinant virus comprising the nucleic acid sequence encoding the immunostimulatory molecule, B 7.1 alone or in combination with the nucleic acid sequence encoding the immunostimulatory molecule, B7-2, or a recombinant virus containing both the genes for an Mtb polypeptide and an immunostimulatory molecule. This disclosure also encompasses a recombinant virus comprising the Mtb polypeptide that is administered with a second recombinant virus comprising the virus genome or portion thereof, and one or more nucleic acid sequences encoding one or more B7 molecules, such as a recombinant vaccinia virus expressing B7-1 and/or B7-2.

Thus, in one example, recombinant virus is disclosed that is a recombinant vaccinia virus containing B7-1 and a recombinant vaccinia virus containing B7-2 (designated rV-B7-1 and rV-B7-2, respectively); the composition can include rV-B7-1 and/or rV-B7-2 in combination with an immunogenic Mtb polypeptide.

The B7 molecule includes but is not limited to B7-1, B7-2 and analogs thereof. The B7 gene may be cloned from mammalian sources, including but not limited to mammalian tissues, genomic libraries or cDNA libraries, such as from murine or human sources. Without being bound by theory, co-stimulatory molecules of the B7 family (namely B7-1, B7-2, and possibly B7.3) are believed to be members of the immunoglobulin gene superfamily. These molecules are present on macrophages, dendritic cells, monocytes (antigen presenting cells (APCs)). Significant amplification of the immune response against a given antigen generally does not occur without co-stimulation (June et al. (*Immunology Today* 15:321-331, 1994); Chen et al. (*Immunology Today* 14:483-486); Townsend et al. (*Science* 259:368-370)). Freeman et al. (*J. Immunol.* 143:2714-2722, 1989) report cloning and sequencing of B7-1 gene. Azuma et al. (Nature 366:76-79, 1993) report cloning and sequencing B7-2 gene. Thus, in one embodiment the B7-1 gene or the B7-2 genes are administered in conjunction with the Mtb polypeptide. The insertion of nucleic acids encoding B7-1 and B7-2 into vaccinia virus has been disclosed (see for example, U.S. Pat. No. 6,893,869, incorporated herein by reference; this U.S. patent also discloses the use of a nucleic acid encoding IL-2 in a vaccinia virus). Several vectors including IL-2, B7-1 and B7-2 have been deposited with the American Type Culture Collection (ATCC) on Oct. 3, 1994 under the terms of the Budapest Treaty (for example, rV-CEA/$_n$IL-2 (ATCC Designation VR 2480), rV-$_m$B7-2 (ATCC Designation VR 2482); and rV-$_m$B7-1 (ATCC Designation VR 2483)).

DNA sequences encoding a Mtb polypeptide can be expressed in vitro by DNA transfer into a suitable host cell. The cell may be prokaryotic or eukaryotic. The term also includes any progeny of the subject host cell. It is understood that all progeny may not be identical to the parental cell since there may be mutations that occur during replication. Methods of stable transfer, meaning that the foreign DNA is continuously maintained in the host, are known in the art.

As noted above, a polynucleotide sequence encoding a Mtb polypeptide can be operatively linked to expression control sequences. An expression control sequence operatively linked to a coding sequence is ligated such that expression of the coding sequence is achieved under conditions compatible with the expression control sequences. The expression control sequences include, but are not limited to, appropriate promoters, enhancers, transcription terminators, a start codon (i.e., ATG) in front of a protein-encoding gene, splicing signal for introns, maintenance of the correct reading frame of that gene to permit proper translation of mRNA, and stop codons.

Hosts cells can include microbial, yeast, insect and mammalian host cells. Methods of expressing DNA sequences having eukaryotic or viral sequences in prokaryotes are well known in the art. Non-limiting examples of suitable host cells include bacteria, archea, insect, fungi (for example, yeast), mycobacterium (such as *M. smegmatis*), plant, and animal cells (for example, mammalian cells, such as human). Exemplary cells of use include *Escherichia coli, Bacillus subtilis, Saccharomyces cerevisiae, Salmonella typhimurium*, SF9 cells, C129 cells, 293 cells, *Neurospora*, and immortalized mammalian myeloid and lymphoid cell lines. Techniques for the propagation of mammalian cells in culture are well-known (see, Jakoby and Pastan (eds), 1979, Cell Culture. Methods in Enzymology, volume 58, Academic Press, Inc., Harcourt Brace Jovanovich, N.Y.). Examples of commonly used mammalian host cell lines are VERO and HeLa cells, CHO cells, and WI38, BHK, and COS cell lines, although cell lines may be used, such as cells designed to provide higher expression desirable glycosylation patterns, or other features. As discussed above, techniques for the transformation of yeast cells, such as polyethylene glycol transformation, protoplast transformation and gene guns are also known in the art (see Gietz and Woods Methods in Enzymology 350: 87-96, 2002).

Transformation of a host cell with recombinant DNA can be carried out by conventional techniques as are well known to those skilled in the art. Where the host is prokaryotic, such as, but not limited to, *E. coli*, competent cells which are capable of DNA uptake can be prepared from cells harvested after exponential growth phase and subsequently treated by the $CaCl_2$ method using procedures well known in the art. Alternatively, $MgCl_2$ or RbCl can be used. Transformation can also be performed after forming a protoplast of the host cell if desired, or by electroporation.

When the host is a eukaryote, such methods of transfection of DNA as calcium phosphate coprecipitates, conventional mechanical procedures such as microinjection, electroporation, insertion of a plasmid encased in liposomes, or virus vectors can be used. Eukaryotic cells can also be co-transformed with polynucleotide sequences encoding a Mtb polypeptide, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein (see for example, *Eukaryotic Viral Vectors*, Cold Spring Harbor Laboratory, Gluzman ed., 1982).

Therapeutic Methods and Pharmaceutical Compositions

The Mtb polypeptides disclosed herein, or nucleic acids encoding the Mtb polypeptides, can be used to generate an immune response in a subject. In several examples, the subject is infected with Mtb or is at risk of being infected with Mtb. Thus, in several embodiments, the methods include administering to a subject a therapeutically effective amount of one or more of the Mtb polypeptides disclosed herein (or polynucleotides encoding these polypeptides), in order to generate an immune response, such as, but not limited to, a protective immune response.

In exemplary applications, compositions are administered to a subject having in an amount sufficient to produce an immune response to Mtb. These Mt polypeptides, or polynucleotides encoding these polypeptides are of use to prevent an infection with Mtb, prevent progression to disease in a subject having a latent Mtb infection, or to treat tuberculosis in a subject infected with Mtb. In several examples, administration of a therapeutically effective amount of a composition including one or move of the Mtb polypeptides disclosed herein (or polynucleotides encoding these polypeptides) induces a sufficient immune response to decrease a symptom of a disease due to Mtb infection, to prevent the development of one or more symptoms of tuberculosis, or to prevent infection with Mtb.

In some examples, the compositions are of use in preventing a future infection with Mtb. Thus, a therapeutically effective amount of the composition is administered to a subject at risk of becoming infective with Mtb. The composition prevents the development of tuberculosis, such as latent or active tuberculosis in the subject upon subsequent exposure to Mtb.

In additional examples, the compositions are administered to a subject with a, latent Mtb infection, and prevent the development of symptoms of tuberculosis. Thus the compositions are of use in treating a subject with latent tuberculosis, such that the subject does not develop active tuberculosis.

Amounts effective for these uses will depend upon the severity of the disease, the general state of the patient's health, and the robustness of the patient's immune system. In one example, a therapeutically effective amount of the compound is that which provides either subjective relief of a symptom(s) or an objectively identifiable improvement as noted by the clinician or other qualified observer. In other examples, a therapeutically effective amount is an amount sufficient to prevent an infection with Mtb in a subject upon subsequent exposure of the subject to Mtb. In additional examples, a therapeutically effective amount is an amount sufficient to prevent development of symptom in a subject infected with Mtb.

A Mtb polypeptide can be administered by any means known to one of skill in the art (see Banga, A., "Parenteral Controlled Delivery of Therapeutic Peptides and Proteins," in *Therapeutic Peptides and Proteins*, Technomic Publishing Co., Inc., Lancaster, Pa., 1995) either locally or systemically, such as by intramuscular injection, subcutaneous injection, intraperitoneal infection, intravenous injection, oral administration, nasal administration, transdermal administration or even anal administration. In one embodiment, administration is by oral, subcutaneous injection or intramuscular injection. To extend the time during which the peptide or protein is available to stimulate a response, the peptide or protein can be provided as an implant, an oily injection, or as a particulate system. The particulate system can be a microparticle, a microcapsule, a microsphere, a nanocapsule, or similar particle. (see, e.g., Banga, supra). A particulate carrier based on a synthetic polymer has been shown to act as an adjuvant to enhance the immune response, in addition to providing a controlled release. Aluminum salts can also be used as adjuvants to produce an immune response.

In one specific, non-limiting example, the Mtb polypeptide is administered in a manner to direct the immune response to a cellular response (that is, a cytotoxic T lymphocyte (CTL) response), rather than a humoral (antibody) response.

Optionally, one or more cytokines, such as IL-2, IL-6, IL-12, RANTES, GM-CSF, TNF-α, or IFN-γ, one or more growth factors, such as GM-CSF or G-CSF; one or more molecules such as OX-40L or 41 BBL, or combinations of these molecules, can be used as biological adjuvants (see, for example, Salgaller et al., 1998, J. Surg. Oncol. 68(2):122-38; Lotze et al., 2000, Cancer J. Sci. Am. 6(Suppl 1):S61-6; Cao et al., 1998, Stem Cells 16(Suppl 1):251-60; Kuiper et al., 2000, Adv. Exp. Med. Biol. 465:381-90). These molecules can be administered systemically (or locally) to the host. In several examples, IL-2, RANTES, GM-CSF, TNF-α, IFN-γ, G-CSF, LFA-3, CD72, B7-1, B7-2, B7-1, B7-2, OX-40L, 41 BBL and ICAM-1 are administered.

A number of means for inducing cellular responses, both in vitro and in vivo, are known. Lipids have been identified as agents capable of assisting in priming CTL in vivo against various antigens. For example, as described in U.S. Pat. No. 5,662,907, palmitic acid residues can be attached to the alpha and epsilon amino groups of a lysine residue and then linked (for example, via one or more linking residues, such as glycine, glycine-glycine, serine, serine-serine, or the like) to an immunogenic peptide. The lipidated peptide can then be injected directly in a micellar form, incorporated in a liposome, or emulsified in an adjuvant. As another example, *E. coli* lipoproteins, such as tripalmitoyl-S-glycerylcysteinly-seryl-serine can be used to prime tumor specific CTL when covalently attached to an appropriate peptide (see, Deres et al., *Nature* 342:561, 1989). Further, as the induction of neutralizing antibodies can also be primed with the same molecule conjugated to a peptide which displays an appropriate epitope, two compositions can be combined to elicit both humoral and cell-mediated responses where that is deemed desirable. A pharmaceutical composition including a Mtb polypeptide is thus provided.

These compositions are of use to promote an immune response to Mtb. In one embodiment, the Mtb polypeptide is mixed with an adjuvant containing two or more of a stabilizing detergent, a micelle-forming agent, and an oil. Suitable stabilizing detergents, micelle-forming agents, and oils are detailed in U.S. Pat. Nos. 5,585,103; 5,709,860; 5,270,202; and 5,695,770, all of which are incorporated by reference. A stabilizing detergent is any detergent that allows the components of the emulsion to remain as a stable emulsion. Such detergents include polysorbate, 80 (TWEEN) (Sorbitan-mono-9-octadecenoate-poly(oxy-1,2-ethanediyl; manufactured by ICI Americas, Wilmington, Del.), TWEEN 40™, TWEEN 20™, TWEEN 60™, ZWITTERGENT™ 3-12, TEEPOL HB7™, and SPAN 85™. These detergents are usually provided in an amount of approximately 0.05 to 0.5%, such as at about 0.2%. A micelle forming agent is an agent which is able to stabilize the emulsion formed with the other components such that a micelle-like structure is formed. Such agents generally cause some irritation at the site of injection in order to recruit macrophages to enhance the cellular response. Examples of such agents include polymer surfactants described by BASF Wyandotte publications, e.g., Schmolka, *J. Am. Oil. Chem. Soc.* 54:110, 1977, and Hunter et al., *J. Immunol.* 129:1244, 1981, PLURONIC™ L62LF, L101, and L64, PEG1000, and TETRONIC™ 1501, 150R1, 701, 901, 1301, and 130R1. The chemical structures of such agents are well known in the art. In one embodiment, the agent is chosen to have a hydrophile-lipophile balance (HLB) of between 0 and 2, as defined by Hunter and Bennett, *J. Immun.* 133:3167, 1984. The agent can be provided in an effective amount, for example between 0.5 and 10%, or in an amount between 1.25 and 5%.

The oil included in the composition is chosen to promote the retention of the antigen in oil-in-water emulsion, such as to provide a vehicle for the desired antigen, and preferably has a melting temperature of less than 65° C. such that emulsion is formed either at room temperature (about 20° C. to 25° C.), or once the temperature of the emulsion is brought down to room temperature. Examples of such oils include squalene, Squalane, EICOSANE™, tetratetracontane, glycerol, and peanut oil or other vegetable oils. In one specific, non-limiting example, the oil is provided in an amount between 1 and 10%, or between 2.5 and 5%. The oil should be both biodegradable and biocompatible so that the body can break down the oil over time, and so that no adverse affects, such as granulomas, are evident upon use of the oil.

In one embodiment, the adjuvant is a mixture of stabilizing detergents, micelle-forming agent, and oil available under the name PROVAX® (IDEC Pharmaceuticals, San Diego, Calif.). An adjuvant can also be an immunostimulatory nucleic acid, such as a nucleic acid including a CpG motif, or a biological adjuvant (see above).

Controlled release parenteral formulations can be made as implants, oily injections, or as particulate systems. For a broad overview of protein delivery systems, see Banga, *Therapeutic Peptides and Proteins: Formulation, Processing, and Delivery Systems*, Technomic Publishing Company, Inc., Lancaster, Pa., 1995. Particulate systems include microspheres, microparticles, microcapsules, nanocapsules, nanospheres, and nanoparticles. Microcapsules contain the therapeutic protein as a central core. In microspheres, the therapeutic agent is dispersed throughout the particle. Particles, microspheres, and microcapsules smaller than about 1 μm are generally referred to as nanoparticles, nanospheres, and nanocapsules, respectively. Capillaries have a diameter of approximately 5 μm so that only nanoparticles are administered intravenously. Microparticles are typically around 100 μm in diameter and are administered subcutaneously or intramuscularly (see Kreuter, *Colloidal Drug Delivery Systems*, J. Kreuter, ed., Marcel Dekker, Inc., New York, N.Y., pp. 219-342, 1994; Tice & Tabibi, *Treatise on Controlled Drug Delivery*, A. Kydonieus, ed., Marcel Dekker, Inc. New York, N.Y., pp. 315-339, 1992).

Polymers can be used for ion-controlled release. Various degradable and nondegradable polymeric matrices for use in controlled drug delivery are known in the art (Langer, *Accounts Chem. Res.* 26:537, 1993). For example, the block copolymer, polaxamer 407 exists as a viscous yet mobile liquid at low temperatures but forms a semisolid gel at body temperature. It has shown to be an effective vehicle for formulation and sustained delivery of recombinant interleukin-2 and urease (Johnston et al., *Pharm. Res.* 9:425, 1992; and Pec, *J. Parent. Sci. Tech.* 44(2):58, 1990). Alternatively, hydroxyapatite has been used as a microcarrier for controlled release of proteins (Ijntema et al., *Int. J. Pharm.* 112:215, 1994). In yet another aspect, liposomes are used for controlled release as well as drug targeting of the lipid-capsulated drug (Betageri et al., *Liposome Drug Delivery Systems*, Technomic Publishing Co., Inc., Lancaster, Pa., 1993). Numerous additional systems for controlled delivery of therapeutic proteins are known (e.g., U.S. Pat. Nos. 5,055,303; 5,188,837; 4,235,871; 4,501,728; 4,837,028; 4,957,735; and 5,019,369; 5,055,303; 5,514,670; 5,413,797; 5,268,164; 5,004,697; 4,902,505; 5,506,206; 5,271,961; 5,254,342; and 5,534,496).

In another embodiment, a pharmaceutical composition includes a nucleic acid encoding an Mtb polypeptide. A therapeutically effective amount of the Mtb polynucleotide can be administered to a subject in order to generate an immune response.

Optionally, one or more cytokines, such as IL-2, IL-6, IL-12, RANTES, GM-CSF, TNF-α, or IFN-γ, one or more growth factors, such as GM-CSF or G-CSF, one or more costimulatory molecules, such as ICAM-1, LFA-3, CD72, B7-1, B7-2, or other B7 related molecules; one or more molecules such as OX-40L or 41 BBL, or combinations of these molecules, can be used as biological adjuvants (see, for example, Salgaller et al., 1998, J. Surg. Oncol. 68(2):122-38; Lotze et al., 2000, Cancer J. Sci. Am. 6(Suppl 1):S61-6; Cao et al., 1998, Stem Cells 16(Suppl 1):251-60; Kuiper et al., 2000, Adv. Exp. Med. Biol. 465:381-90). These molecules can be administered systemically to the host. It should be noted that these molecules can be co-administered via insertion of a nucleic acid encoding the molecules into a vector, for example, a recombinant pox vector (see, for example, U.S. Pat. No. 6,045,802). In various embodiments, the nucleic acid encoding the biological adjuvant can be cloned into same vector as the Mtb polypeptide coding sequence, or the nucleic acid can be cloned into one or more separate vectors for co-administration. In addition, nonspecific immunomodulating factors such as *Bacillus* Cahnette-Guerin (BCG) and levamisole can be co-administered.

One approach to administration of nucleic acids is direct immunization with plasmid DNA, such as with a mammalian expression plasmid. As described above, the nucleotide sequence encoding an Mtb polypeptide can be placed under the control of a promoter to increase expression of the molecule.

Immunization by nucleic acid constructs is well known in the art and taught, for example, in U.S. Pat. No. 5,643,578 (which describes methods of immunizing vertebrates by introducing DNA encoding a desired antigen to elicit a cell-mediated or a humoral response), and U.S. Pat. Nos. 5,593,972 and 5,817,637 (which describe operably linking a nucleic acid sequence encoding an antigen to regulatory sequences enabling expression). U.S. Pat. No. 5,880,103 describes several methods of delivery of nucleic acids encoding immunogenic peptides or other antigens to an organism. The methods include liposomal delivery of the nucleic acids (or of the synthetic peptides themselves), and immune-stimulating constructs, or ISCOMS™, negatively charged cage-like structures of 30-40 nm in size formed spontaneously on mixing cholesterol and Quil A™ (saponin). Protective immunity has been generated in a variety of experimental models of infection, including toxoplasmosis and Epstein-Barr virus-induced tumors, using ISCOMS™ as the delivery vehicle for antigens (Mowat and Donachie, *Immunol. Today* 12:383, 1991). Doses of antigen as low as 1 μg encapsulated in ISCOMS™ have been found to produce Class I mediated CTL responses (Takahashi et al., *Nature* 344:873, 1990).

In another approach to using nucleic acids for immunization, an Mtb polypeptide can also be expressed by attenuated viral hosts or vectors or bacterial vectors. Recombinant vaccinia virus, adeno-associated virus (AAV), herpes virus, retrovirus, or other viral vectors can be used to express the peptide or protein, thereby eliciting a CTL response. For example, vaccinia vectors and methods useful in immunization protocols are described in U.S. Pat. No. 4,722,848. BCG (*Bacillus* Calmette Guerin) provides another vector for expression of the peptides (see Stover, *Nature* 351:456-460, 1991).

When a viral vector is utilized, it is desirable to provide the recipient with a dosage of each recombinant virus in the composition in the range of from about $10^5$ to about $10^{10}$ plaque forming units/mg mammal, although a lower or higher dose can be administered. The composition of recombinant viral vectors can be introduced into a mammal (1) prior to any evidence of an infection with Mtb; (2) to prevent development of tuberculosis in an individual infected with tuberculosis; or (3) to decrease a symptom of tuberculosis in a mammal infected with Mtb. Examples of methods for administering the composition into mammals include, but are not limited to, exposure of cells to the recombinant virus ex vivo, or injection of the composition into the affected tissue or intravenous, subcutaneous, intradermal or intramuscular administration of the virus. Alternatively the recombinant viral vector or combination of recombinant viral vectors may be administered locally in a pharmaceutically acceptable carrier. Generally, the quantity of recombinant viral vector, carrying the nucleic acid sequence of one or more Mtb polypeptides to be administered is based on the titer of virus particles. An exemplary range of the immunogen to be administered is $10^5$ to $10^{10}$ virus particles per mammal, such as a human.

In the embodiment where a combination of a first recombinant viral vector carrying a nucleic acid sequence of one or more Mtb polypeptide and a second recombinant viral vector carrying the nucleic acid sequence of one or more immunostimulatory molecules is used, the mammal can be immunized with different ratios of the first and second recombinant viral vector. In one embodiment the ratio of the first vector to the second vector is about 1:1, or about 1:3, or about 1:5. Optimal ratios of the first vector to the second vector may easily be titered using the methods known in the art (see, for example, U.S. Pat. No. 6,893,869, incorporated herein by reference).

In one embodiment the recombinant viruses have been constructed to express cytokines (such as TNF-α, IL-6, GM-CSF, and IL-2), and co-stimulatory and accessory molecules (B7-1, B7-2) alone and in a variety of combinations. Simultaneous production of an immunostimulatory molecule and the Mtb polypeptide enhances the generation of specific effectors. Without being bound by theory, dependent upon the specific immunostimulatory molecules, different mechanisms might be responsible for the enhanced immunogenicity: augmentation of help signal (IL-2), recruitment of professional APC (GM-CSF), increase in CTL frequency (IL-2), effect on antigen processing pathway and MHC expression (IFNγ and TNFα) and the like. For example, IL-2, IL-6, interferon, tumor necrosis factor, or a nucleic acid encoding these molecules, can be administered in conjunction with a Mtb immunogenic polypeptide, or a nucleic acid encoding an Mtb polypeptide. The co-expression of a Mtb polypeptide together with at least one immunostimulatory molecule can be effective in an animal model to show anti-tumor effects.

In one embodiment, a nucleic acid encoding an Mtb polypeptide is introduced directly into cells. For example, the nucleic acid can be loaded onto gold microspheres by standard methods and introduced into the skin by a device such as Bio-Rad's Helios™ Gene Gun. The nucleic acids can be "naked," consisting of plasmids under control of a strong promoter. Typically, the DNA is injected into muscle, although it can also be injected directly into other sites, including tissues in proximity to metastases. Dosages for injection are usually around 0.5 μg/kg to about 50 mg/kg, and typically are about 0.005 mg/kg to about 5 mg/kg (see, for example, U.S. Pat. No. 5,589,466).

In one specific, non-limiting example, a pharmaceutical composition for intravenous administration would include about 0.1 μg to 10 mg of immunogenic Mtb polypeptide per patient per day. Dosages from 0.1 up to about 100 mg per patient per day can be used, particularly if the agent is administered to a secluded site and not into the circulatory or lymph system, such as into a body cavity or into a lumen of an organ. Actual methods for preparing administrable compositions will be known or apparent to those skilled in the art and are described in more detail in such publications as *Remingtons Pharmaceutical Sciences,* $19^{th}$ Ed., Mack Publishing Company, Easton, Pa., 1995.

Single or multiple administrations of the compositions are administered depending on the dosage and frequency as required and tolerated by the subject. In one embodiment, the dosage is administered once as a bolus, but in another embodiment can be applied periodically until a therapeutic result is achieved. In one embodiment, the dose is sufficient to treat or ameliorate symptoms or signs of tuberculosis without producing unacceptable toxicity to the subject. In another embodiment, the dose is sufficient to prevent infection with Mtb upon subsequent exposure to Mtb. In a further embodiment, the dose is sufficient to prevent a symptom of tuberculosis in a subject with a latent Mtb infection. Systemic or local administration can be utilized.

In another method, antigen presenting cells (APCs), such as dendritic cells, are isolated from a subject of interest and pulsed or co-incubated with peptides comprising an Mtb polypeptide in vitro. In one specific, non-limiting example, the antigen presenting cells are autologous cells isolated from the subject of interest. A therapeutically effective amount of the antigen presenting cells is administered (re-introduced) to the subject of interest.

The Mtb polypeptide can be delivered to the dendritic cells or to dendritic cell precursors via any method known in the art, including, but not limited to, pulsing dendritic cells directly with antigen, or utilizing a broad variety of antigen delivery vehicles, such as, for example, liposomes, or other vectors known to deliver antigen to cells. In one specific, non-limiting example an antigenic formulation includes about 0.1 μg to about 1,000 μg, or about 1 to about 100 μg of a selected Mtb polypeptide. The Mtb polypeptide can also be administered with agents that promote dendritic cell maturation. Specific, non-limiting examples of agents of use are interleukin-4 (IL-4) and granulocyte/macrophage colony stimulating factor (GM-CSF), or flt-3 ligand (flt-3L). The preparation can also contain buffers, excipients, and preservatives, amongst other ingredients.

In one embodiment, mature antigen presenting cells are generated to present the immunogenic Mtb polypeptide. These dendritic cells are then administered alone to a subject infected with Mtb, or at risk for infection with Mtb. In another embodiment, the mature dendritic cells are administered in conjunction with an antiviral agent.

Alternatively, the APCs are used to sensitize CD8 cells, such as peripheral blood lymphocytes (PBLs). The PBLs can be from the same subject (autologous) that is to be treated. Alternatively, the PBLs can be heterologous. However, they should at least be MHC Class-I restricted to the HLA types the subject possesses. An effective amount of the sensitized cells are then administered to the subject.

Peripheral blood mononuclear cells (PBMCs) can be used as the responder cell source of cytotoxic T lymphocyte (CTL) precursors. The appropriate antigen-presenting cells are incubated with peptide, after which the peptide-loaded antigen-presenting cells are then incubated with the responder cell population under optimized culture conditions. Positive CTL activation can be determined by assaying the culture for the presence of CTLs that kill radio-labeled target cells, both specific peptide-pulsed targets as well as target cells expressing endogenously processed forms of the antigen from which the peptide sequence was derived.

Alternatively, a $CD8^+$ T cell clone that recognizes the Mtb polypeptide can be isolated from a subject of interest. This $CD8^+$ T cell clone can be expanded in vitro, using methods known in the art. A therapeutically effective amount of the CD8+ T cells is then administered to the subject of interest.

Thus, cells can be administered to a subject to treat or an Mtb infection, such as to decrease a symptom of an Mtb infection. In these applications, a therapeutically effective amount of activated antigen presenting cells, or activated lymphocytes, are administered to a subject in an amount sufficient to raise an immune response to Mtb.

In supplemental methods, any therapeutic regimen is augmented by administering a cytokine, such as interleukin (IL)-2, IL-3, IL-6, IL-10, IL-12, IL-15, GM-CSF, interferons. In further methods, an additional antiviral agent is administered to the subject.

The disclosure is illustrated by the following non-limiting Examples.

EXAMPLES

For many infections, the repertoire of the CD8 response is shaped by the entry of antigen into the MHC-I processing pathway, binding of peptides and/or non-peptide antigens to MHC-I molecules, and recognition of these structures by T cells. Ultimately, a relatively limited subset of pathogen-specific T cells emerge. While a number of commonly recognized CD4 Mtb antigens have been described (Reed et al., *Microbes Infect* 7:922-931, 2005) (ESAT-6, CFP10, Ag85, etc.), surprisingly little is known about common Mtb antigens recognized by human CD8+ T cells. The majority of CD8 epitopes that have been identified were defined by testing of Mtb peptides selected for high affinity binding to MHC Class Ia molecules (HLA-A2 in most cases (see, for example, Lalvani, *Microbes Infect* 7:922-931, 1998)). In almost all of these, however, the ex vivo frequency of these T cells in Mtb-infected individuals is low or undetectable, suggesting that these specificities may not represent immunodominant responses. In contrast, in the limited cases in which T cells have been used to define epitopes contained in selected Mtb antigens, high ex vivo frequencies have been demonstrated (see Lewinsohn et al., *Am J Respir Crit Care Med* 166:843-848, 2002), suggesting, that a T cell-centered approach can identify immunodominant epitopes. Moreover, CD8 T cell responses to some Mtb antigens which represent good CD4 antigens (CFP10, ESAT-6, Ag85, and Mtb39) have been detected at high frequency in persons infected with Mtb. Therefore, a limited library of overlapping synthetic peptides representing several known CD4 Mtb antigens was used to determine the magnitude of the CD8 response to these antigens in persons with active tuberculosis (TB) and latent tuberculosis infection (LTBI) as well as uninfected subjects. Furthermore, a panel of Mtb-specific CD8+ T cell clones was utilized to define minimal epitopes recognized within these antigens and determined the contribution of these novel epitopes to the ex vivo Mtb-specific CD8 response.

Example 1

Materials and Methods

Human subjects. Uninfected individuals were defined as healthy individuals with a negative tuberculin skin test (TST) and no know risk factors for infection with Mtb. Individuals with LTBI were defined as healthy persons with a positive TST and no symptoms and signs of active TB. In all active TB cases, pulmonary TB was diagnosed by the TB Controller of the county and confirmed by positive sputum culture for *Mycobacterium tuberculosis*. Peripheral blood mononuclear cells (PBMC) were isolated from whole blood obtained by venipuncture or apheresis.

Media and Reagents. Culture medium consisted of RPMI 1640 supplemented with 10% Fetal Bovine Sera (FBS; Bio Whittaker), $5 \times 10^{-5}$ M 2 ME (Sigma-Aldrich), and 2 mM glutamine (GIBCO BRL). For the growth and assay of Mtb-reactive T cell clones, RPMI 1640 was supplemented with 10% human serum. Mtb strain H37Rv was obtained from the American Type Culture Collection (10801 Universtity Bouleveard., Manassas, VA 20110-2209) and prepared as previously described (Lewinsohn et al., *J Immunol* 165:925-930, 2000). Peptides were synthesized by Genemed Synthesis, Inc, (San Francisco, Calif.). Synthetic peptide pools consisted of 15-mers overlapping by 11 amino acids (aa) representing Mtb proteins demonstrated to be potent CD4 antigens. Peptide pools representing CFP-10 (Berthet et al., Microbiology 144:3195-3203, 1998; Dillon et al., *J Clin Microbiol* 38:3285-3290, 2000), ESAT-6 (Sorenson et al., *Infect Immun* 63:1710-1717, 1995), Mtb39a (two pools, A & B, reference) (Dillon et al., *Infect Immun* 67:2941-2950, 1999), Mtb8.4 (Coler et al., *J Immunol* 161:2356-2364, 1998), Mtb 9.9 (Alderson et al., *J Exp Med* 191:551-560, 2000), (Coler et al., *J Immunol* 161:2356-2364, 1998), Mtb 9.9 (Alderson et al., *J Exp Med* 191:551-560, 2000), EsxG (Rosenkrands et al., *Electrophoresis* 21:3740-3756, 2002), 19 kDa antigen (Collins et al. *J Gen Microbiol* 136:1429-1436, 1990), antigen 85 b (Borremans et al., *Infect Immun* 57:3123-3130, 1989) (two pools, A & B, reference) were synthesized. Peptides were resuspended in DMSO and up to 50 peptides were combined into one pool such that each peptide in the pool was at a concentration of 1mg/ml. Peptide pools were stored at −80° C.

Cell Lines and T Cell Clones. EBV-transformed B cell lines, LCL, were either generated using supernatants from the cell line 9B5-8 (American Type Culture Collection, Manassas, Va.) or obtained from the National Marrow Donor Program (NMDP; Minneapolis, MN). LCL were maintained by continuous passage as previously described (Heinzel et al., *J Exp Med* 196:1473-1481, 2002). Mtb-specific T cell clones were isolated from individuals with LTBI or active tuberculosis, using Mtb-infected DCs as APCs and limiting dilution cloning methodology as previously described (Lewinsohn et al., *J Immunol* 165:925-930, 2000). Briefly, CD8+ T cells were isolated from PBMC using negative selection using CD4 antibody-coated beads and then positive selection using CD8 antibody-coated magnetic beads per the manufacturer's instructions (Miltenyi Biotec, Auburn Calif.) or via flow cytometry. In this case, CD4-PE (BD Biosciences cat# 555347) negative, CD8-APC (BD Biosciences, cat# 555369) positive cells (purity >99%) were sorted on a Becton Dickenson LSR II. T cells were seeded at various concentrations in the presence of a $1 \times 10^5$ irradiated autologous Mtb-infected DC, generated as described below, and rIL-2 (5 ng/ml) in cell culture media consisting of 200 µl of RPMI 1640 supplemented with 10% human sera. Wells exhibiting growth between 10-14 days, were assessed for Mtb specificity using ELISPOT and Mtb-infected DC as a source of APCs. T cells retaining Mtb specificity were further phenotyped for αβ T cell receptor expression and CD8 expression by FACS and expanded as described below. Vβ usage was determined using the IOTest Beta Mark Kit from Beckman Coulter.

Expansion of T cell clones. To expand the CD8+ T cell clones, a rapid expansion protocol using anti-CD3 mAb stimulation was used as described previously (Heinzel et al., *J Exp Med* 196:1473-1481, 2002).

Generation and Infection of Peripheral Blood DCs. Monocyte-derived DCs were prepared (Heinzel et al., supra;

Romani et al., *J Exp Med* 180:83-93, 1994). To generate Mtb-infected DC, cells (1×10⁶) were cultured overnight in the presence of Mtb (multiplicity of infection [MOI]=50:1). After 18 hours, the cells were harvested and resuspended in RPMI/10% human serum.

MHC binding assays. The MHC-peptide binding assay utilized measures the ability of peptide ligands to inhibit the binding of a radiolabeled peptide to purified MHC molecules, and has been described in detail elsewhere (Sidney et al., 1999. UNIT 18.3 Measurement of MHC/peptide interactions by gel filtration. In Current Protocols in Immunology. Coligan et al., eds., John Wiley & Sons, Inc., 1996). Briefly, purified MHC molecules, test peptides, and a radiolabeled probe peptide were incubated at room temperature in the presence of human B2-microglobulin and a cocktail of protease inhibitors. After a two-day incubation, binding of the radiolabeled peptide to the corresponding MHC class 1 molecule was determined by capturing MHC/peptide complexes on W6/32 antibody (anti-HLA A, B, and C) or B123.2 (anti-HLA B, C and some A) coated plates, and bound counts per minute (cpm) were measured using a microscintillation counter. For competition assays, the concentration of peptide yielding 50% inhibition of the binding of the radiolabeled peptide was calculated. Peptides were typically tested at six different concentrations covering a 100,000-fold dose range, and in three or more independent assays. Under the conditions utilized, where [label]<[MHC] and $IC_{50} \geq$ [MHC], the measured $IC_{50}$ values are reasonable approximations of the true Kd values.

IFN-γ ELISPOT assay. The IFN-γ ELISPOT assay was performed as described previously (Beckman et al., *J Immunol* 157:2795-2803, 1996). For determination of ex vivo frequencies of CD4⁺ or CD8⁺ T cells responding to Mtb infection or Mtb antigens, CD4⁺ or CD8⁺ T-cells were positively selected from PBMC using magnetic beads (Miltenyi Biotec, Auburn Calif.) as a source of responder T cells and tested in duplicate at four different cell concentrations. Autologous DC (20,000 cells/well) were used as APC and DC were either infected with Mtb or pulsed with peptide pools (5 µg/ml, final concentration of each peptide) and then added to the assay. For assays using T cell clones, T cells (1000 or 5000 cells/well) were incubated with autologous LCL (20,000 cells/well) in the presence or absence of antigen.

Data analysis: To determine the ex vivo frequency of antigen-specific T cells, the average number of spots per well for each duplicate was plotted against the number of responder cells per well. Linear regression analysis was used to determine the slope of the line, which represents the frequency of antigen-specific T cells. The assay is considered positive, i.e. reflecting the presence of a primed T cell response, if the binomial probability (Lewinshon et al., *Microbes Infect* 8:2587-2598, 2006) for the number of spots is significantly different by experimental and control assays. To determine differences in ex vivo T cell frequencies between groups, Wilcoxon/Kruskal-Wallis analysis was used.

Example 2

Defining Immunodominant Mtb-Specific CD8+ Antigens

To define immunodominant Mtb-specific CD8⁺ antigens, and to determine whether or not these responses result from infection with Mtb, CD8⁺ T cells were used from donors uninfected, with LTBI, or actively infected with Mtb. Responses were determined either directly ex vivo, or using CD8⁺ T cell clones obtained by limiting dilution cloning on Mtb-infected autologous DC (Lewinsohn et al., *J Immunol* 165:925-930, 2000). As much is known about dominant CD4⁺ Mtb antigens, a panel of these commonly recognized antigens was selected for further evaluation. These were: Mtb39, CFP10, and Mtb8.4, Mtb9.9, ESAT-6, Ag85b, 19 kDa, and EsxG. To avoid bias introduced by using peptides of predicted HLA-binding specificity, we synthesized overlapping peptides (15 aa, overlap 11 aa) to represent the proteins of interest (Lewinshon et al., *J Immunol* 166:439-446, 2001).

To accurately determine the ex vivo effector cell frequencies of CD8⁺ T cells, linear regression analysis was used. As shown in FIG. 1, magnetic bead purified CD8⁺ T cells were tested against peptide pulsed DC over a range of CD8⁺ T cell numbers in an IFN-γ ELISPOT assay. A positive assay was determined as described below and if positive, the antigen specific frequency was determined using linear regression.

Figure 2:
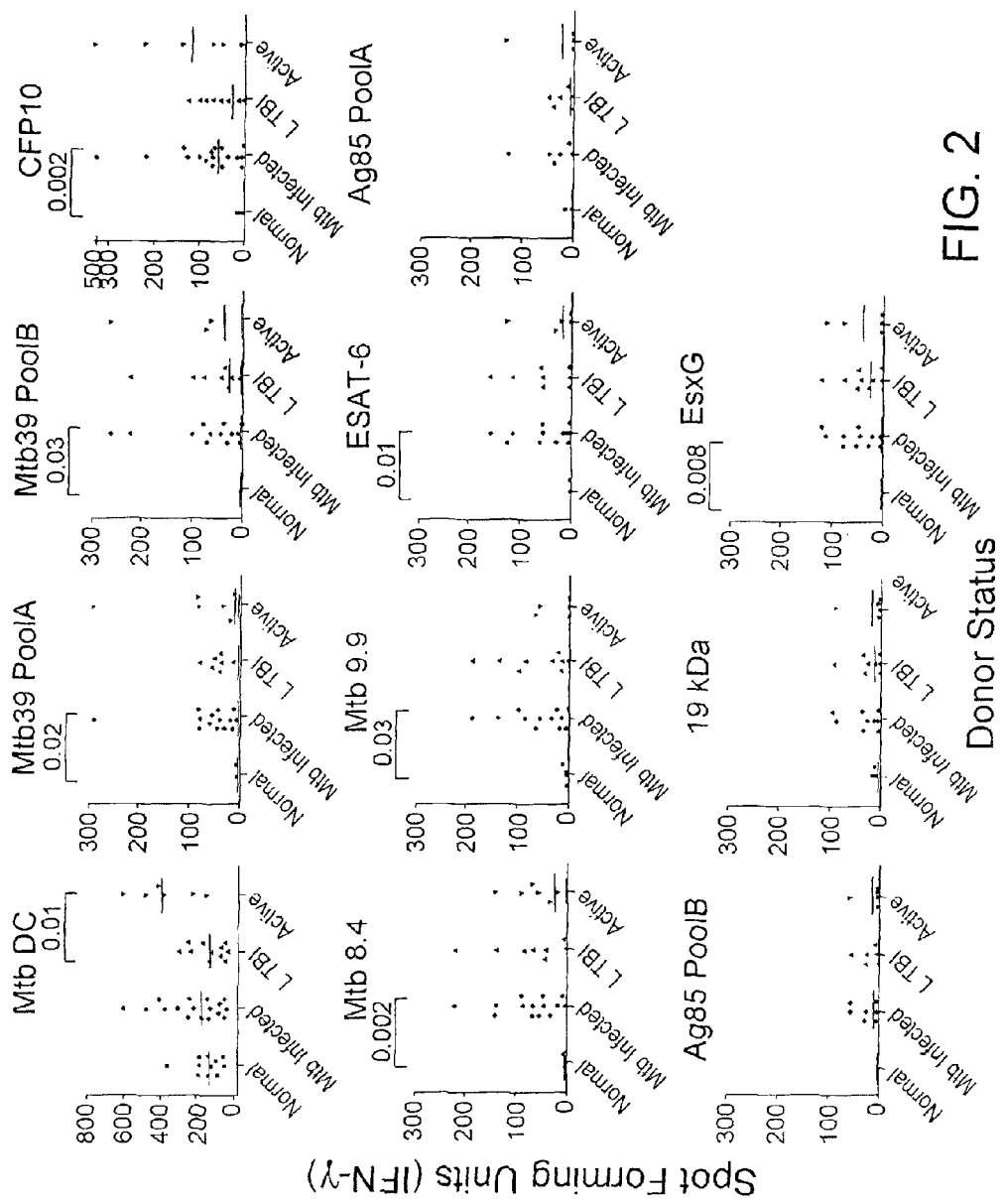
FIG. 2 is a set of graphs showing ex vivo CD8+ T cell frequencies to Mtb antigens are associated with Mtb infection. As described above (see FIG. 1), to determine ex vivo CD8+ T cell frequencies, autologous DC either infected with Mtb or pulsed with cognate peptide pools were incubated with CD8+ T cells in an IFN-γ ELISPOT assay. Subjects without evidence for Mtb infection, those with LTBI, and those with active TB (culture confirmed pulmonary tuberculosis) were evaluated. "Mtb Infected" includes those with latent tuberculosis (TB) infection and active tuberculosis. P values are noted where P=<0.05 (Wilcoxon/Kruskal-Wallis).

Subjects uninfected (n=14), those with LTBI (n=20) and those with active TB (n=12) were evaluated for CD8⁺ responses to a panel of Mtb CD4⁺ T cell antigens, as well as to Mtb-infected DC. All subjects tested had robust CD8⁺ T cell responses to Mtb-infected DC and were of greater magnitude in individuals with active TB than in those with LTBI (p=0.01; FIG. 2, Table I). However, CD8⁺ T cell responses to the panel of Mtb antigens were found almost exclusively in those infected with Mtb in that statistically significant differences between uninfected and Mtb-infected individuals were noted for seven of ten antigens for both the magnitude of the response (FIG. 2) and the proportion of positive assays (Table I).

TABLE I

CD8⁺ T cell responses to known TB antigens.

| Antigen | Mtb Infected # positive[a]/# tested (%) | Mtb Uninfected # positive[a]/# tested (%) | P value (2 tail fishers) |
|---|---|---|---|
| Mtb DC | 17/17 (100) | 11/11 (100) | |
| Mtb39 Pool A | 13/30 (43) | 0/14 (0) | 0.003 |
| Mtb 39 Pool B | 10/30 (33) | 0/14 (0) | 0.01 |
| CFP10 | 14/30 (47) | 1/14 (7) | 0.02 |
| Mtb 8.4 | 13/30 (43) | 0/14 (0) | 0.003 |
| Mtb 9.9 | 10/25 (40) | 1/14 (7) | 0.06 |
| ESAT 6 | 12/25 (48) | 0/14 (0) | 0.003 |
| Ag85b Pool A | 5/22 (23) | 1/14 (7) | 0.37 |
| Ag85b Pool B | 4/22 (18) | 0/14 (0) | 0.14 |
| 19 kd | 6/22 (27) | 1/12 (8) | 0.38 |
| EsxG | 9/22 (41) | 0/14 (0) | 0.006 |

[a]Positive assay defined in text.

However differences in CD8+ T cell responses between individuals with active TB and LTBI were not statistically different. While strong CD8+ T cell responses were observed against many of the antigens tested, it is equally notable that several subjects with strong Mtb directed CD8+ T cell responses did not have demonstrable responses to many of the antigens tested.

These ex vivo frequency data demonstrate the presence of high-frequency responses to a number of known Mtb antigens, but do not shed light on the restricting allele, minimal epitope, or dominance hierarchy within the gene of interest. To address this question, limiting dilution cloning of human CD8+ T cells using Mtb-infected DC was performed (see Lewinsohn et al., *J Immunol* 166:439-446, 2001), and panels of both classically and non-classically HLA-restricted CD8+ T cell clones were generated. Using peptide pools representing known CD4+ antigens, the antigenic specificity of the HLA-Ia restricted clones can be defined in more than half of the clones (Table II).

TABLE II

Many CD8+ T cell clones recognize known CD4+ T cell antigens

| Donor | Tb Status | HLA-Ia Clones (#)[a] | Antigen Identified (#)[b] | # Distinct Antigens (#)[c] | # Distinct Epitopes (#)[d] |
|---|---|---|---|---|---|
| D431 | Active TB | 1 | 0 | 0 | 0 |
| D432 | Active TB | 14 | 4 | 2 | 2 |
| D466 | Active TB | 11 | 10 | 1 | 2 |
| D571 | Active TB | 7 | 7 | 1 | 1 |
| D480 | Active TB | 6 | 6 | 1 | 1 |
| D481 | Active TB | 11 | 11 | 1 | 1 |
| D426 | LTBI | 1 | 0 | 0 | 0 |
| D443 | LTBI | 1 | 1 | 1 | 1 |
| D454 | LTBI | 2 | 2 | 2 | 2 |
| D504 | LTBI | 7 | 1 | 1 | 1 |
| Totals | | 61 | 42 | 10 | 11 |

[a] Number of clones derived from donor.
[b] Number of clones for which cognate antigen was identified.
[c] Total number of distinct antigens identified from the clone set.
[d] Total number of distinct epitopes identified from the clone set.

Figure 3:
FIGS. 3a to 3d are a set of digital images showing the definition of Antigenic Specificity and HLA-Restriction (the characterization of T cell clone D466 D6). For the results shown in FIGS. 3a-3c, to identify the antigen and minimal epitope recognized by T cell clone, D466 D6, T-cells (5000 cells/well) were incubated with autologous LCL (20,000/well) and 5 µg/ml of antigen. IFN-γ was assessed by ELISPOT after eighteen hours of co-culture. For the results presented in FIG. 3a, antigens consisted of peptide pools representing known CD4+ antigens, made up of 15 amino acid (aa) peptides overlapping by 11 aa. For the results presented in FIG. 3b, antigens consisted of individual 15 aa CFP10 peptides that together constitute the peptide pool. For the results presented in FIG. 3c, antigens consisted of individual nested CFP10$_{1-15}$ peptides (10 aa, 9 aa or 8 aa), used to further map the epitope. For the results presented in FIG. 3d, the restricting allele was identified using LCL (20,000/well) expressing HLA alleles matching D466 at one or two alleles, pulsed with CFP10$_{2-10}$ (5 µg/ml) as APC. After 2 hours, cells were washed and incubated with T-cells (500 cells/well) in an IFN-γ ELISPOT assay.
Figure 3:
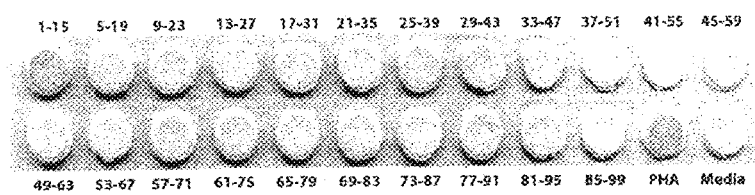
Figure 3:
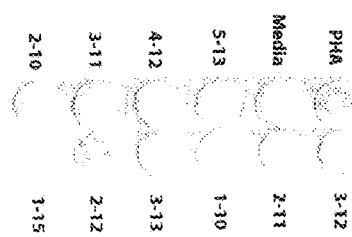
Figure 3:
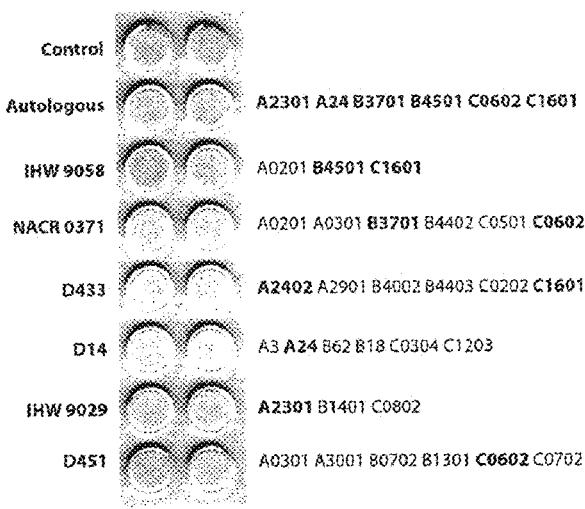
Figure 4:
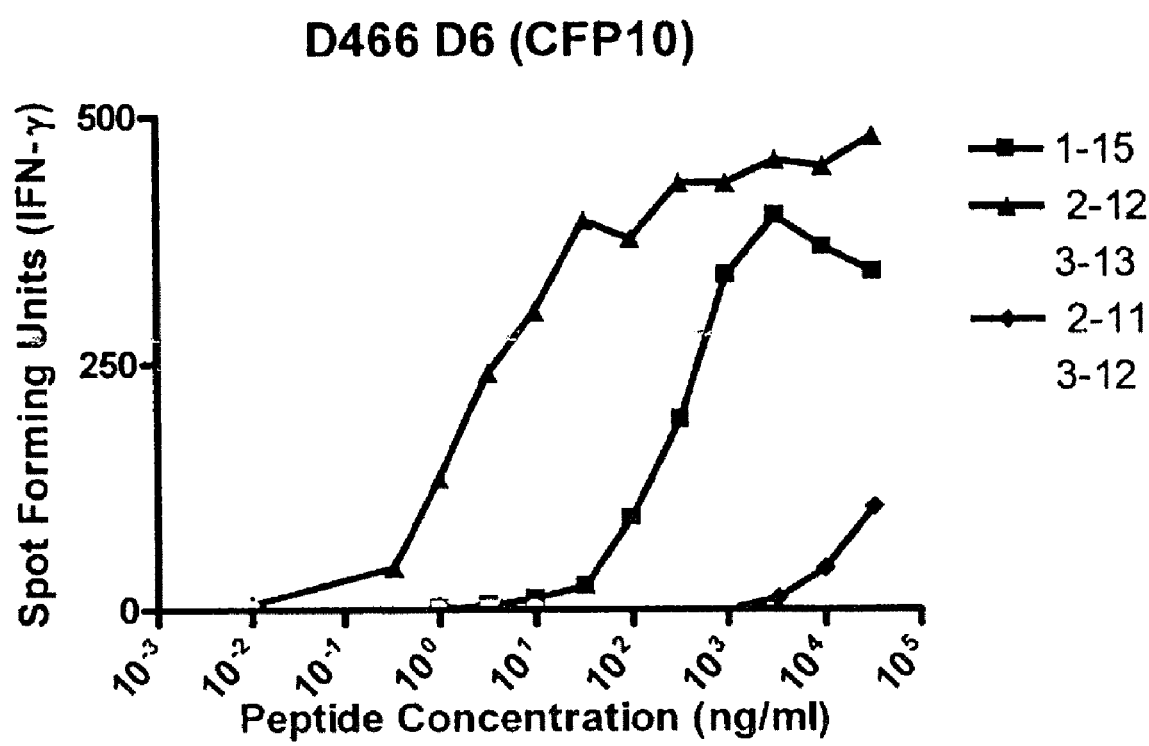
FIG. 4 is a line graph showing the confirmation of minimal epitope mapping of D466 D6. The epitope location (amino acids 1-15, 2-12, 3-13, 2-11 and 3-12 of CFP10) is indicated in the legend shown at the right. To confirm the minimal epitope, autologous LCL (20,000/well) was pulsed with peptide at the concentration indicated and co-cultured with T-cells (1000 cells/well). IFN-γ was assessed by ELISPOT after eighteen hours co-culture. Each point represents the mean of duplicate determinations.

This approach is demonstrated in detail for a single representative clone, D466 D6, derived from a subject with active TB. As shown in FIG. 3A, testing the clone against autologous DC pulsed with a panel of peptide pools unambiguously defined the antigenic specificity as CFP10. The clone was then tested against each of the 15-mer peptides that comprise the CFP10 pool, revealing that the epitope was contained within CFP10$_{1-15}$ (FIG. 3B). Each possible 8 aa, 9 aa, 10 aa, and 11 aa peptide was then synthesized and tested for reactivity, revealing antigenic activity between aa 2-11 (FIG. 3C). Similarly, each clone was tested against lymphoblastoid cell lines (LCL) sharing at least one HLA-type with the donor (FIG. 3D). Autologous LCL and IHW 9058 LCL, which share B4501 and C1601, present the epitope to the clone, identifying both B4501 and C1601 as possible restricting alleles. However, C1601+ D433 LCL do not present the epitope, eliminating C1601 as a candidate restricting allele. Therefore D466 D6 is restricted by HLA-B4501. As demonstrated in FIG. 4, by testing each plausible epitope over a broad range of concentrations, the minimal epitope was defined as CFP10$_{2-10}$ for D466 D6. Experimental data supporting the assignment of the minimal epitope is provided for each clone in the supplemental Figure. A summary of the antigenic specificity, minimal epitope, and HLA-restricting allele is presented in Table III. Unexpectedly, all but one of the T cell clones were restricted by HLA-B alleles. Furthermore, a minority of those observed were 9 aa in length.

TABLE III

Summary of Epitopes Identified

| Clone[a] | Gene | Accession Number | HLA-Restrict Allele | Epitope Locat'n | Epitope Sequence (SEQ ID NO: 26-38) | #SFU[b] | MHC Bind. Aff[c] | V beta region |
|---|---|---|---|---|---|---|---|---|
| D160 1-IB[d] (0) | CFP10 | Rv3874 | B44 | 2-11 | AEMKTDAATL | 360 | 38 | |
| D160 1-6F[d] (0) | CFP10 | Rv3874 | B14 | 85-94 | RADEEQQQAL | 120 | NA | |
| D432 H12 (2) | CFP10 | Rv3874 | B3514 | 49-58 | TAAQAAVVRF | 258 | 2011[e] | 5.3 |
| D466 A10 (10) | CFP10 | Rv3874 | B4501 | 2-9 | AEMKTDAA | 2458 | 48 | IND |
| D466 D6 (1) | CFP10 | Rv3874 | B4501 | 2-12 | AEMKTDAATLA | 1993 | 6.2 | 22 |
| D481 C10 (10) | CFP10 | Rv3874 | B1502 | 75-83 | NIRQAGVQY | 1715 | 14[f] | 9 |
| D481 C11 (1) | CFP10 | Rv3874 | B1502 | 75-83 | NIRQAGVQY | 1715 | 14[f] | 13.6 |
| D480 F6 (6) | CFP10 | Rv3874 | B0801 | 3-11 | EMKTDAATL | 387 | 79 | 13.1 |
| D571 B12 (3) | CFP10 | Rv3874 | B4402 | 2-11 | AEMKTDAATL | 31 | 38 | IND |
| D571 E9 (4) | CFP10 | Rv3874 | B4402 | 2-11 | AEMKTDAATL | 31 | 38 | 14 |
| D504 E4 (1) | Mtb9.8 | Rv0287 | A0201 | 3-11 | LLDAHIPQL | <10 | 0.39 | 8 |

TABLE III-continued

Summary of Epitopes Identified

| Clone[a] | Gene | Accession Number | HLA-Restrict Allele | Epitope Locat'n | Epitope Sequence (SEQ ID NO: 26-38) | #SFU[b] | MHC Bind. Aff[c] | V beta region |
|---|---|---|---|---|---|---|---|---|
| D454 B10 (1) | Mtb9.8 | Rv0287 | B0801 | 53-61 | AAHARFVAA | 88 | 0.22 | IND |
| D454 H1-2 (1) | Mtb8.4 | Rv1174c | B1501 | 5-15 | AVINTTCNYGQ | 24 | 10 | 7.1 |
| D432 A3 (2) | Mtb 8.4 | Rv1174c | B3514 | 32-40 | ASPVAQSYL | 210 | 127[e] | 14 |
| D443 H9 (1) | Ag85 B | Rv1886c | TBD | 144-153 | ELPQWLSANR | <10 | NA | 22 |

[a]Number of sister clones is in parentheses.
[b]# of SFU/250,000 CD8+ T cells is shown.
[c]IC50 in nm is shown.
[d]Published previously J Immunol. 2001 Jan 1; 166(1): 439-46.
[e]Measured binding affinity to B3501 is shown.
[f]Measured binding affinity to B1501 is shown.
NA = Not Available.
IND = Indeterminate
TBD = To be done.

Figure 5:
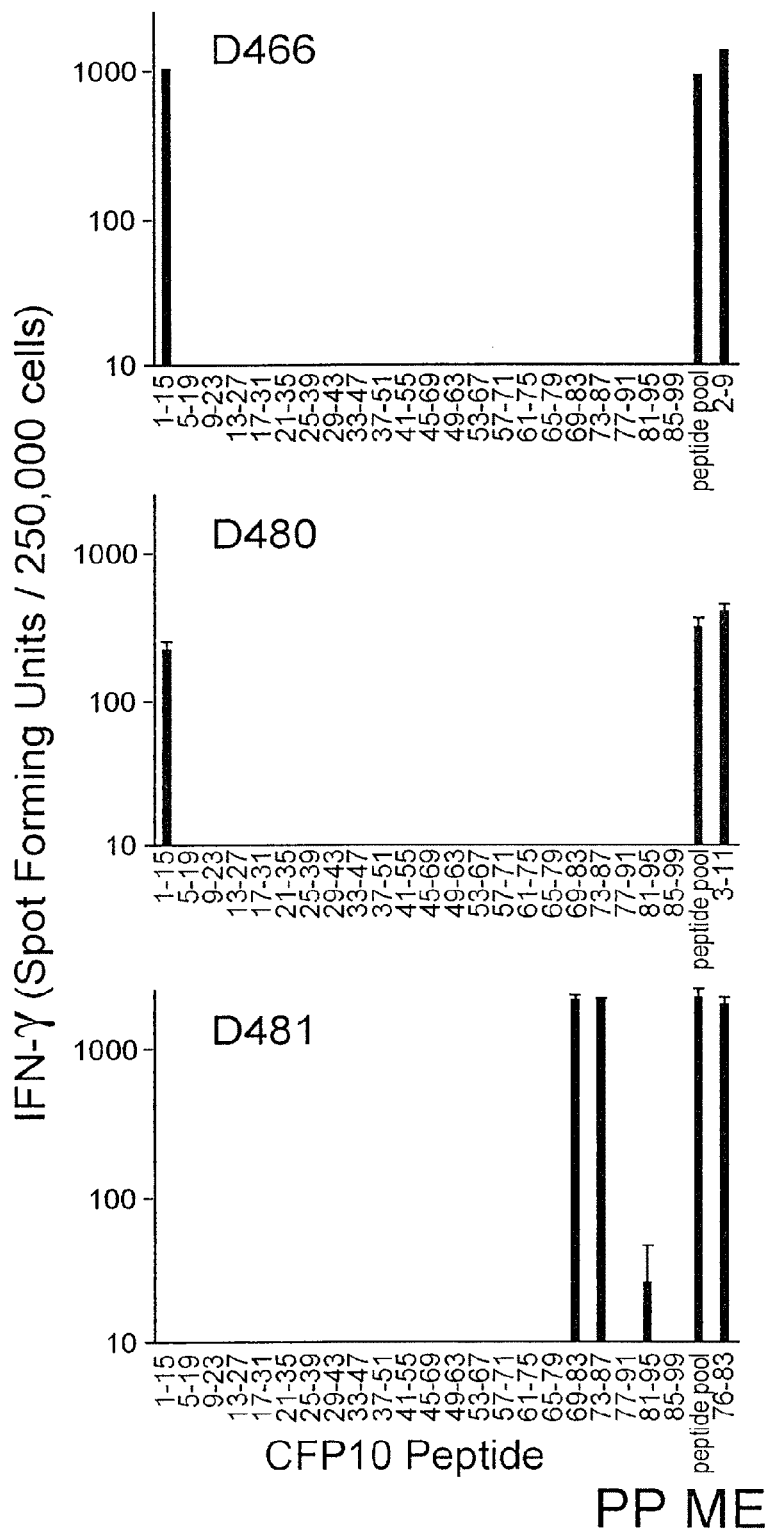
FIG. 5 is a set of bar graphs showing the profiling of the immunodominance pattern for CFP10. To determine the effector cell frequencies, autologous DC (20,000/well) were pulsed either with each individual 15-mer peptide (5 µg/ml), the peptide pool (PP; 5 µg/each peptide) or the minimal epitope (ME) determined from T cell clones derived from each donor (D466:CFP10$_{2-11}$; D480:CFP10$_{3-11}$; D481: CFP10$_{75-83}$; 5 µg/ml), and tested against 250,000 magnetic bead purified CD8+ T cells. IFN-γ release was assessed by ELISPOT after eighteen hours of co-culture. Each point represents the mean of duplicate determinations.
Figure 6A:
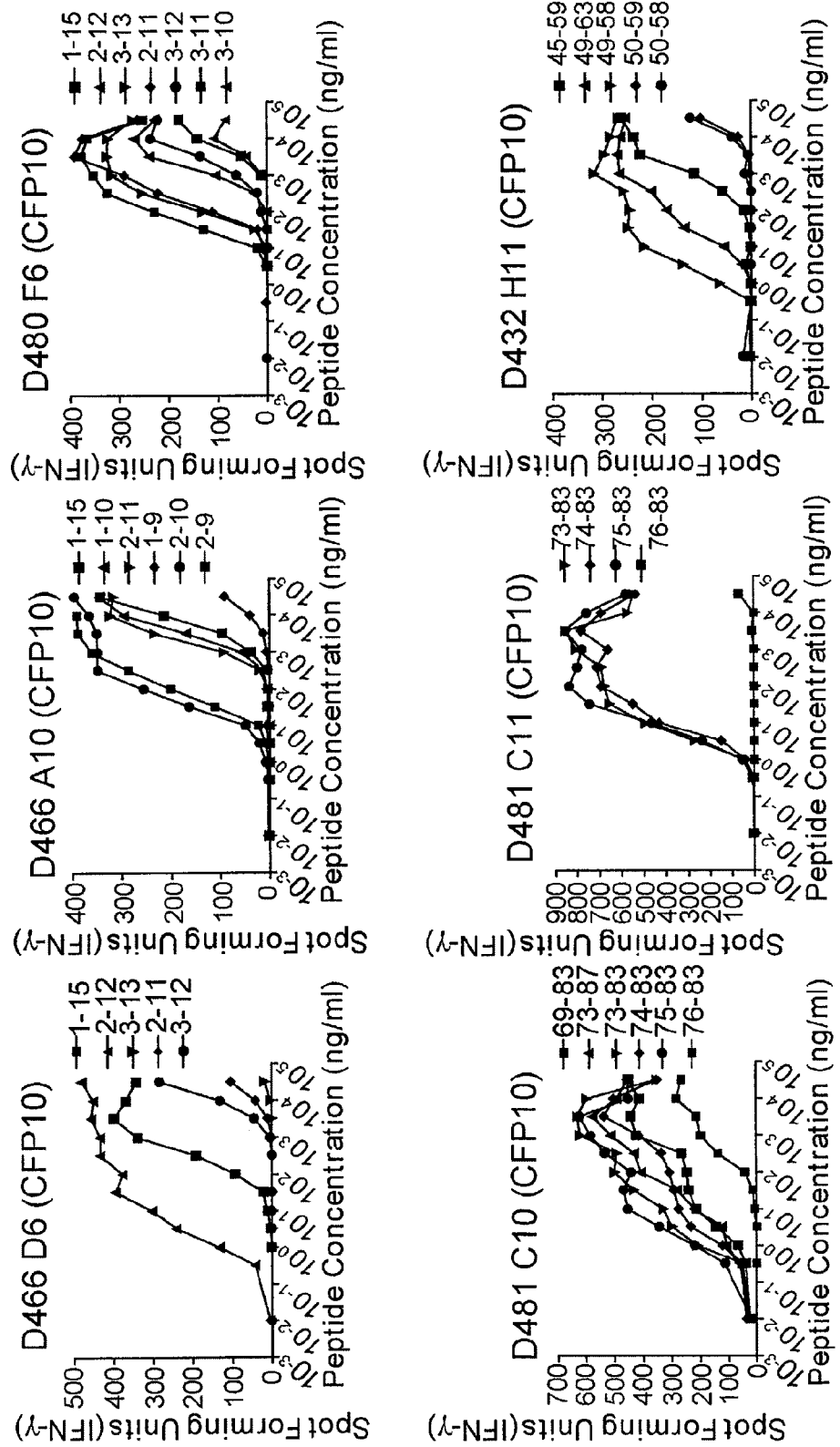
FIGS. 6a and 6b are sets of graphs summarizing the minimal epitope mapping data. To determine the minimal epitope, autologous LCL (20,000/well) was pulsed with peptide at the concentration indicated and co-cultured with T-cells (1000 cells/well). IFN-γ was assessed by ELISPOT after eighteen hours co-culture. Each point represents the mean of duplicate determinations.
Figure 6B:
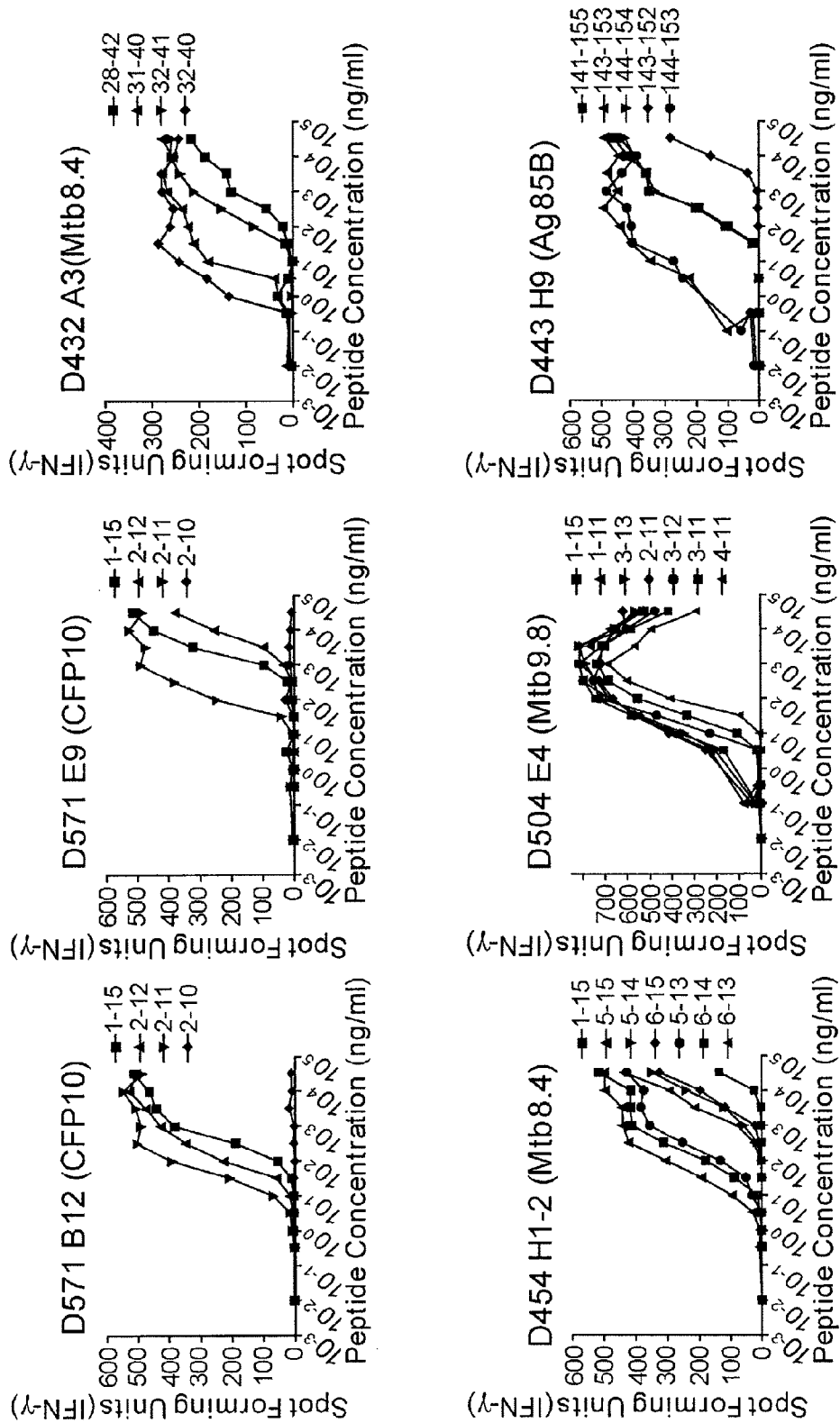
Figure 7:
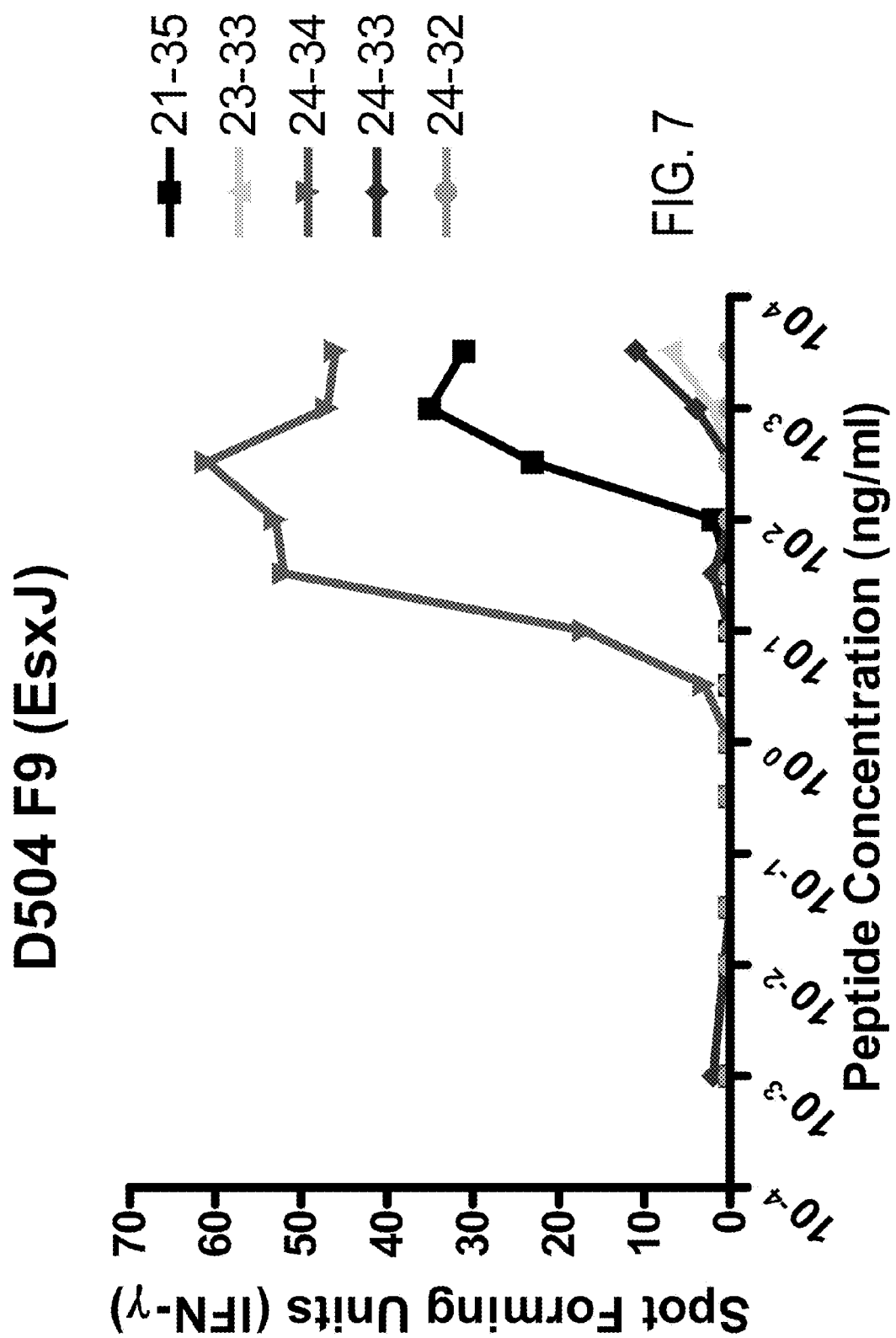
FIG. 7 is a line graph showing the mapping of Minimal Epitope for D504 Clones. To determine the minimal epitope, autologous LCL (20,000/well) was co-cultured with T-cell clones (1,000 cells/well) and the peptide at the concentration indicated. IFN-γ was assessed by ELISPOT after eighteen hours co-culture. Each point represents the mean of duplicate determinations. The spot forming units for peptides with amino acids 21-35, 23-33, 24-34, 24-33 and 24-32 are shown.

Because each of the individual CD8+ T cell clones were derived based on growth of Mtb-infected DC, it was determined whether or not the antigen and epitopes identified reflected immunodominant epitopes ex vivo. Two independent approaches were pursued, the first to determine if the response was present at high frequency, and the second to determine what proportion of the total response to the antigen is constituted by the epitope. To determine the ex-vivo effector cell frequency, as described in FIG. 1, each epitope was tested using autologous DC and magnetic bead purified CD8+ T cells derived from the donor from whom the T cell clones was isolated. A summary of the effector cell frequencies is presented in Table III. For the majority, the epitopes reflect high frequency responses, and thus could be considered a response that has been primed by exposure to Mtb. Notably, T cell clones isolated from four donors recognized CFP10. To determine if the epitopes defined reflected a substantial proportion of the total response to the antigen of interest, magnetic bead purified CD8+ T cells from three donors with sufficient available peripheral blood mononuclear cells (PBMC) were tested for reactivity to each individual 15-mer peptide, the peptide pool, and peptide representing the minimal epitope. As is demonstrated in FIG. 5, the ex vivo frequencies to the minimal epitope, 15-mer peptide(s) containing the minimal epitope, and peptide pool were remarkably concordant. These data suggested that for each donor a dominance hierarchy has been clearly established, and is reflected in the original clones. Finally, as is noted in Table III, daughter clones of identical specificity were frequently identified, a result that would be predicted based on an immundominance hierarchy. TCR V beta staining was used to confirm the clonal relationship between daughter clones. Interestingly, in two cases, the identical minimal epitope and HLA-restriction was represented by two distinct clones (Table III).

Because much work on human CD8+ T cell responses to Mtb has relied upon the use of HLA-prediction algorithms, as each epitope was defined we asked whether or not the epitopes would have been predicted by these approaches. Many of these epitopes were not ranked strongly. This might highlight the limitations of those algorithms at the time they were used. To address this question experimentally, the $IC_{50}$ for each peptide that had been synthesized in the course of definition of the minimal epitope was determined against a panel of human HLA molecules. Shown in Table III is the $IC_{50}$ for the minimal epitope with the cognate restricting allele. The data demonstrated that the T cell epitopes bound avidly to HLA, and show a high degree of concordance between the T cell epitope data and HLA-binding data.

The data demonstrated that CD8+ T cell responses are present in persons infected with Mtb at frequencies that are comparable to that seen following many common viral infections such as vaccinia, influenza, and CMV. All but one of the epitopes that were mapped were restricted by HLA-B molecules. The data suggest that by using a T cell driven approach to epitope identification, dominant epitopes can be defined in humans infected with Mtb.

Example 3

Screening of T Cell Clones Against a Genomic Peptide Library

The classically-restricted and non-classically-restricted T cell clones (see Table II above) that did not recognize one of the known Mtb antigen peptide pools (Rv3875, Rv3874, Rv1886c, Rv0287, Rv3763, Rv1174c, Rv1196, Rv1793, Rv2346c, Rv1037c, Rv3619c and Rv1198) were screened against a genomic peptide library. This peptide library represents 389 genes, representing roughly 10% of the Mtb genome. The peptides are 15mers overlapping by 11 for each gene product. 50 nmol of each peptide was synthesized individually and then pooled into 777 pools of 50 peptides in a 96 well format (nine plates). Five blank wells and one well of an irrelevant peptide pool, SW gag, were included on each of the nine plates. To screen the clones against the genomic peptide library, the clones are first expanded and tested against Mtb-infected DCs to ensure that each clone from this particular expansion yields a robust Mtb-specific signal in the ELISPOT assay. Then up to six T cell clones are pooled. For the screen, T cell clones (5,000 cells/well of each clone), autologous DCs (20,000 cells/well), IL-2 (0.5 ng/ml) and the peptide pools (5 ug/ml, individual peptides) were incubated overnight at 37 C in the ELISPOT assay. Only one technical replicate is done per pool because 5000 T cell clones per well with a peptide antigen produced an overwhelmingly positive response, resulting in a definitive result. Six classical clones from D504 were screened against the genomic peptide library, leading to the discovery of a new epitope. This epitope was from a family of four proteins that includes EsxJ, EsxW, EsxK and EsxP. These proteins share 98% homology and differ at only 3 amino acids. There is a fifth member of this family, EsxM (Rv1792), that was not included in the genomic peptide library.

The clones were screened against the individual fifteen-mers for these peptide pools. All six classical clones recognized EsxJ 21-35. This is a region of EsxJ that is identical to the other four members of this family. Next, 9, 10 and 11 mer peptides were made from this 15mer and screened against each clone. The minimal epitope was determined to be EsxJ 24-34. In addition, the HLA restriction was found to be B5701.

Example 4

Additional Screening of T Cell Clones Against a Genomic Peptide Library

Eleven classical clones from D432B were screened against the genomic peptide library described above. The antigen was determined for two clones, which led to the identification of two novel epitopes, PE_PGRS42$_{47-55}$ and PE9$_{53-67}$. The minimal epitope for one clone was determined to be PE_PGRS42$_{47-55}$ and the HLA restriction was found to be B3514. The minimal epitope for the other clone is not yet determined, but is contained in the 15mer PE9$_{53-67}$. The HLA restriction for this clone was found to be B3905.

TABLE IV

Detail of Novel Epitopes from Genomic Peptide Library Screens.

| Clone | Gene | Accession Number | Epitope Location | Epitope | #SFU/ 250,000 CD8+ T-cells | MHC-Restriction | MHC Binding Affinity (IC50 nm) | TCR V beta region |
|---|---|---|---|---|---|---|---|---|
| D504 F9 (6) | Esx* | Rv1038c | 24-34 SEQ ID NO: 2 | QTVEDE-ARRMW | 84 | B5701 | TBD | Indeterminate |
| D432 D8 (1) | PE9 | Rv1088 | 53-67 SEQ ID NO: 7 | RLFNAN-AEEYHA-LSA | TBD | B3905 | TBD | 8 |
| D432 H8 (1) | PE/PGRS42 | Rv2487c | 47-55 SEQ ID NO: 8 | VSAAIAG-LF | TBD | B3514 | TBD | 7.1 |

Number of clones recognizing epitope from each donor in parentheses. *This is a family of proteins that have almost identical sequences. The family consists of Rv1038c, Rv1197, Rv2347, Rv3620c.

TABLE V

Summary of Completed Clone Screens.

| Donor | TB Status | # Classical available (screened) | # Non-Classical available (screened) | # positive wells in screen | # of confirmed hits | # novel epitopes | # classical clones epitope identified | # classical clones epitope NOT identified |
|---|---|---|---|---|---|---|---|---|
| 426 | PPD+ | 1 (1) | 4 (4) | 1 | 0 | 0 | 0 | 1 |
| 431 | Active | 1 (1) | 1 (1) | 1** | 0 | 0 | 0 | 1 |
| 432 | Active | 11 (11) | 14 (7) | 11 | 3 | 2 | 3 | 8 |
| 454 | PPD+ | 1* (0) | 6 (4) | 0 | 0 | 0 | 0 | 0 |
| 466 | Active | 1 (1) | 4 (4) | 1 | 0 | 0 | 0 | 1 |
| 504 | PPD+ | 6 (6) | 9 (9) | 5 | 4 | 1 | 6 | 0 |
| | | 21 (20) | 38 (29) | 18 | 7 | 3 | 9 | 11 |

*The classical clone from D454 did not recognize Mtb upon re-expansion and was not screened against library.
**The classical clones from 426 and 431 were screened together, so there was one positive well between both clones.

Example 5

Screening of Ex Vivo CD8+ T-Cells Against a Genomic Peptide Library

CD8+ T-cells from a LTBI donor, D610 (SE Asian) were screened against the genomic peptide library described above. Each plate of the genomic peptide library was screened in duplicate, for a total of 18 ELISPOT plates per screen. CD8+ T-cells were prepared from cryopreserved PBMC by CD8+ selection using magnetic bead separations. Resulting cell populations contained ≧96% CD8+ T cells. CD8+ T cells (250,000 cells/well), autologous DCs (20,000 cells/well), and IL-2 (0.5 ng/ml) were added to peptide (final 5 ug/ml, individual peptides) in the ELISPOT plates. Five media control wells are included on each plate. For each plate, the mean of these five wells was subtracted from each well of that plate to normalize between plates. Each technical replicate on each plate was then scored. A well was scored positive if the spot forming units (SFU), less the mean of the media wells, was greater than or equal to ten and the SFU was greater than or equal to twice the mean of the media. (Hudgens et al., J. Immunol. Methods 288: 19-34, 2004). This donor responded to the four peptide wells containing EsxJ, EsxW, EsxK and EsxP. CD8+ T-cells were then screened against each 15mer from these peptide pools and found to respond only to EsxJ 21-35, the same region of EsxJ, EsxW, EsxK and EsxP that is described in example 3 above.

Seven additional donors were screened against the genomic peptide library. The top 10 responses are detailed in Table 7. The four peptide pools highlighted in yellow contain peptides from only one gene. These four genes contain four novel epitopes.

TABLE 7

Top 10 Responses from Peptide Pool Screens of Seven Donors. Spot Forming Units are for 250,000 CD8+ T-cells.

| Peptide Pool | Donor | Average SFU | RvNumbers Represented in Wells | Functional Category |
|---|---|---|---|---|
| C09_1 | D560 | 208.2 | Rv1860(50): | cell wall and cell processes |
| C12_4 | D545 | 156.4 | Rv0468(27): Rv0456c(23): | lipid metabolism |
| A04_3 | D454 | 136 | Rv0284(17): Rv0288(11): Rv0287(22) | cell wall and cell processes |
| B10_3 | D560 | 112.3 | Rv1273c(50): | cell wall and cell processes |
| E04_4 | D560 | 78.2 | Rv0152c(40): Rv0151c(10): | PE/PPE |
| G12_8 | D560 | 77.4 | Rv3478(18): Rv3507(32): | PE/PPE |
| E07_4 | D525 | 76.8 | Rv0159c(50): | PE/PPE |
| A10_8 | D560 | 70.4 | Rv3136(47): Rv3144c(3): | PE/PPE |
| E11_8 | D560 | 66.4 | Rv3350c(50): | PE/PPE |
| E08_9 | D545 | 60.2 | Rv1404(13): Rv2711(37): | regulatory proteins |

Example 6

Animal Models

In tuberculosis research, the mouse model has been used extensively to model various aspects of the disease. Mice can be infected by a variety of routes, including intravenous, intraperitoneal and tracheal. One route is aerosolization of the organism for respiratory infection. The mice are exposed to the aerosol in a chamber (wither whole body or nose only infection). The dose of invention can be varied by manipulating the concentration of Mtb in the nebulizer or time of exposure. A low dose infection, such as about 50 colony forming units (CFU) via aerosol results in a slow and steady increase in bacterial numbers in the lungs, generally reaching a peak in four weeks, which coincides with the peak number of T cells in the lungs. The initial period is considered the acute stage of infection. Following infection, there is a dissemination of bacteria to the mediastinal lymph nodes. T cell priming is generally detectable between two and three weeks. After about four weeks the bacterial numbers stabilize, and there is a slow progressive pathologic response. This system is of use for modeling active infection. Thus, the above-described polypeptides, or polynucleotides encoding these polypeptides, can be administered prior to infection. The ability of the Mtb polypeptides (or polynucleotides encoding these polypeptides) to prevent infection is then assessed. Alternatively, the mice are administered Mtb, and the ability of the Mtb polypeptide (or polynucleotide encoding these polypeptides) to treat the Mtb infection is monitored. The effectiveness of the Mtb polypeptides (or polynucleotides) can be monitored by measuring the T cell response, such as the number of CD8+ or CD4+ T cells, and/or measuring the bacterial numbers, and/or evaluating the pathology.

Exemplary protocols are provided below (see also Repique et al., Infec. Immun. 70: 3318-3323, 2002, incorporated herein by reference for an additional protocol):

A. Short Term Mouse Model:

C57BL/6 mice are vaccinated with a composition including one or more Mtb polypeptide, or a polynucleotide encoding these one or more polypeptides, according to the appropriate protocol and then rested for 4 to 6 weeks. Immunized mice are infected with a low dose aerosol 50-100 CFU) of virulent *M. tuberculosis* and protection is evaluated by assessing the number of viable bacilli 30 days post challenge.

Viable counts are performed on the lung and spleen of mice by homogenizing the organs and plating serial 10-fold dilutions on 7H11 agar plates. Plates are incubated for up to 21 days and the number of colony forming units per organ determined.

BCG vaccinated mice have approximately 1 Log 10 protection in their lung and spleen when compared to PBS-treated mice.

B. Short Term Guinea Pig Model

Out-bred Hartley guinea pigs are vaccinated with a composition including one or more Mtb polypeptide, or a polynucleotide encoding these one or more polypeptides and then rested for 8 to 10 weeks. Immunized guinea pigs are infected with a low dose aerosol (10-30 CFU) of virulent *M. tuberculosis* and protection is evaluated by assessing the number of viable bacilli 30 days post challenge.

Viable counts are performed on the lung and spleen of guinea pigs by homogenizing the organs and plating serial 10-fold dilutions on 7H11 agar plates. Plates are incubated for up to 21 days and the number of colony forming units per organ determined. Lung and spleen segments are also taken for histological analyses.

BCG vaccinated guinea pigs have approximately 2-3 $Log_{10}$ protection in their lung and spleen when compared to PBS-treated guinea pigs. In addition, BCG vaccinated guinea pigs have well defined granulomas when compared to unvaccinated animals.

C. Long Term Guinea Pig Model

The guinea pig model is similar to the mouse model, but the experiments are open-ended survival type and can last for as long as 2 years. Guinea pigs develop 'classical' granulomas similar to humans with active tuberculosis (TB), and as lung tissue necrosis progresses, they begin to lose weight and die of TB similar to humans. The number of colony forming units in the lungs and spleen can be assessed. Histological examination can also be performed to determine the degree of lung involvement and tissue destruction. After low-dose aerosol exposure in the guinea pig the number of organisms increases progressively during the first three weeks and then plateaus into a chronic state. During the later stages of infection there is increased bacterial load in the lung and this is associated with a worsening pathological condition. Without treatment, there is a concomitant rise in both CD4 and CD8 T cells in the lungs of infected guinea pigs.

Out-bred Hartley guinea pigs are vaccinated with the experimental vaccine according to the appropriate protocol and then rested for 8 to 10 weeks. Immunized guinea pigs are then infected with a low dose aerosol (10-30 CFU) of virulent *M. tuberculosis*. Guinea pigs are weighed weekly and monitored daily for signs of disease (such as increased respiration and failure to thrive). Unvaccinated guinea pigs succumb to infection from 20 to 25 weeks post challenge, while BCG vaccinated guinea pigs survive for 50 to 55 weeks post challenge.

At necropsy, the lung and spleen are assessed for the number of CFU and the extent of pathology. The relative protection of the experimental composition is compared to BCG vaccinated animals.

It will be apparent that the precise details of the methods or compositions described may be varied or modified without departing from the spirit of the described invention. We claim all such modifications and variations that fall within the scope and spirit of the claims below.

---

The invention claimed is:

1. A method for producing an immune response to *Mycobacterium tuberculosis* in a subject, comprising administering to the subject a therapeutically effective amount of an isolated polypeptide, wherein the isolated polypeptide comprises the amino acid sequence set forth as SEQ ID NO: 8 thereby inducing an immune response to *Mycobacterium tuberculosis*.

2. The method of claim 1, comprising administering to the subject a therapeutically effective amount of a pharmaceutical composition comprising the isolated polypeptide comprising the amino acid sequence set forth as SEQ ID NO: 8.

3. The method of claim 1, comprising administering to the subject a therapeutically effective amount of an isolated polypeptide consisting of the amino acid sequence set forth as SEQ ID NO: 8.

4. The method of claim 1, comprising administering to the subject a therapeutically effective amount of a pharmaceutical composition comprising an isolated polypeptide consisting of the amino acid sequence set forth as SEQ ID NO: 8 that specifically binds MHC class I.

5. The method of claim 1, further comprising administering to the subject a therapeutically effective amount of an adjuvant.

6. The method of claim 1, wherein the subject is infected with *Mycobacterium tuberculosis* (Mtb).

7. The method of claim 1, wherein the subject is at risk for infection with *Mycobacterium tuberculosis* (Mtb).

8. The method of claim 1, wherein the subject has a latent infection with *Mycobacterium tuberculosis* (Mtb).

9. The method of claim 1, wherein the isolated polypeptide is covalently linked to a carrier.

10. A method for treating a subject infected with *Mycobacterium tuberculosis*, comprising administering to the subject a therapeutically effective amount of an isolated polypeptide, wherein the isolated polypeptide comprises the amino acid sequences set forth as SEQ ID NO: 8 thereby treating the subject infected with *Mycobacterium tuberculosis*.

11. The method of claim 10, wherein the subject infected with *Mycobacterium tuberculosis* does not have a symptom of tuberculosis.

12. The method of claim 10, wherein the isolated polypeptide is covalently linked to a carrier.

13. The method of claim 10, further comprising administering to the subject a therapeutically effective amount of an adjuvant.

14. The method of claim 10, comprising administering to the subject a therapeutically effective amount of a polypeptide consisting of the amino acid sequence set forth as SEQ ID NO: 8.

15. The method of claim 10, wherein the subject is at risk for infection with *Mycobacterium tuberculosis* (Mtb).

16. The method of claim 10, wherein the subject has a latent infection with *Mycobacterium tuberculosis* (Mtb).

17. The method of claim 10, comprising administering to the subject a therapeutically effective amount of a pharmaceutical composition comprising the isolated polypeptide comprising the amino acid sequence set forth as SEQ ID NO: 8.

18. The method of claim 10, comprising administering to the subject a therapeutically effective amount of a pharmaceutical composition consisting of an isolated polypeptide comprising the amino acid sequence set forth as SEQ ID NO: 8.

* * * * *

SEQUENCE LISTING

```
<160> NUMBER OF SEQ ID NOS: 38

<210> SEQ ID NO 1
<211> LENGTH: 97
<212> TYPE: PRT
<213> ORGANISM: Mycobacterium tuberculosis
<220> FEATURE:
<221> NAME/KEY: MISC_FEATURE
<222> LOCATION: (2)..(2)
<223> OTHER INFORMATION: Xaa can be A or T
<220> FEATURE:
<221> NAME/KEY: MISC_FEATURE
<222> LOCATION: (58)..(58)
<223> OTHER INFORMATION: Xaa can be T or A
<220> FEATURE:
<221> NAME/KEY: MISC_FEATURE
<222> LOCATION: (59)..(59)
<223> OTHER INFORMATION: Xaa any amino acid or no amino acid

<400> SEQUENCE: 1

Met Xaa Ser Arg Phe Met Thr Asp Pro His Ala Met Arg Asp Met Ala
1               5                   10                  15

Gly Arg Phe Glu Val His Ala Gln Thr Val Glu Asp Glu Ala Arg Arg
            20                  25                  30

Met Trp Ala Ser Ala Gln Asn Ile Ser Gly Ala Gly Trp Ser Gly Met
        35                  40                  45

Ala Glu Ala Thr Ser Leu Asp Thr Met Xaa Xaa Met Asn Gln Ala Phe
    50                  55                  60

Arg Asn Ile Val Asn Met Leu His Gly Val Arg Asp Gly Leu Val Arg
65                  70                  75                  80

Asp Ala Asn Asn Tyr Glu Gln Gln Glu Gln Ala Ser Gln Gln Ile Leu
                85                  90                  95

Ser

<210> SEQ ID NO 2
<211> LENGTH: 97
<212> TYPE: PRT
<213> ORGANISM: Mycobacterium tuberculosis
```

<400> SEQUENCE: 2

Met Ala Ser Arg Phe Met Thr Asp Pro His Ala Met Arg Asp Met Ala
1               5                   10                  15

Gly Arg Phe Glu Val His Ala Gln Thr Val Glu Asp Glu Ala Arg Arg
            20                  25                  30

Met Trp Ala Ser Ala Gln Asn Ile Ser Gly Ala Gly Trp Ser Gly Met
        35                  40                  45

Ala Glu Ala Thr Ser Leu Asp Thr Met Thr Gln Met Asn Gln Ala Phe
    50                  55                  60

Arg Asn Ile Val Asn Met Leu His Gly Val Arg Asp Gly Leu Val Arg
65                  70                  75                  80

Asp Ala Asn Asn Tyr Glu Gln Gln Glu Gln Ala Ser Gln Gln Ile Leu
                85                  90                  95

Ser

<210> SEQ ID NO 3
<211> LENGTH: 98
<212> TYPE: PRT
<213> ORGANISM: Mycobacterium tuberculosis

<400> SEQUENCE: 3

Met Ala Ser Arg Phe Met Thr Asp Pro His Ala Met Arg Asp Met Ala
1               5                   10                  15

Gly Arg Phe Glu Val His Ala Gln Thr Val Glu Asp Glu Ala Arg Arg
            20                  25                  30

Met Trp Ala Ser Ala Gln Asn Ile Ser Gly Ala Gly Trp Ser Gly Met
        35                  40                  45

Ala Glu Ala Thr Ser Leu Asp Thr Met Ala Gln Met Asn Gln Ala Phe
    50                  55                  60

Arg Asn Ile Val Asn Met Leu His Gly Val Arg Asp Gly Leu Val Arg
65                  70                  75                  80

Asp Ala Asn Asn Tyr Glu Gln Gln Glu Gln Ala Ser Gln Gln Ile Leu
                85                  90                  95

Ser Ser

<210> SEQ ID NO 4
<211> LENGTH: 97
<212> TYPE: PRT
<213> ORGANISM: Mycobacterium tuberculosis

<400> SEQUENCE: 4

Met Ala Ser Arg Phe Met Thr Asp Pro His Ala Met Arg Asp Met Ala
1               5                   10                  15

Gly Arg Phe Glu Val His Ala Gln Thr Val Glu Asp Glu Ala Arg Arg
            20                  25                  30

Met Trp Ala Ser Ala Gln Asn Ile Ser Gly Ala Gly Trp Ser Gly Met
        35                  40                  45

Ala Glu Ala Thr Ser Leu Asp Thr Met Thr Met Asn Gln Ala Phe Arg
    50                  55                  60

Asn Ile Val Asn Met Leu His Gly Val Arg Asp Gly Leu Val Arg Asp
65                  70                  75                  80

Ala Asn Asn Tyr Glu Gln Gln Glu Gln Ala Ser Gln Gln Ile Leu Ser
                85                  90                  95

Ser

```
<210> SEQ ID NO 5
<211> LENGTH: 98
<212> TYPE: PRT
<213> ORGANISM: Mycobacterium tuberculosis

<400> SEQUENCE: 5

Met Ala Thr Arg Phe Met Thr Asp Pro His Ala Met Arg Asp Met Ala
1               5                   10                  15

Gly Arg Phe Glu Val His Ala Gln Thr Val Glu Asp Glu Ala Arg Arg
            20                  25                  30

Met Trp Ala Ser Ala Gln Asn Ile Ser Gly Ala Gly Trp Ser Gly Met
        35                  40                  45

Ala Glu Ala Thr Ser Leu Asp Thr Met Ala Gln Met Asn Gln Ala Phe
    50                  55                  60

Arg Asn Ile Val Asn Met Leu His Gly Val Arg Asp Gly Leu Val Arg
65                  70                  75                  80

Asp Ala Asn Asn Tyr Glu Gln Gln Glu Gln Ala Ser Gln Gln Ile Leu
                85                  90                  95

Ser Ser

<210> SEQ ID NO 6
<211> LENGTH: 98
<212> TYPE: PRT
<213> ORGANISM: Mycobacterium tuberculosis

<400> SEQUENCE: 6

Met Thr Ser Arg Phe Met Thr Asp Pro His Ala Met Arg Asp Met Ala
1               5                   10                  15

Gly Arg Phe Glu Val His Ala Gln Thr Val Glu Asp Glu Ala Arg Arg
            20                  25                  30

Met Trp Ala Ser Ala Gln Asn Ile Ser Gly Ala Gly Trp Ser Gly Met
        35                  40                  45

Ala Glu Ala Thr Ser Leu Asp Thr Met Thr Gln Met Asn Gln Ala Phe
    50                  55                  60

Arg Asn Ile Val Asn Met Leu His Gly Val Arg Asp Gly Leu Val Arg
65                  70                  75                  80

Asp Ala Asn Asn Tyr Glu Gln Gln Glu Gln Ala Ser Gln Gln Ile Leu
                85                  90                  95

Ser Ser

<210> SEQ ID NO 7
<211> LENGTH: 144
<212> TYPE: PRT
<213> ORGANISM: Mycobacterium tuberculosis

<400> SEQUENCE: 7

Met Ser Tyr Met Ile Ala Thr Pro Ala Ala Leu Thr Ala Ala Ala Thr
1               5                   10                  15

Asp Ile Asp Gly Ile Gly Ser Ala Val Ser Val Ala Asn Ala Ala Ala
            20                  25                  30

Val Ala Ala Thr Thr Gly Val Leu Ala Ala Gly Gly Asp Glu Val Leu
        35                  40                  45

Ala Ala Ile Ala Arg Leu Phe Asn Ala Asn Ala Glu Glu Tyr His Ala
    50                  55                  60

Leu Ser Ala Gln Val Ala Ala Phe Gln Thr Leu Phe Val Arg Thr Leu
65                  70                  75                  80

Thr Gly Gly Cys Gly Val Phe Arg Arg Arg Gly Arg Gln Cys Val
                85                  90                  95
```

```
Thr Ala Ala Glu His Arg Ala Ala Gly Ala Gly Arg Gln Arg Arg
            100                 105                 110

Arg Arg Ser Gly Asp Gly Gln Trp Arg Leu Arg Gln Gln Arg His Phe
        115                 120                 125

Gly Cys Gly Gly Gln Pro Glu Phe Arg Gln His Ser Glu His Arg Arg
130                 135                 140

<210> SEQ ID NO 8
<211> LENGTH: 694
<212> TYPE: PRT
<213> ORGANISM: Mycobacterium tuberculosis

<400> SEQUENCE: 8

Val Ser Leu Val Ile Ala Thr Pro Gln Leu Leu Ala Thr Ala Ala Leu
1               5                   10                  15

Asp Leu Ala Ser Ile Gly Ser Gln Val Ser Ala Ala Asn Ala Ala Ala
            20                  25                  30

Ala Met Pro Thr Thr Glu Val Ala Ala Ala Ala Asp Glu Val Ser
        35                  40                  45

Ala Ala Ile Ala Gly Leu Phe Gly Ala His Ala Arg Gln Tyr Gln Ala
    50                  55                  60

Leu Ser Val Gln Val Ala Ala Phe His Glu Gln Phe Val Gln Ala Leu
65                  70                  75                  80

Thr Ala Ala Ala Gly Arg Tyr Ala Ser Thr Glu Ala Ala Val Glu Arg
                85                  90                  95

Ser Leu Leu Gly Ala Val Asn Ala Pro Thr Glu Ala Leu Leu Gly Arg
            100                 105                 110

Pro Leu Ile Gly Asn Gly Ala Asp Gly Thr Ala Pro Gly Gln Pro Gly
        115                 120                 125

Ala Ala Gly Gly Leu Leu Phe Gly Asn Gly Gly Asn Gly Ala Ala Gly
    130                 135                 140

Gly Phe Gly Gln Thr Gly Gly Ser Gly Gly Ala Ala Gly Leu Ile Gly
145                 150                 155                 160

Asn Gly Gly Asn Gly Gly Ala Gly Gly Thr Gly Ala Ala Gly Gly Ala
                165                 170                 175

Gly Gly Asn Gly Gly Trp Leu Trp Gly Asn Gly Gly Asn Gly Gly Val
            180                 185                 190

Gly Gly Thr Ser Val Ala Ala Gly Ile Gly Gly Ala Gly Gly Asn Gly
        195                 200                 205

Gly Asn Ala Gly Leu Phe Gly His Gly Gly Ala Gly Gly Thr Gly Gly
    210                 215                 220

Ala Gly Leu Ala Gly Ala Asn Gly Val Asn Pro Thr Pro Gly Pro Ala
225                 230                 235                 240

Ala Ser Thr Gly Asp Ser Pro Ala Asp Val Ser Gly Ile Gly Asp Gln
                245                 250                 255

Thr Gly Gly Asp Gly Gly Thr Gly Gly His Gly Thr Ala Gly Thr Pro
            260                 265                 270

Thr Gly Gly Thr Gly Gly Asp Gly Ala Thr Ala Thr Ala Gly Ser Gly
        275                 280                 285

Lys Ala Thr Gly Ala Gly Gly Asp Gly Gly Thr Ala Ala Ala Gly
    290                 295                 300

Gly Gly Gly Gly Asn Gly Gly Asp Gly Val Ala Gln Gly Asp Ile
305                 310                 315                 320

Ala Ser Ala Phe Gly Gly Asp Gly Gly Asn Gly Ser Asp Gly Val Ala
                325                 330                 335
```

```
Ala Gly Ser Gly Gly Ser Gly Gly Ala Gly Gly Ala Phe Val
        340                 345                 350

His Ile Ala Thr Ala Thr Ser Thr Gly Gly Ser Gly Gly Phe Gly Gly
            355                 360                 365

Asn Gly Ala Ala Ser Ala Ser Gly Ala Asp Gly Gly Ala Gly Gly
        370                 375                 380

Ala Gly Gly Asn Gly Gly Ala Gly Gly Leu Leu Phe Gly Asp Gly Gly
385                 390                 395                 400

Asn Gly Gly Ala Gly Gly Ala Gly Gly Ile Gly Gly Asp Gly Ala Thr
        405                 410                 415

Gly Gly Pro Gly Gly Ser Gly Gly Asn Ala Gly Ile Ala Arg Phe Asp
        420                 425                 430

Ser Pro Asp Pro Glu Ala Glu Pro Asp Val Val Gly Gly Lys Gly Gly
        435                 440                 445

Asp Gly Gly Lys Gly Gly Ser Gly Leu Gly Val Gly Gly Ala Gly Gly
        450                 455                 460

Thr Gly Gly Ala Gly Gly Asn Gly Gly Ala Gly Gly Leu Leu Phe Gly
465                 470                 475                 480

Asn Gly Gly Asn Gly Gly Asn Ala Gly Ala Gly Gly Asp Gly Gly Ala
            485                 490                 495

Gly Val Ala Gly Gly Val Gly Gly Asn Gly Gly Gly Gly Thr Ala
        500                 505                 510

Thr Phe His Glu Asp Pro Val Ala Gly Val Trp Ala Val Gly Gly Val
            515                 520                 525

Gly Gly Asp Gly Gly Ser Gly Gly Ser Ser Leu Gly Val Gly Gly Val
        530                 535                 540

Gly Gly Ala Gly Gly Val Gly Gly Lys Gly Gly Ala Ser Gly Met Leu
545                 550                 555                 560

Ile Gly Asn Gly Gly Asn Gly Gly Ser Gly Val Gly Gly Ala Gly
            565                 570                 575

Gly Val Gly Gly Ala Gly Gly Asp Gly Gly Asn Gly Ser Gly Gly
        580                 585                 590

Asn Ala Ser Thr Phe Gly Asp Glu Asn Ser Ile Gly Gly Ala Gly Gly
        595                 600                 605

Thr Gly Gly Asn Gly Gly Asn Gly Ala Asn Gly Gly Asn Gly Gly Ala
        610                 615                 620

Gly Gly Ile Ala Gly Gly Ala Gly Gly Ser Gly Gly Phe Leu Ser Gly
625                 630                 635                 640

Ala Ala Gly Val Ser Gly Ala Asp Gly Ile Gly Gly Ala Gly Gly Ala
            645                 650                 655

Gly Gly Ala Gly Gly Ala Gly Gly Ser Gly Gly Glu Ala Gly Ala Gly
        660                 665                 670

Gly Leu Thr Asn Gly Pro Gly Ser Pro Gly Val Ser Gly Thr Glu Gly
        675                 680                 685

Met Ala Gly Ala Pro Gly
        690

<210> SEQ ID NO 9
<211> LENGTH: 325
<212> TYPE: PRT
<213> ORGANISM: Mycobacterium tuberculosis

<400> SEQUENCE: 9

Met His Gln Val Asp Pro Asn Leu Thr Arg Arg Lys Gly Arg Leu Ala
1               5                   10                  15
```

```
Ala Leu Ala Ile Ala Ala Met Ala Ser Ala Ser Leu Val Thr Val Ala
             20                  25                  30

Val Pro Ala Thr Ala Asn Ala Asp Pro Glu Pro Ala Pro Pro Val Pro
         35                  40                  45

Thr Thr Ala Ala Ser Pro Ser Thr Ala Ala Pro Pro Ala Pro
 50                      55                  60

Ala Thr Pro Val Ala Pro Pro Pro Ala Ala Ala Asn Thr Pro Asn
 65                  70                  75                  80

Ala Gln Pro Gly Asp Pro Asn Ala Ala Pro Pro Ala Asp Pro Asn
                 85                  90                  95

Ala Pro Pro Pro Pro Val Ile Ala Pro Asn Ala Pro Gln Pro Val Arg
                 100                 105                 110

Ile Asp Asn Pro Val Gly Gly Phe Ser Phe Ala Leu Pro Ala Gly Trp
             115                 120                 125

Val Glu Ser Asp Ala Ala His Phe Asp Tyr Gly Ser Ala Leu Leu Ser
130                 135                 140

Lys Thr Thr Gly Asp Pro Pro Phe Pro Gly Gln Pro Pro Val Ala
145                 150                 155                 160

Asn Asp Thr Arg Ile Val Leu Gly Arg Leu Asp Gln Lys Leu Tyr Ala
                 165                 170                 175

Ser Ala Glu Ala Thr Asp Ser Lys Ala Ala Arg Leu Gly Ser Asp
             180                 185                 190

Met Gly Glu Phe Tyr Met Pro Tyr Pro Gly Thr Arg Ile Asn Gln Glu
             195                 200                 205

Thr Val Ser Leu Asp Ala Asn Gly Val Ser Gly Ser Ala Ser Tyr Tyr
210                 215                 220

Glu Val Lys Phe Ser Asp Pro Ser Lys Pro Asn Gly Gln Ile Trp Thr
225                 230                 235                 240

Gly Val Ile Gly Ser Pro Ala Ala Asn Ala Pro Asp Ala Gly Pro Pro
                 245                 250                 255

Gln Arg Trp Phe Val Val Trp Leu Gly Thr Ala Asn Asn Pro Val Asp
             260                 265                 270

Lys Gly Ala Ala Lys Ala Leu Ala Glu Ser Ile Arg Pro Leu Val Ala
             275                 280                 285

Pro Pro Pro Ala Pro Ala Pro Ala Pro Ala Glu Pro Ala Pro Ala Pro
             290                 295                 300

Ala Pro Ala Gly Glu Val Ala Pro Thr Pro Thr Pro Thr Pro Gln
305                 310                 315                 320

Arg Thr Leu Pro Ala
             325

<210> SEQ ID NO 10
<211> LENGTH: 582
<212> TYPE: PRT
<213> ORGANISM: Mycobacterium tuberculosis

<400> SEQUENCE: 10

Met Leu Leu Ala Leu Leu Arg Gln His Ile Arg Pro Tyr Arg Arg Leu
1               5                   10                  15

Val Ala Met Leu Met Met Leu Gln Leu Val Ser Thr Leu Ala Ser Leu
             20                  25                  30

Tyr Leu Pro Thr Val Asn Ala Ala Ile Val Asp Asp Gly Val Ala Lys
             35                  40                  45

Gly Asp Thr Ala Thr Ile Val Arg Leu Gly Ala Val Met Leu Gly Val
50                  55                  60
```

```
Thr Gly Leu Gln Val Leu Cys Ala Ile Gly Ala Val Tyr Leu Gly Ser
 65                  70                  75                  80

Arg Thr Gly Ala Gly Phe Gly Arg Asp Leu Arg Ser Ala Met Phe Glu
                 85                  90                  95

His Ile Ile Thr Phe Ser Glu Arg Glu Thr Ala Arg Phe Gly Ala Pro
            100                 105                 110

Thr Leu Leu Thr Arg Ser Thr Asn Asp Val Arg Gln Ile Leu Phe Leu
            115                 120                 125

Val Gln Met Thr Ala Thr Val Leu Val Thr Ala Pro Ile Met Cys Val
        130                 135                 140

Gly Gly Ile Ile Met Ala Ile His Gln Glu Ala Ala Leu Thr Trp Leu
145                 150                 155                 160

Leu Leu Val Ser Val Pro Ile Leu Ala Val Ala Asn Tyr Trp Ile Ile
                165                 170                 175

Ser His Met Leu Pro Leu Phe Arg Arg Met Gln Ser Leu Ile Asp Gly
            180                 185                 190

Ile Asn Arg Val Met Arg Asp Gln Leu Ser Gly Val Arg Val Val Arg
        195                 200                 205

Ala Phe Thr Arg Glu Gly Tyr Glu Arg Asp Lys Phe Ala Gln Ala Asn
    210                 215                 220

Thr Ala Leu Ser Asn Ala Ala Leu Ser Ala Gly Asn Trp Gln Ala Leu
225                 230                 235                 240

Met Leu Pro Val Thr Thr Leu Thr Ile Asn Ala Ser Ser Val Ala Leu
                245                 250                 255

Ile Trp Phe Gly Gly Leu Arg Ile Asp Ser Gly Gln Met Gln Val Gly
            260                 265                 270

Ser Leu Ile Ala Phe Leu Ser Tyr Phe Ala Gln Ile Leu Met Ala Val
        275                 280                 285

Leu Met Ala Thr Met Thr Leu Ala Val Leu Pro Arg Ala Ser Val Cys
    290                 295                 300

Ala Glu Arg Ile Thr Glu Val Leu Ser Thr Pro Ala Ala Leu Gly Asn
305                 310                 315                 320

Pro Asp Asn Pro Lys Phe Pro Thr Asp Gly Val Thr Gly Val Val Arg
                325                 330                 335

Leu Ala Gly Ala Thr Phe Thr Tyr Pro Gly Ala Asp Cys Pro Val Leu
            340                 345                 350

Gln Asp Ile Ser Leu Thr Ala Arg Pro Gly Thr Thr Ala Ile Val
        355                 360                 365

Gly Ser Thr Gly Ser Gly Lys Ser Thr Leu Val Ser Leu Ile Cys Arg
    370                 375                 380

Leu Tyr Asp Val Thr Ala Gly Ala Val Leu Val Asp Gly Ile Asp Val
385                 390                 395                 400

Arg Glu Tyr His Thr Glu Arg Leu Trp Ser Ala Ile Gly Leu Val Pro
                405                 410                 415

Gln Arg Ser Tyr Leu Phe Ser Gly Thr Val Ala Asp Asn Leu Arg Tyr
            420                 425                 430

Gly Gly Gly Pro Asp Gln Val Thr Glu Gln Glu Met Trp Glu Ala
        435                 440                 445

Leu Arg Val Ala Ala Ala Asp Gly Phe Val Gln Thr Asp Gly Leu Gln
    450                 455                 460

Thr Arg Val Ala Gln Gly Gly Val Asn Phe Ser Gly Gly Gln Arg Gln
465                 470                 475                 480

Arg Leu Ala Ile Ala Arg Ala Val Ile Arg Arg Pro Ala Ile Tyr Val
```

-continued

```
                       485                 490                 495
Phe Asp Asp Ala Phe Ser Ala Leu Asp Val His Thr Asp Ala Lys Val
                500                 505                 510

His Ala Ser Leu Arg Gln Val Ser Gly Asp Ala Thr Ile Ile Val Val
            515                 520                 525

Thr Gln Arg Ile Ser Asn Ala Ala Gln Ala Asp Gln Val Ile Val Val
        530                 535                 540

Asp Asn Gly Lys Ile Val Gly Thr Gly Thr His Glu Thr Leu Leu Ala
545                 550                 555                 560

Asp Cys Pro Thr Tyr Ala Glu Phe Ala Ala Ser Gln Ser Leu Ser Ala
                565                 570                 575

Thr Val Gly Gly Val Gly
            580

<210> SEQ ID NO 11
<211> LENGTH: 468
<212> TYPE: PRT
<213> ORGANISM: Mycobacterium tuberculosis

<400> SEQUENCE: 11

Met Ser Tyr Val Ile Ala Ala Pro Glu Met Leu Ala Thr Thr Ala Ala
1               5                   10                  15

Asp Val Asp Gly Ile Gly Ser Ala Ile Arg Ala Ala Ser Ala Ser Ala
            20                  25                  30

Ala Gly Pro Thr Thr Gly Leu Leu Ala Ala Ala Asp Glu Val Ser
        35                  40                  45

Ser Ala Ala Ala Ala Leu Phe Ser Glu Tyr Ala Arg Glu Cys Gln Glu
    50                  55                  60

Val Leu Lys Gln Ala Ala Ala Phe His Gly Phe Thr Arg Ala Leu
65                  70                  75                  80

Ala Ala Ala Gly Ala Ala Tyr Ala Gln Ala Glu Ala Ser Asn Thr Ala
                85                  90                  95

Ala Met Ser Gly Thr Ala Gly Ser Ser Gly Ala Leu Gly Ser Val Gly
            100                 105                 110

Met Leu Ser Gly Asn Pro Leu Thr Ala Leu Met Met Gly Gly Thr Gly
        115                 120                 125

Glu Pro Ile Leu Ser Asp Arg Val Leu Ala Ile Ile Asp Ser Ala Tyr
    130                 135                 140

Ile Arg Pro Ile Phe Gly Pro Asn Asn Pro Val Ala Gln Tyr Thr Pro
145                 150                 155                 160

Glu Gln Trp Trp Pro Phe Ile Gly Asn Leu Ser Leu Asp Gln Ser Ile
                165                 170                 175

Ala Gln Gly Val Thr Leu Leu Asn Asn Gly Ile Asn Ala Glu Leu Gln
            180                 185                 190

Asn Gly His Asp Val Val Val Phe Gly Tyr Ser Gln Ser Ala Ala Val
        195                 200                 205

Ala Thr Asn Glu Ile Arg Ala Leu Met Ala Leu Pro Pro Gly Gln Ala
    210                 215                 220

Pro Asp Pro Ser Arg Leu Ala Phe Thr Leu Ile Gly Asn Ile Asn Asn
225                 230                 235                 240

Pro Asn Gly Gly Val Leu Glu Arg Tyr Val Gly Leu Tyr Leu Pro Phe
                245                 250                 255

Leu Asp Met Ser Phe Asn Gly Ala Thr Pro Pro Asp Ser Pro Tyr Gln
            260                 265                 270

Thr Tyr Met Tyr Thr Gly Gln Tyr Asp Gly Tyr Ala His Asn Pro Gln
```

275 280 285

Tyr Pro Leu Asn Ile Leu Ser Asp Leu Asn Ala Phe Met Gly Ile Arg
290 295 300

Trp Val His Asn Ala Tyr Pro Phe Thr Ala Ala Glu Val Ala Asn Ala
305 310 315 320

Val Pro Leu Pro Thr Ser Pro Gly Tyr Thr Gly Asn Thr His Tyr Tyr
325 330 335

Met Phe Leu Thr Gln Asp Leu Pro Leu Leu Gln Pro Ile Arg Ala Ile
340 345 350

Pro Phe Val Gly Thr Pro Ile Ala Glu Leu Ile Gln Pro Asp Leu Arg
355 360 365

Val Leu Val Asp Leu Gly Tyr Gly Tyr Gly Tyr Ala Asp Val Pro Thr
370 375 380

Pro Ala Ser Leu Phe Ala Pro Ile Asn Pro Ile Ala Val Ala Ser Ala
385 390 395 400

Leu Ala Thr Gly Thr Val Gln Gly Pro Gln Ala Ala Leu Val Ser Ile
405 410 415

Gly Leu Leu Pro Gln Ser Ala Leu Pro Asn Thr Tyr Pro Tyr Leu Pro
420 425 430

Ser Ala Asn Pro Gly Leu Met Phe Asn Phe Gly Gln Ser Ser Val Thr
435 440 445

Glu Leu Ser Val Leu Ser Gly Ala Leu Gly Ser Val Ala Arg Leu Ile
450 455 460

Pro Pro Ile Ala
465

<210> SEQ ID NO 12
<211> LENGTH: 3716
<212> TYPE: PRT
<213> ORGANISM: Mycobacterium tuberculosis

<400> SEQUENCE: 12

Met Glu Phe Pro Val Leu Pro Pro Glu Ile Asn Ser Val Leu Met Tyr
1 5 10 15

Ser Gly Ala Gly Ser Ser Pro Leu Leu Ala Ala Ala Ala Ala Trp Asp
20 25 30

Gly Leu Ala Glu Glu Leu Gly Ser Ala Ala Val Ser Phe Gly Gln Val
35 40 45

Thr Ser Gly Leu Thr Ala Gly Val Trp Gln Gly Ala Ala Ala Ala Ala
50 55 60

Met Ala Ala Ala Ala Ala Pro Tyr Ala Gly Trp Leu Gly Ser Val Ala
65 70 75 80

Ala Ala Ala Glu Ala Val Ala Gly Gln Ala Arg Val Val Val Gly Val
85 90 95

Phe Glu Ala Ala Leu Ala Ala Thr Val Asp Pro Ala Leu Val Ala Ala
100 105 110

Asn Arg Ala Arg Leu Val Ala Leu Ala Val Ser Asn Leu Leu Gly Gln
115 120 125

Asn Thr Pro Ala Ile Ala Ala Ala Glu Ala Glu Tyr Glu Leu Met Trp
130 135 140

Ala Ala Asp Val Ala Ala Met Ala Gly Tyr His Ser Gly Ala Ser Ala
145 150 155 160

Ala Ala Ala Ala Leu Pro Ala Phe Ser Pro Pro Ala Gln Ala Leu Gly
165 170 175

Gly Gly Val Gly Ala Phe Leu Thr Ala Leu Phe Ala Ser Pro Ala Lys

```
            180                 185                 190
Ala Leu Ser Leu Asn Ala Gly Leu Gly Asn Val Gly Asn Tyr Asn Val
            195                 200                 205
Gly Leu Gly Asn Val Gly Val Phe Asn Leu Gly Ala Gly Asn Val Gly
            210                 215                 220
Gly Gln Asn Leu Gly Phe Gly Asn Ala Gly Gly Thr Asn Val Gly Phe
225                 230                 235                 240
Gly Asn Leu Gly Asn Gly Asn Val Gly Phe Gly Asn Ser Gly Leu Gly
                245                 250                 255
Ala Gly Leu Ala Gly Leu Gly Asn Ile Gly Leu Gly Asn Ala Gly Ser
            260                 265                 270
Ser Asn Tyr Gly Phe Ala Asn Leu Gly Val Gly Asn Ile Gly Phe Gly
            275                 280                 285
Asn Thr Gly Thr Asn Asn Val Gly Val Gly Leu Thr Gly Asn His Leu
            290                 295                 300
Thr Gly Ile Gly Gly Leu Asn Ser Gly Thr Gly Asn Ile Gly Leu Phe
305                 310                 315                 320
Asn Ser Gly Thr Gly Asn Val Gly Phe Phe Asn Ser Gly Thr Gly Asn
                325                 330                 335
Phe Gly Val Phe Asn Ser Gly Asn Tyr Asn Thr Gly Val Gly Asn Ala
            340                 345                 350
Gly Thr Ala Ser Thr Gly Leu Phe Asn Ala Gly Asn Phe Asn Thr Gly
            355                 360                 365
Val Val Asn Val Gly Ser Tyr Asn Thr Gly Ser Phe Asn Ala Gly Asp
            370                 375                 380
Thr Asn Thr Gly Gly Phe Asn Pro Gly Gly Val Asn Thr Gly Trp Leu
385                 390                 395                 400
Asn Thr Gly Asn Thr Asn Thr Gly Ile Ala Asn Ser Gly Asn Val Asn
                405                 410                 415
Thr Gly Ala Phe Ile Ser Gly Asn Phe Asn Asn Gly Val Leu Trp Val
            420                 425                 430
Gly Asp Tyr Gln Gly Leu Phe Gly Val Ser Ala Gly Ser Ser Ile Pro
            435                 440                 445
Ala Ile Pro Ile Gly Leu Val Leu Asn Gly Asp Ile Gly Pro Ile Thr
            450                 455                 460
Ile Gln Pro Ile Pro Ile Leu Pro Thr Ile Pro Leu Ser Ile His Gln
465                 470                 475                 480
Thr Val Asn Leu Gly Pro Leu Val Val Pro Asp Ile Val Ile Pro Ala
                485                 490                 495
Phe Gly Gly Gly Ile Gly Ile Pro Ile Asn Ile Gly Pro Leu Thr Ile
            500                 505                 510
Thr Pro Ile Thr Leu Phe Ala Gln Gln Thr Phe Val Asn Gln Leu Pro
            515                 520                 525
Phe Pro Thr Phe Ser Leu Gly Lys Ile Thr Ile Pro Gln Ile Gln Thr
            530                 535                 540
Phe Asp Ser Asn Gly Gln Leu Val Ser Phe Ile Gly Pro Ile Val Ile
545                 550                 555                 560
Asp Thr Thr Ile Pro Gly Pro Thr Asn Pro Gln Ile Asp Leu Thr Ile
                565                 570                 575
Arg Trp Asp Thr Pro Ile Thr Leu Phe Pro Asn Gly Ile Ser Ala
            580                 585                 590
Pro Asp Asn Pro Leu Gly Leu Leu Val Ser Val Ser Ile Ser Asn Pro
            595                 600                 605
```

```
Gly Phe Thr Ile Pro Gly Phe Ser Val Pro Ala Gln Pro Leu Pro Leu
            610                 615                 620

Ser Ile Asp Ile Glu Gly Gln Ile Asp Gly Phe Ser Thr Pro Pro Ile
625                 630                 635                 640

Thr Ile Asp Arg Ile Pro Leu Thr Val Gly Gly Val Thr Ile Gly
                645                 650                 655

Pro Ile Thr Ile Gln Gly Leu His Ile Pro Ala Ala Pro Gly Val Gly
            660                 665                 670

Asn Thr Thr Thr Ala Pro Ser Ser Gly Phe Phe Asn Ser Gly Ala Gly
            675                 680                 685

Gly Val Ser Gly Phe Gly Asn Val Gly Ala Gly Ser Ser Gly Trp Trp
            690                 695                 700

Asn Gln Ala Pro Ser Ala Leu Leu Gly Ala Gly Ser Gly Val Gly Asn
705                 710                 715                 720

Val Gly Thr Leu Gly Ser Gly Val Leu Asn Leu Gly Ser Gly Ile Ser
                725                 730                 735

Gly Phe Tyr Asn Thr Ser Val Leu Pro Phe Gly Thr Pro Ala Ala Val
            740                 745                 750

Ser Gly Ile Gly Asn Leu Gly Gln Gln Leu Ser Gly Val Ser Ala Ala
            755                 760                 765

Gly Thr Thr Leu Arg Ser Met Leu Ala Gly Asn Leu Gly Leu Ala Asn
            770                 775                 780

Val Gly Asn Phe Asn Thr Gly Phe Gly Asn Val Gly Asp Val Asn Leu
785                 790                 795                 800

Gly Ala Ala Asn Ile Gly Gly His Asn Leu Gly Leu Gly Asn Val Gly
                805                 810                 815

Asp Gly Asn Leu Gly Leu Gly Asn Ile Gly His Gly Asn Leu Gly Phe
            820                 825                 830

Ala Asn Leu Gly Leu Thr Ala Gly Ala Ala Gly Val Gly Asn Val Gly
            835                 840                 845

Phe Gly Asn Ala Gly Ile Asn Asn Tyr Gly Leu Ala Asn Met Gly Val
            850                 855                 860

Gly Asn Ile Gly Phe Ala Asn Thr Gly Thr Gly Asn Ile Gly Ile Gly
865                 870                 875                 880

Leu Val Gly Asp His Arg Thr Gly Ile Gly Gly Leu Asn Ser Gly Ile
                885                 890                 895

Gly Asn Ile Gly Leu Phe Asn Ser Gly Thr Gly Asn Val Gly Phe Phe
            900                 905                 910

Asn Ser Gly Thr Gly Asn Phe Gly Ile Gly Asn Ser Gly Arg Phe Asn
            915                 920                 925

Thr Gly Ile Gly Asn Ser Gly Thr Ala Ser Thr Gly Leu Phe Asn Ala
            930                 935                 940

Gly Ser Phe Ser Thr Gly Ile Ala Asn Thr Gly Asp Tyr Asn Thr Gly
945                 950                 955                 960

Ser Phe Asn Ala Gly Asp Thr Asn Thr Gly Phe Asn Pro Gly Gly
                965                 970                 975

Ile Asn Thr Gly Trp Phe Asn Thr Gly His Ala Asn Thr Gly Leu Ala
            980                 985                 990

Asn Ala Gly Thr Phe Gly Thr Gly Ala Phe Met Thr Gly Asp Tyr Ser
            995                 1000                1005

Asn Gly Leu Leu Trp Arg Gly Gly Tyr Glu Gly Leu Val Gly Val
            1010                1015                1020

Arg Val Gly Pro Thr Ile Ser Gln Phe Pro Val Thr Val His Ala
            1025                1030                1035
```

```
Ile Gly Gly Val Gly Pro Leu His Val Ala Pro Val Pro Val Pro
    1040            1045                1050

Ala Val His Val Glu Ile Thr Asp Ala Thr Val Gly Leu Gly Pro
    1055            1060                1065

Phe Thr Val Pro Pro Ile Ser Ile Pro Ser Leu Pro Ile Ala Ser
    1070            1075                1080

Ile Thr Gly Ser Val Asp Leu Ala Ala Asn Thr Ile Ser Pro Ile
    1085            1090                1095

Arg Ala Leu Asp Pro Leu Ala Gly Ser Ile Gly Leu Phe Leu Glu
    1100            1105                1110

Pro Phe Arg Leu Ser Asp Pro Phe Ile Thr Ile Asp Ala Phe Gln
    1115            1120                1125

Val Val Ala Gly Val Leu Phe Leu Glu Asn Ile Ile Val Pro Gly
    1130            1135                1140

Leu Thr Val Ser Gly Gln Ile Leu Val Thr Pro Thr Pro Ile Pro
    1145            1150                1155

Leu Thr Leu Asn Leu Asp Thr Thr Pro Trp Thr Leu Phe Pro Asn
    1160            1165                1170

Gly Phe Thr Ile Pro Ala Gln Thr Pro Val Thr Val Gly Met Glu
    1175            1180                1185

Val Ala Asn Asp Gly Phe Thr Phe Phe Pro Gly Gly Leu Thr Phe
    1190            1195                1200

Pro Arg Ala Ser Ala Gly Val Thr Gly Leu Ser Val Gly Leu Asp
    1205            1210                1215

Ala Phe Thr Leu Leu Pro Asp Gly Phe Thr Leu Asp Thr Val Pro
    1220            1225                1230

Ala Thr Phe Asp Gly Thr Ile Leu Ile Gly Asp Ile Pro Ile Pro
    1235            1240                1245

Ile Ile Asp Val Pro Ala Val Pro Gly Phe Gly Asn Thr Thr Thr
    1250            1255                1260

Ala Pro Ser Ser Gly Phe Phe Asn Thr Gly Gly Gly Gly Ser
    1265            1270                1275

Gly Phe Ala Asn Val Gly Ala Gly Thr Ser Gly Trp Trp Asn Gln
    1280            1285                1290

Gly His Asp Val Leu Ala Gly Ala Gly Ser Gly Val Ala Asn Ala
    1295            1300                1305

Gly Thr Leu Ser Ser Gly Val Leu Asn Val Gly Ser Gly Ile Ser
    1310            1315                1320

Gly Trp Tyr Asn Thr Ser Thr Leu Gly Ala Gly Thr Pro Ala Val
    1325            1330                1335

Val Ser Gly Ile Gly Asn Leu Gly Gln Gln Leu Ser Gly Phe Leu
    1340            1345                1350

Ala Asn Gly Thr Val Leu Asn Arg Ser Pro Ile Val Asn Ile Gly
    1355            1360                1365

Trp Ala Asp Val Gly Ala Phe Asn Thr Gly Leu Gly Asn Val Gly
    1370            1375                1380

Asp Leu Asn Trp Gly Ala Ala Asn Ile Gly Ala Gln Asn Leu Gly
    1385            1390                1395

Leu Gly Asn Leu Gly Ser Gly Asn Val Gly Phe Gly Asn Ile Gly
    1400            1405                1410

Ala Gly Asn Val Gly Phe Ala Asn Ser Gly Pro Ala Val Gly Leu
    1415            1420                1425

Ala Gly Leu Gly Asn Val Gly Leu Ser Asn Ala Gly Ser Asn Asn
```

```
                      1430              1435              1440
Trp  Gly  Leu  Ala  Asn  Leu  Gly  Val  Gly  Asn  Ile  Gly  Leu  Ala  Asn
          1445                    1450                    1455
Thr  Gly  Thr  Gly  Asn  Ile  Gly  Ile  Gly  Leu  Val  Gly  Asp  Tyr  Gln
     1460                    1465                    1470
Thr  Gly  Ile  Gly  Gly  Leu  Asn  Ser  Gly  Ser  Gly  Asn  Ile  Gly  Leu
     1475                    1480                    1485
Phe  Asn  Ser  Gly  Thr  Gly  Asn  Val  Gly  Phe  Phe  Asn  Thr  Gly  Thr
     1490                    1495                    1500
Gly  Asn  Phe  Gly  Leu  Phe  Asn  Ser  Gly  Ser  Phe  Asn  Thr  Gly  Ile
     1505                    1510                    1515
Gly  Asn  Ser  Gly  Thr  Gly  Ser  Thr  Gly  Leu  Phe  Asn  Ala  Gly  Asn
     1520                    1525                    1530
Phe  Asn  Thr  Gly  Ile  Ala  Asn  Pro  Gly  Ser  Tyr  Asn  Thr  Gly  Ser
     1535                    1540                    1545
Phe  Asn  Val  Gly  Asp  Thr  Asn  Thr  Gly  Gly  Phe  Asn  Pro  Gly  Asp
     1550                    1555                    1560
Ile  Asn  Thr  Gly  Trp  Phe  Asn  Thr  Gly  Ile  Met  Asn  Thr  Gly  Thr
     1565                    1570                    1575
Arg  Asn  Thr  Gly  Ala  Leu  Met  Ser  Gly  Thr  Asp  Ser  Asn  Gly  Met
     1580                    1585                    1590
Leu  Trp  Arg  Gly  Asp  His  Glu  Gly  Leu  Phe  Gly  Leu  Ser  Tyr  Gly
     1595                    1600                    1605
Ile  Thr  Ile  Pro  Gln  Phe  Pro  Ile  Arg  Ile  Thr  Thr  Thr  Gly  Gly
     1610                    1615                    1620
Ile  Gly  Pro  Ile  Val  Ile  Pro  Asp  Thr  Thr  Ile  Leu  Pro  Pro  Leu
     1625                    1630                    1635
His  Leu  Gln  Ile  Thr  Gly  Asp  Ala  Asp  Tyr  Ser  Phe  Thr  Val  Pro
     1640                    1645                    1650
Asp  Ile  Pro  Ile  Pro  Ala  Ile  His  Ile  Gly  Ile  Asn  Gly  Val  Val
     1655                    1660                    1665
Thr  Val  Gly  Phe  Thr  Ala  Pro  Glu  Ala  Thr  Leu  Leu  Ser  Ala  Leu
     1670                    1675                    1680
Lys  Asn  Asn  Gly  Ser  Phe  Ile  Ser  Phe  Gly  Pro  Ile  Thr  Leu  Ser
     1685                    1690                    1695
Asn  Ile  Asp  Ile  Pro  Pro  Met  Asp  Phe  Thr  Leu  Gly  Leu  Pro  Val
     1700                    1705                    1710
Leu  Gly  Pro  Ile  Thr  Gly  Gln  Leu  Gly  Pro  Ile  His  Leu  Glu  Pro
     1715                    1720                    1725
Ile  Val  Val  Ala  Gly  Ile  Gly  Val  Pro  Leu  Glu  Ile  Glu  Pro  Ile
     1730                    1735                    1740
Pro  Leu  Asp  Ala  Ile  Ser  Leu  Ser  Glu  Ser  Ile  Pro  Ile  Arg  Ile
     1745                    1750                    1755
Pro  Val  Asp  Ile  Pro  Ala  Ser  Val  Ile  Asp  Gly  Ile  Ser  Met  Ser
     1760                    1765                    1770
Glu  Val  Val  Pro  Ile  Asp  Ala  Ser  Val  Asp  Ile  Pro  Ala  Val  Thr
     1775                    1780                    1785
Ile  Thr  Gly  Thr  Thr  Ile  Ser  Ala  Ile  Pro  Leu  Gly  Phe  Asp  Ile
     1790                    1795                    1800
Arg  Thr  Ser  Ala  Gly  Pro  Leu  Asn  Ile  Pro  Ile  Ile  Asp  Ile  Pro
     1805                    1810                    1815
Ala  Ala  Pro  Gly  Phe  Gly  Asn  Ser  Thr  Gln  Met  Pro  Ser  Ser  Gly
     1820                    1825                    1830
```

```
Phe Phe Asn Thr Gly Ala Gly Gly Ser Gly Ile Gly Asn Leu
1835             1840                1845

Gly Ala Gly Val Ser Gly Leu Leu Asn Gln Ala Gly Ala Gly Ser
1850             1855                1860

Leu Val Gly Thr Leu Ser Gly Leu Gly Asn Ala Gly Thr Leu Ala
1865             1870                1875

Ser Gly Val Leu Asn Ser Gly Thr Ala Ile Ser Gly Leu Phe Asn
1880             1885                1890

Val Ser Thr Leu Asp Ala Thr Thr Pro Ala Val Ile Ser Gly Phe
1895             1900                1905

Ser Asn Leu Gly Asp His Met Ser Gly Val Ser Ile Asp Gly Leu
1910             1915                1920

Ile Ala Ile Leu Thr Phe Pro Pro Ala Glu Ser Val Phe Asp Gln
1925             1930                1935

Ile Ile Asp Ala Ala Ile Ala Glu Leu Gln His Leu Asp Ile Gly
1940             1945                1950

Asn Ala Leu Ala Leu Gly Asn Val Gly Gly Val Asn Leu Gly Leu
1955             1960                1965

Ala Asn Val Gly Glu Phe Asn Leu Gly Ala Gly Asn Val Gly Asn
1970             1975                1980

Ile Asn Val Gly Ala Gly Asn Leu Gly Gly Ser Asn Leu Gly Leu
1985             1990                1995

Gly Asn Val Gly Thr Gly Asn Leu Gly Phe Gly Asn Ile Gly Ala
2000             2005                2010

Gly Asn Phe Gly Phe Gly Asn Ala Gly Leu Thr Ala Gly Ala Gly
2015             2020                2025

Gly Leu Gly Asn Val Gly Leu Gly Asn Ala Gly Ser Gly Ser Trp
2030             2035                2040

Gly Leu Ala Asn Val Gly Val Gly Asn Ile Gly Leu Ala Asn Thr
2045             2050                2055

Gly Thr Gly Asn Ile Gly Ile Gly Leu Thr Gly Asp Tyr Arg Thr
2060             2065                2070

Gly Ile Gly Gly Leu Asn Ser Gly Thr Gly Asn Leu Gly Leu Phe
2075             2080                2085

Asn Ser Gly Thr Gly Asn Ile Gly Phe Phe Asn Thr Gly Thr Gly
2090             2095                2100

Asn Phe Gly Leu Phe Asn Ser Gly Ser Tyr Ser Thr Gly Val Gly
2105             2110                2115

Asn Ala Gly Thr Ala Ser Thr Gly Leu Phe Asn Ala Gly Asn Phe
2120             2125                2130

Asn Thr Gly Leu Ala Asn Ala Gly Ser Tyr Asn Thr Gly Ser Leu
2135             2140                2145

Asn Val Gly Ser Phe Asn Thr Gly Gly Val Asn Pro Gly Thr Val
2150             2155                2160

Asn Thr Gly Trp Phe Asn Thr Gly His Thr Asn Thr Gly Leu Phe
2165             2170                2175

Asn Thr Gly Asn Val Asn Thr Gly Ala Phe Asn Ser Gly Ser Phe
2180             2185                2190

Asn Asn Gly Ala Leu Trp Thr Gly Asp Tyr His Gly Leu Val Gly
2195             2200                2205

Phe Ser Phe Ser Ile Asp Ile Ala Gly Ser Thr Leu Leu Asp Leu
2210             2215                2220

Asn Glu Thr Leu Asn Leu Gly Pro Ile His Ile Glu Gln Ile Asp
2225             2230                2235
```

```
Ile Pro Gly Met Ser Leu Phe Asp Val His Glu Ile Val Glu Ile
    2240                2245                2250

Gly Pro Phe Thr Ile Pro Gln Val Asp Val Pro Ala Ile Pro Leu
    2255                2260                2265

Glu Ile His Glu Ser Ile His Met Asp Pro Ile Val Leu Val Pro
    2270                2275                2280

Ala Thr Thr Ile Pro Ala Gln Thr Arg Thr Ile Pro Leu Asp Ile
    2285                2290                2295

Pro Ala Ser Pro Gly Ser Thr Met Thr Leu Pro Leu Ile Ser Met
    2300                2305                2310

Arg Phe Glu Gly Glu Asp Trp Ile Leu Gly Ser Thr Ala Ala Ile
    2315                2320                2325

Pro Asn Phe Gly Asp Pro Phe Pro Ala Pro Thr Gln Gly Ile Thr
    2330                2335                2340

Ile His Thr Gly Pro Gly Pro Gly Thr Thr Gly Glu Leu Lys Ile
    2345                2350                2355

Ser Ile Pro Gly Phe Glu Ile Pro Gln Ile Ala Thr Thr Arg Phe
    2360                2365                2370

Leu Leu Asp Val Asn Ile Ser Gly Gly Leu Pro Ala Phe Thr Leu
    2375                2380                2385

Phe Ala Gly Gly Leu Thr Ile Pro Thr Asn Ala Ile Pro Leu Thr
    2390                2395                2400

Ile Asp Ala Ser Gly Ala Leu Asp Pro Ile Thr Ile Phe Pro Gly
    2405                2410                2415

Gly Tyr Thr Ile Asp Pro Leu Pro Leu His Leu Ala Leu Asn Leu
    2420                2425                2430

Thr Val Pro Asp Ser Ser Ile Pro Ile Ile Asp Val Pro Pro Thr
    2435                2440                2445

Pro Gly Phe Gly Asn Thr Thr Ala Thr Pro Ser Ser Gly Phe Phe
    2450                2455                2460

Asn Ser Gly Ala Gly Gly Val Ser Gly Phe Gly Asn Val Gly Ser
    2465                2470                2475

Asn Leu Ser Gly Trp Trp Asn Gln Ala Ala Ser Ala Leu Ala Gly
    2480                2485                2490

Ser Gly Ser Gly Val Leu Asn Val Gly Thr Leu Gly Ser Gly Val
    2495                2500                2505

Leu Asn Val Gly Ser Gly Val Ser Gly Ile Tyr Asn Thr Ser Val
    2510                2515                2520

Leu Pro Leu Gly Thr Pro Ala Val Leu Ser Gly Leu Gly Asn Val
    2525                2530                2535

Gly His Gln Leu Ser Gly Val Ser Ala Ala Gly Thr Ala Leu Asn
    2540                2545                2550

Gln Ile Pro Ile Leu Asn Ile Gly Leu Ala Asp Val Gly Asn Phe
    2555                2560                2565

Asn Val Gly Phe Gly Asn Val Gly Asp Val Asn Leu Gly Ala Ala
    2570                2575                2580

Asn Leu Gly Ala Gln Asn Leu Gly Leu Gly Asn Val Gly Thr Gly
    2585                2590                2595

Asn Leu Gly Phe Ala Asn Val Gly His Gly Asn Ile Gly Phe Gly
    2600                2605                2610

Asn Ser Gly Leu Thr Ala Gly Ala Ala Gly Leu Gly Asn Thr Gly
    2615                2620                2625

Phe Gly Asn Ala Gly Ser Ala Asn Tyr Gly Phe Ala Asn Gln Gly
```

-continued

```
            2630                2635                2640
Val Arg Asn Ile Gly Leu Ala Asn Thr Gly Thr Gly Asn Ile Gly
            2645                2650                2655
Ile Gly Leu Val Gly Asp Asn Leu Thr Gly Ile Gly Gly Leu Asn
            2660                2665                2670
Ser Gly Ala Gly Asn Ile Gly Leu Phe Asn Ser Gly Thr Gly Asn
            2675                2680                2685
Ile Gly Phe Phe Asn Ser Gly Thr Gly Asn Phe Gly Ile Gly Asn
            2690                2695                2700
Ser Gly Ser Phe Asn Thr Gly Ile Gly Asn Ser Gly Thr Gly Ser
            2705                2710                2715
Thr Gly Leu Phe Asn Ala Gly Ser Phe Asn Thr Gly Val Ala Asn
            2720                2725                2730
Ala Gly Ser Tyr Asn Thr Gly Ser Phe Asn Ala Gly Asp Thr Asn
            2735                2740                2745
Thr Gly Gly Phe Asn Pro Gly Thr Ile Asn Thr Gly Trp Phe Asn
            2750                2755                2760
Thr Gly His Thr Asn Thr Gly Ile Ala Asn Ser Gly Asn Val Gly
            2765                2770                2775
Thr Gly Ala Phe Met Ser Gly Asn Phe Ser Asn Gly Leu Leu Trp
            2780                2785                2790
Arg Gly Asp His Glu Gly Leu Phe Ser Leu Phe Tyr Ser Leu Asp
            2795                2800                2805
Val Pro Arg Ile Thr Ile Val Asp Ala His Leu Asp Gly Gly Phe
            2810                2815                2820
Gly Pro Val Val Leu Pro Pro Ile Pro Val Pro Ala Val Asn Ala
            2825                2830                2835
His Leu Thr Gly Asn Val Ala Met Gly Ala Phe Thr Ile Pro Gln
            2840                2845                2850
Ile Asp Ile Pro Ala Leu Thr Pro Asn Ile Thr Gly Ser Ala Ala
            2855                2860                2865
Phe Arg Ile Val Val Gly Ser Val Arg Ile Pro Pro Val Ser Val
            2870                2875                2880
Ile Val Glu Gln Ile Ile Asn Ala Ser Val Gly Ala Glu Met Arg
            2885                2890                2895
Ile Asp Pro Phe Glu Met Trp Thr Gln Gly Thr Asn Gly Leu Gly
            2900                2905                2910
Ile Thr Phe Tyr Ser Phe Gly Ser Ala Asp Gly Ser Pro Tyr Ala
            2915                2920                2925
Thr Gly Pro Leu Val Phe Gly Ala Gly Thr Ser Asp Gly Ser His
            2930                2935                2940
Leu Thr Ile Ser Ala Ser Ser Gly Ala Phe Thr Thr Pro Gln Leu
            2945                2950                2955
Glu Thr Gly Pro Ile Thr Leu Gly Phe Gln Val Pro Gly Ser Val
            2960                2965                2970
Asn Ala Ile Thr Leu Phe Pro Gly Gly Leu Thr Phe Pro Ala Thr
            2975                2980                2985
Ser Leu Leu Asn Leu Asp Val Thr Ala Gly Ala Gly Gly Val Asp
            2990                2995                3000
Ile Pro Ala Ile Thr Trp Pro Glu Ile Ala Ala Ser Ala Asp Gly
            3005                3010                3015
Ser Val Tyr Val Leu Ala Ser Ser Ile Pro Leu Ile Asn Ile Pro
            3020                3025                3030
```

```
Pro Thr Pro Gly Ile Gly Asn Ser Thr Ile Thr Pro Ser Ser Gly
3035                3040                3045

Phe Phe Asn Ala Gly Ala Gly Gly Ser Gly Phe Gly Asn Phe
3050                3055                3060

Gly Ala Gly Thr Ser Gly Trp Trp Asn Gln Ala His Thr Ala Leu
3065                3070                3075

Ala Gly Ala Gly Ser Gly Phe Ala Asn Val Gly Thr Leu His Ser
3080                3085                3090

Gly Val Leu Asn Leu Gly Ser Gly Val Ser Gly Ile Tyr Asn Thr
3095                3100                3105

Ser Thr Leu Gly Val Gly Thr Pro Ala Leu Val Ser Gly Leu Gly
3110                3115                3120

Asn Val Gly His Gln Leu Ser Gly Leu Leu Ser Gly Gly Ser Ala
3125                3130                3135

Val Asn Pro Val Thr Val Leu Asn Ile Gly Leu Ala Asn Val Gly
3140                3145                3150

Ser His Asn Ala Gly Phe Gly Asn Val Gly Glu Val Asn Leu Gly
3155                3160                3165

Ala Ala Asn Leu Gly Ala His Asn Leu Gly Phe Gly Asn Ile Gly
3170                3175                3180

Ala Gly Asn Leu Gly Phe Gly Asn Ile Gly His Gly Asn Val Gly
3185                3190                3195

Val Gly Asn Ser Gly Leu Thr Ala Gly Val Pro Gly Leu Gly Asn
3200                3205                3210

Val Gly Leu Gly Asn Ala Gly Gly Asn Asn Trp Gly Leu Ala Asn
3215                3220                3225

Val Gly Val Gly Asn Ile Gly Leu Ala Asn Thr Gly Thr Gly Asn
3230                3235                3240

Ile Gly Ile Gly Leu Thr Gly Asp Tyr Gln Thr Gly Ile Gly Gly
3245                3250                3255

Leu Asn Ser Gly Ala Gly Asn Leu Gly Leu Phe Asn Ser Gly Ala
3260                3265                3270

Gly Asn Val Gly Phe Phe Asn Thr Gly Thr Gly Asn Phe Gly Leu
3275                3280                3285

Phe Asn Ser Gly Ser Phe Asn Thr Gly Val Gly Asn Ser Gly Thr
3290                3295                3300

Gly Ser Thr Gly Leu Phe Asn Ala Gly Ser Phe Asn Thr Gly Val
3305                3310                3315

Ala Asn Ala Gly Ser Tyr Asn Thr Gly Ser Phe Asn Val Gly Asp
3320                3325                3330

Thr Asn Thr Gly Gly Phe Asn Pro Gly Ser Ile Asn Thr Gly Trp
3335                3340                3345

Leu Asn Ala Gly Asn Ala Asn Thr Gly Val Ala Asn Ala Gly Asn
3350                3355                3360

Val Asn Thr Gly Ala Phe Val Thr Gly Asn Phe Ser Asn Gly Ile
3365                3370                3375

Leu Trp Arg Gly Asp Tyr Gln Gly Leu Ala Gly Phe Ala Val Gly
3380                3385                3390

Tyr Thr Leu Pro Leu Phe Pro Ala Val Gly Ala Asp Val Ser Gly
3395                3400                3405

Gly Ile Gly Pro Ile Thr Val Leu Pro Pro Ile His Ile Pro Pro
3410                3415                3420

Ile Pro Val Gly Phe Ala Ala Val Gly Gly Ile Gly Pro Ile Ala
3425                3430                3435
```

Ile Pro Asp Ile Ser Val Pro Ser Ile His Leu Gly Leu Asp Pro
     3440                3445                3450

Ala Val His Val Gly Ser Ile Thr Val Asn Pro Ile Thr Val Arg
     3455                3460                3465

Thr Pro Pro Val Leu Val Ser Tyr Ser Gln Gly Ala Val Thr Ser
     3470                3475                3480

Thr Ser Gly Pro Thr Ser Glu Ile Trp Val Lys Pro Ser Phe Phe
     3485                3490                3495

Pro Gly Ile Arg Ile Ala Pro Ser Ser Gly Gly Ala Thr Ser
     3500                3505                3510

Thr Gln Gly Ala Tyr Phe Val Gly Pro Ile Ser Ile Pro Ser Gly
     3515                3520                3525

Thr Val Thr Phe Pro Gly Phe Thr Ile Pro Leu Asp Pro Ile Asp
     3530                3535                3540

Ile Gly Leu Pro Val Ser Leu Thr Ile Pro Gly Phe Thr Ile Pro
     3545                3550                3555

Gly Gly Thr Leu Ile Pro Thr Leu Pro Leu Gly Leu Ala Leu Ser
     3560                3565                3570

Asn Gly Ile Pro Pro Val Asp Ile Pro Ala Ile Val Leu Asp Arg
     3575                3580                3585

Ile Leu Leu Asp Leu His Ala Asp Thr Thr Ile Gly Pro Ile Asn
     3590                3595                3600

Val Pro Ile Ala Gly Phe Gly Gly Ala Pro Gly Phe Gly Asn Ser
     3605                3610                3615

Thr Thr Leu Pro Ser Ser Gly Phe Phe Asn Thr Gly Ala Gly Gly
     3620                3625                3630

Gly Ser Gly Phe Ser Asn Thr Gly Ala Gly Met Ser Gly Leu Leu
     3635                3640                3645

Asn Ala Met Ser Asp Pro Leu Leu Gly Ser Ala Ser Gly Phe Ala
     3650                3655                3660

Asn Phe Gly Thr Gln Leu Ser Gly Ile Leu Asn Arg Gly Ala Gly
     3665                3670                3675

Ile Ser Gly Val Tyr Asn Thr Gly Ala Leu Gly Val Val Thr Ala
     3680                3685                3690

Ala Val Val Ser Gly Phe Gly Asn Val Gly Gln Gln Leu Ser Gly
     3695                3700                3705

Leu Leu Phe Thr Gly Val Gly Pro
     3710                3715

<210> SEQ ID NO 13
<211> LENGTH: 11
<212> TYPE: PRT
<213> ORGANISM: Mycobacterium tuberculosis

<400> SEQUENCE: 13

Gln Thr Val Glu Asp Glu Ala Arg Arg Met Trp
1               5                   10

<210> SEQ ID NO 14
<211> LENGTH: 9
<212> TYPE: PRT
<213> ORGANISM: Mycobacterium tuberculosis

<400> SEQUENCE: 14

Val Ser Ala Ala Ile Ala Gly Leu Phe
1               5

<210> SEQ ID NO 15
<211> LENGTH: 297
<212> TYPE: DNA
<213> ORGANISM: Mycobacterium tuberculosis

<400> SEQUENCE: 15
atggcctcgc gttttatgac ggatccgcac gcgatgcggg acatggcggg ccgttttgag     60
gtgcacgccc agacggtgga ggacgaggct cgccggatgt gggcgtccgc gcaaaacatc    120
tcgggcgcgg gctggagtgg catggccgag gcgacctcgc tagacaccat gacccagatg    180
aatcaggcgt ttcgcaacat cgtgaacatg ctgcacgggg tgcgtgacgg gctggttcgc    240
gacgccaaca actacgaaca gcaagagcag gcctcccagc agatcctcag cagctga      297

<210> SEQ ID NO 16
<211> LENGTH: 297
<212> TYPE: DNA
<213> ORGANISM: Mycobacterium tuberculosis

<400> SEQUENCE: 16
atggcctcac gttttatgac ggatccgcac gcgatgcggg acatggcggg ccgttttgag     60
gtgcacgccc agacggtgga ggacgaggct cgccggatgt gggcgtccgc gcaaaacatt    120
tccggtgcgg gctggagtgg catggccgag gcgacctcgc tagacaccat ggcccagatg    180
aatcaggcgt ttcgcaacat cgtgaacatg ctgcacgggg tgcgtgacgg gctggttcgc    240
gacgccaaca actacgagca gcaagagcag gcctcccagc agatcctcag cagctaa      297

<210> SEQ ID NO 17
<211> LENGTH: 297
<212> TYPE: DNA
<213> ORGANISM: Mycobacterium tuberculosis

<400> SEQUENCE: 17
atggcctcac gttttatgac ggatccgcat gcgatgcggg acatggcggg ccgttttgag     60
gtgcacgccc agacggtgga ggacgaggct cgccggatgt gggcgtccgc gcaaaacatt    120
tccggtgcgg gctggagtgg catggccgag gcgacctcgc tagacaccat gacctagatg    180
aatcaggcgt ttcgcaacat cgtgaacatg ctgcacgggg tgcgtgacgg gctggttcgc    240
gacgccaaca actacgaaca gcaagagcag gcctcccagc agatcctgag cagctag      297

<210> SEQ ID NO 18
<211> LENGTH: 297
<212> TYPE: DNA
<213> ORGANISM: Mycobacterium tuberculosis

<400> SEQUENCE: 18
atggcaacac gttttatgac ggatccgcac gcgatgcggg acatggcggg ccgttttgag     60
gtgcacgccc agacggtgga ggacgaggct cgccggatgt gggcgtccgc gcaaaacatc    120
tcgggcgcgg gctggagtgg catggccgag gcgacctcgc tagacaccat ggcccagatg    180
aatcaggcgt ttcgcaacat cgtgaacatg ctgcacgggg tgcgtgacgg gctggttcgc    240
gacgccaaca actacgagca gcaagagcag gcctcccagc agatcctcag cagctaa      297

<210> SEQ ID NO 19
<211> LENGTH: 297
<212> TYPE: DNA
<213> ORGANISM: Mycobacterium tuberculosis

<400> SEQUENCE: 19

```
atgacctcgc gttttatgac ggatccgcac gcgatgcggg acatggcggg ccgttttgag     60
gtgcacgccc agacggtgga ggacgaggct cgccggatgt gggcgtccgc gcaaaacatt    120
tccggcgcgg gctggagtgg catggccgag gcgacctcgc tagacaccat gacccagatg    180
aatcaggcgt ttcgcaacat cgtgaacatg ctgcacgggg tgcgtgacgg gctggttcgc    240
gacgccaaca actacgaaca gcaagagcag gcctcccagc agatcctcag cagctga       297
```

```
<210> SEQ ID NO 20
<211> LENGTH: 435
<212> TYPE: DNA
<213> ORGANISM: Mycobacterium tuberculosis

<400> SEQUENCE: 20
atgtcataca tgattgccac accagcggcg ttgacggcgg cggcaacgga tatcgacggg     60
attggctcgg cggttagcgt tgcgaacgcc gcggcggtcg ccgcgacaac cggagtgctg    120
gccgccggtg gcgatgaagt gttggcggcc atcgctaggc tgttcaacgc aaacgccgag    180
gaatatcacg ccctcagcgc gcaggtggcg gcgtttcaaa ccctgtttgt gcgcaccttg    240 actgggggg t gcggagtctt tcgccggcgc cgaggccgcc aatgcgtcac agctgcagag   300
catcgcgcgg caggtgcggg gcgccgtcaa cgccgtcgcc ggtcaggtga cgggcaatgg    360
cggctccggc aacagcggca cttcggctgc ggcggccaac ccgaattccg acaacacagc    420
gagcatcgcc gatag                                                     435
```

```
<210> SEQ ID NO 21
<211> LENGTH: 2085
<212> TYPE: DNA
<213> ORGANISM: Mycobacterium tuberculosis

<400> SEQUENCE: 21
gtgtcgttgg tgatcgcgac gccgcagctg ctggcaactg cggctttgga tttagcgagt     60
attggttcgc aggtgagcgc ggctaatgcg gccgcggcga tgccgacgac ggaagtggtg    120
gctgcggctg ccgatgaagt gtcggcggcg attgcggggt tgttcggggc ccatgctcgg    180
cagtatcagg cgctcagcgt acaggtggca gcgtttcacg agcagtttgt gcaggcgttg    240
actgcggccg cgggtcggta tgccagcact gaggccgctg ttgagcggag tctgctgggt    300
gcggtgaatg cgcccaccga ggcgcttttg gggcgcccgt tgatcggaaa cggcgccgac    360
gggacggcac ccgggcagcc tggcgcggcc ggcgggttgc tgtttggcaa cggtggcaac    420
ggcgcggctg gcgggttcgg tcaaaccggc ggcagcggag gcgcggccgg gttgatcggc    480
aacggcggca acggcggggc cggtggtacc ggcgcggccg gcggtgccgg tgggaacggg    540
gggtggttgt ggggcaacgg cggcaacggc ggtgtcggcg gcaccagcgt ggccgcaggc    600
atcgggggtg cgggcggtaa cggcggcaac gccgggctgt tcggccatgg cggcgccggt    660
ggtaccggcg gcgccggcct cgccggggca aacggggtca atcccacgcc cggccccgcg    720
gccagcaccg gggacagccc ggcagatgtg tccggcatcg gtgatcaaac cggcggcgac    780
ggcggcacgg gcggccatgg cactgccggc acgccgaccg gtggcaccgg cggcgacggt    840
gccaccgcga cggcaggctc gggcaaggcc accggcggtg ccggtggtga cggcggtacc    900
gccgctgccg gtggcggcgg cggcaacggc ggcgacggcg gagtcgcgca gggcgacatt    960
gcgagcgcct ttggcggtga tggtggcaac gggtccgacg gtgtagccgc cggcagtggg   1020
ggtggtagcg gcggcgccgg aggcggcgct ttcgtacaca tcgccactgc cacctctacc   1080
ggtggtagcg gcggtttcgg tggtaacggg gctgccagtg ccgcctccgg cgccgacggt   1140
```

| | |
|---|---|
| ggcgcagggg gagctggcgg caatggtggc gccggcgggt tgctattcgg tgatggcggc | 1200 |
| aacggtggcg ccggtggcgc gggtggtatc ggtggtgacg gcgccacggg ggggcccggg | 1260 |
| ggaagcggcg gcaacgctgg catcgcgagg tttgacagcc cagaccccga ggcagaaccc | 1320 |
| gatgtggtcg gcggcaaggg tggtgatggc ggcaagggcg gcagcggcct ggcgtcggc | 1380 |
| ggcgccggcg gaccggcgg cgcgggcggc aacggcggcg ccggcgggtt gttgttcggc | 1440 |
| aacggcggca acgcggcaa cgccggggcc ggcgggatg gcggcgccgg cgttgccggt | 1500 |
| ggggttggcg gtaacggcgg cggtggtggc accgcgacgt ttcacgaaga cccggtcgct | 1560 |
| ggtgtctggg cggtcggtgg cgtaggtggt gatggtggct ccggcggcag ctcgcttggt | 1620 |
| gtcggcgggg tgggcggagc cggtggcgtg ggtggcaagg gtggcgccag cggcatgttg | 1680 |
| atcggcaacg gcggcaacgg tggcagcggc ggagtcggtg gggccggtgg agtcggcggg | 1740 |
| gctggcggtg acggcggcaa cggcggctcc ggtggcaacg ccagtacttt tggcgatgag | 1800 |
| aactccatcg gcggggccgg cgggacgggc ggcaacgggg gcaacggcgc aaacggcggt | 1860 |
| aacggtggcg ctggcggtat tgccggcggt gcgggtgggt ccggagggtt cctcagcggt | 1920 |
| gccgcaggag tcagcggcgc tgacggtatc ggtggcgcgg gcggcgcagg cggtgccggt | 1980 |
| ggcgcgggcg gtagcggcgg tgaggcaggc gcgggggcc tcaccaacgg ccccgggtcc | 2040 |
| cctggcgttt ccggcaccga aggcatggcc ggcgcgcccg gctag | 2085 |

```
<210> SEQ ID NO 22
<211> LENGTH: 978
<212> TYPE: DNA
<213> ORGANISM: Mycobacterium tuberculosis

<400> SEQUENCE: 22
```

| | |
|---|---|
| atgcatcagg tggaccccaa cttgacacgt cgcaagggac gattggcggc actggctatc | 60 |
| gcggcgatgg ccagcgccag cctggtgacc gttgcggtgc ccgcgaccgc caacgccgat | 120 |
| ccggagccag cgccccggt acccacaacg gccgcctcgc cgccgtcgac cgctgcagcg | 180 |
| ccacccgcac cggcgacacc tgttgccccc ccaccaccgg ccgccgccaa cacgccgaat | 240 |
| gcccagccgg gcgatcccaa cgcagcacct ccgccggccg acccgaacgc accgccgcca | 300 |
| cctgtcattg ccccaaacgc accccaacct gtccggatcg acaacccggt tggaggattc | 360 |
| agcttcgcgc tgcctgctgg ctgggtggag tctgacgccg cccacttcga ctacggttca | 420 |
| gcactcctca gcaaaaccac cggggacccg ccatttcccg gacagccgcc gccggtggcc | 480 |
| aatgacaccc gtatcgtgct cggccggcta gaccaaaagc tttacgccag cgccgaagcc | 540 |
| accgactcca aggccgcggc ccggttgggc tcggacatgg gtgagttcta tatgccctac | 600 |
| ccgggcaccc ggatcaacca ggaaaccgtc tcgctcgacg ccaacggggt gtctggaagc | 660 |
| gcgtcgtatt acgaagtcaa gttcagcgat ccgagtaagc cgaacggcca gatctggacg | 720 |
| ggcgtaatcg gctcgcccgc ggcgaacgca ccggacgccg gccccctca gcgctggttt | 780 |
| gtggtatggc tcgggaccgc caacaacccg gtggacaagg gcgcggccaa ggcgctggcc | 840 |
| gaatcgatcc ggcctttggt cgccccgccg ccggcgccgg caccggctcc tgcagagccc | 900 |
| gctccggcgc cggcgccggc cggggaagtc gctcctaccc cgacgacacc gacaccgcag | 960 |
| cggaccttac cggcctga | 978 |

```
<210> SEQ ID NO 23
<211> LENGTH: 1749
<212> TYPE: DNA
<213> ORGANISM: Mycobacterium tuberculosis
```

```
<400> SEQUENCE: 23
atgctcctgg ccctgctgcg ccagcacatc cgaccgtacc gccggctggt cgcgatgctg      60
atgatgctgc agctggtcag caccctggct tcgctatacc tcccgacggt caacgccgca     120
atcgtcgacg acggcgtcgc caagggcgac accgccacca tcgtacggct gggtgcggtg     180
atgcttgggg tgaccggatt gcaggtgctg tgcgcgatcg gggcggtcta tctgggctcc     240
cggaccgggg cgggtttcgg ccgtgacctg cgctcggcaa tgttcgaaca catcatcacc     300
ttctcggaac gcgagaccgc ccgattcggc gctccgacgt tgttgacccg cagcaccaac     360
gacgtccggc agatcctgtt cctggtccag atgaccgcca ccgtgctggt caccgcaccg     420
atcatgtgcg tcggcggaat catcatggcc atccaccagg aggccgcgct gacatggctg     480
ctgctggtca gcgttccgat tctggccgta gcaaactact ggatcatctc ccacatgctg     540
ccgctcttcc gccgcatgca gagcctgatc gacggcatca accgggtgat gcgcgatcag     600
ctgtccgggg tgcgagtggt ccgcgccttc acccgcgaag gctatgaacg cgacaagttc     660
gcgcaggcca atacggcgct gtcgaatgcc gcactgagcg ccggcaactg gcaagcactg     720
atgctgccgg tgaccacgct gaccatcaac gcatccagcg tcgcactgat ctggttcggt     780
gggctacgca tcgacagcgg ccagatgcag gtcggctccc tgatcgcctt cctgtcctac     840
ttcgcccaga tcctgatggc ggtgttgatg gcgaccatga cgctggccgt gctgccacga     900
gcgtcggtct gcgccgaacg catcaccgag gtgctttcca cgcccgccgc actcggtaac     960
cccgacaatc ccaagttccc gacggacggg gtcacgggcg tagtgcgctt ggctggcgca    1020 accttttacct atcctggcgc cgactgcccg gtgctgcagg acatttcgtt gactgcgcgg    1080
cccggtacca ccaccgcgat cgtcggcagt accggttcgg gcaagtcgac actggtgtcg    1140
ttgatctgcc ggctctacga cgtcaccgct ggcgcggtct tggttgacgg tatcgacgtc    1200
cgcgagtacc acaccgagcg gctctggtca gcgatcgggc tggtgcccca gcgcagctac    1260
ctcttctccg gaaccgtcgc ggacaacctg cgctacggcg ggggcccaga ccaggtagtc    1320
accgagcagg agatgtggga ggcgctgcgg gtcgccgcgg ccgacggctt tgtacaaaca    1380
gacgggctgc agacgcgtgt cgcccaaggt ggtgtcaact tctccggcgg gcagcgccaa    1440
cggctggcga tagcccgagc ggtcatccga cgtccggcca tctatgtgtt cgacgacgcg    1500
ttctccgcac ttgacgtgca caccgacgcc aaagtccacg catcgctgcg acaggtatct    1560
ggtgatgcaa ccatcattgt tgttacacaa cggatttcga atgccgctca ggccgaccag    1620
gtcatcgttg tcgataacgg taagatcgtc ggcacgggca cccacgaaac gctgctggcc    1680 gattgccccca cctatgccga attcgccgcc tcacaatcgc tgagcgccac ggtcggggt    1740 gtagggtga                                                            1749

<210> SEQ ID NO 24
<211> LENGTH: 1407
<212> TYPE: DNA
<213> ORGANISM: Mycobacterium tuberculosis

<400> SEQUENCE: 24
atgtcctacg tcatcgcggc cccggagatg ttggcaacga cggccgcgga cgtggacggg      60
atcggttcgg cgatacgagc ggccagcgcg tccgctgcgg tccaacgac cggactgctg     120 gccgcggccg ccgatgaggt gtcgtcggcc gctgcagcgc tgttcagcga atacgcgcgc     180
gaatgtcaag aggtcctaaa gcaggctgcg gcgttccatg gcgagttcac ccgggcgctg     240
gctgccgccg gggccgccta tgcccaggct gaagccagca acaccgctgc tatgtcgggc     300
```

| | | |
|---|---|---|
| accgccgggt ccagcggcgc cctcggttct gtcgggatgc tgtcaggcaa cccgctaacc | 360 | |
| gcgttgatga tgggcggcac cggggaaccg atccttagtg accgcgtctt ggcgatcatt | 420 | |
| gacagcgcat acattcggcc catttccggg cccaacaacc cggtcgccca gtacacgccc | 480 | |
| gagcagtggt ggccgtttat cgggaacctg tcactggacc aatccatcgc caggggtgtc | 540 | |
| acgctgctga caacggcat caacgcggaa ctacaaaatg gcatgacgt cgtcgttttc | 600 | |
| ggctactcgc aaagcgccgc ggtagcgacc aatgaaatac gcgctcttat ggcgttacca | 660 | |
| ccgggccaag ccccagatcc aagccggctg gctttcacgt tgatcggtaa tatcaataac | 720 | |
| cccaacggcg cgtcctcga gcgttacgtg ggcctttacc tcccgttctt ggatatgtcg | 780 | |
| ttcaacggtg cgactccacc ggattcccc taccagacct acatgtacac cggccaatac | 840 | |
| gacggctacg cccacaaccc gcagtacccg ctcaatatct tgtcggacct caacgccttc | 900 | |
| atgggcatca gatgggtgca caacgcgtac cccttcaccg cggccgaggt tgccaatgcc | 960 | |
| gtgccgttgc ccacgtctcc gggctacacc ggcaacaccc attactacat gtttctgacc | 1020 | |
| caggacctgc cgctgttgca gccgattcgc gccatcccct tcgtagggac cccaatagcc | 1080 | |
| gagctgattc agcccgacct acgggtgcta gtcgacttgg gctatggcta cggctacgcc | 1140 | |
| gacgtaccca ccccggccag cctgttcgcg ccaatcaacc cgatcgccgt ggcctcggcc | 1200 | |
| ctggcgaccg ggaccgtgca aggccccaa gccgccctag taagcatcgg attgttaccg | 1260 | |
| cagtccgcgc tacccaatac gtatccgtat cttccgtcgg cgaatccggg cctgatgttc | 1320 | |
| aacttcggtc aatccagtgt gacggagttg tcggtgctca gtggcgccct cgggtccgta | 1380 | |
| gcgagattga ttccaccgat cgcgtga | 1407 | |

<210> SEQ ID NO 25
<211> LENGTH: 11151
<212> TYPE: DNA
<213> ORGANISM: Mycobacterium tuberculosis

<400> SEQUENCE: 25

| | |
|---|---|
| atggagtttc cggtgttgcc accggaaatc aactccgtgc tgatgtattc gggtgcgggg | 60 |
| tcgagcccgt tgctggcggc ggccgcggcg tgggatgggc tggctgagga gttggggtcg | 120 |
| gcggcggtgt cgtttgggca ggtgacgtcg ggcctgacgg cggggtgtg cagggtgcg | 180 |
| gcggcggcg cgatgcggc cgcggcggcg ccgtatgcgg ggtggttggg ttcggtggcg | 240 |
| gccgcggccg aggcggtggc cgggcaggcg cgggtggtgg tggggtctt tgaggcggcg | 300 |
| ttggcggcga cggtggatcc ggcgctggtg cggccaacc gggcgcggct ggtggcgttg | 360 |
| gcggtgtcga atctgttggg gcagaacacg ccggcgatcg cggccgccga ggccgagtac | 420 |
| gagctgatgt gggccgccga tgtggcgcg atggccggct accattccgg cgcgtcggct | 480 |
| gctgccgcgg cgttgccggc gttcagccca ccggcgcagg cgctggggg aggtgtcggc | 540 |
| gcgttccctta ccgccctgtt cgccagccct gcgaaggcgc tgagcctgaa tgcgggtttg | 600 |
| ggcaatgtcg gcaattacaa cgtcgggttg ggcaatgtcg gggtgttcaa cctgggcgcg | 660 |
| ggcaatgtgg gtgggcagaa tctgggtttc gggaatgccg gtggcaccaa gtcgggttc | 720 |
| ggcaacctcg gtaacgggaa tgtcgggttc ggcaactccg gtctggggc gggcctggcc | 780 |
| ggcttgggca atatcgggtt gggcaatgcg gcagcagca actatggttt cgcaaacctg | 840 |
| ggtgtgggca acatcggttt cggcaacacc ggcaccaaca acgtcggcgt cgggctcacc | 900 |
| ggcaaccacc tgacgggtat cggggcctg aattcgggca ccgggaatat cgggttgttc | 960 |
| aactccggca ccgggaatgt ggggttcttc aattcgggga ccgggaactt cggggtgttc | 1020 |

```
aactcgggta attacaacac cggtgtcggt aatgcgggga cggccagcac ggggttgttc    1080
aatgccggca atttcaacac cggcgtggtg aacgtgggca gttacaacac cggcagtttc    1140
aacgccggcg acaccaacac cggtggcttc aaccccggcg tgtgaacac cggctggctg     1200 aacaccggca acaccaacac cggcatcgcc aactcgggca acgtcaacac cggcgcgttc    1260
atctcgggca acttcaacaa cggcgtgctg tgggtgggtg actaccaggg cctgttcggc    1320
gtctccgccg gctcgtcgat ccccgcaatt cccatcggcc tggtgctcaa cggcgacatc    1380
ggcccgatca ccatccagcc catcccgatc ctgcccacca tcccgctcag cattcaccaa    1440
accgtcaact gggcccgct ggtggttccc gacatcgtga tccccgcctt cggcggcggt     1500
atcggcatac ccatcaacat cggcccgctg accatcacac ccatcaccct gtttgcccaa    1560
cagacatttg tcaaccaatt gccctttccc accttcagtt tagggaaaat cacaattcca    1620
caaatccaaa cctttgattc taacggtcag cttgtcagct ttatcggccc tatcgttatc    1680
gacaccacca ttcccggacc caccaatcca cagattgatt taacgatcag atgggatacc    1740
cctccgatca cgctgttccc gaatggcatc agtgctcccg ataatccttt ggggttgctg    1800
gtgagtgtgt cgatcagtaa cccgggcttt accatcccgg gatttagtgt cccgcgcag    1860 ccgttgccgt tgtcgatcga tatcgagggc cagatcgacg ggttcagcac cccgccgatc    1920
acgatcgatc gcatccccct gaccgtgggg ggcggggtca cgatcggccc catcacgatc    1980
cagggccttc atatcccggc ggcgccggga gtggggaaca ccaccacggc cccgtcgtcg    2040
ggattcttca actccggtgc gggtggggtg tcgggtttcg gcaacgtcgg cgcgggcagc    2100
tcgggctggt ggaaccaggc gccgagcgcg ctgttggggg ccggttcggg tgttggcaac    2160
gtgggcaccc tgggctcggg tgtgctcaac ctgggctcag ggatctcggg gttctacaac    2220
accagcgtgt tgcctttcgg gacaccggcg gcggtgtcgg gcatcggcaa cctgggccag    2280
cagctgtcgg gggtgtcggc ggcgggaacc acgctgcgct cgatgctcgc cggcaacctc    2340
gggttggcca atgtgggcaa cttcaacacc gggttcggaa atgtcgggga cgtcaacctg    2400
ggtgcggcca acatcggtgg gcacaacctg ggcctgggca atgtcgggga cggcaacctg    2460
gggttgggca acatcggcca tggcaacctg gggtttgcca acttgggcct gaccgccggc    2520
gcggcggggg tgggcaatgt tggttttggc aatgccggca tcaacaacta tggcttggcg    2580
aacatgggtg tgggcaatat tgggtttgcc aacaccggca cgggcaacat cgggatcggg    2640
ctggtcgggg accatcggac cgggatcggg ggcttgaact ccggcatcgg caatatcggg    2700
ttgttcaact ccggcaccgg caacgtcggg ttcttcaatt ccgggaccgg caacttcggc    2760
atcgggaact ccggccgctt caacaccggg atcggtaata gcggaacggc cagcaccggg    2820
ctcttcaatg ccggcagctt cagcaccggc atcgccaaca ctggtgacta caacacgggc    2880
agcttcaacg ccggcgacac caacaccggt ggcttcaacc cggcggcat caacaccggc     2940 tggttcaaca ccgggcatgc caacaccggg ttggccaacg cggcacctt cggcaccggc     3000 gccttcatga cgggcgacta cagcaacggc ctgttgtggc ggggcggcta cgagggcctg    3060
gtcggcgtcc gcgtcgggcc cacgatctcc caattcccgg tcaccgtgca cgcgatcggc    3120
ggggtgggcc cgctgcatgt ggcgcccgtc ccggtacccg ccgtgcacgt cgagatcacc    3180
gacgccaccg tcggcctggg tccgttcacc gtcccaccga tcagcattcc ctcacttccc    3240
atcgccagca tcaccggaag cgtggacctg gccgcaaaca ccatctcgcc gattcgcgct    3300
cttgacccgc tcgccggttc gatagggctt tttctcgagc cgttccgcct cagtgaccca    3360
tttatcacca ttgatgcgtt ccaagttgtt gccggtgtct tgttcctaga gaacatcatt    3420
```

```
gtgcccggcc tcacggttag cggtcagata ttggtcaccc cgacaccaat tcccctaacc    3480
ctcaacttgg acaccacccc gtggacgctt ttcccgaatg gtttcaccat tcccgcgcaa    3540 accccgtga cggtgggtat ggaggtcgcc aacgacgggt tcaccttctt cccgggtggg    3600
ctgacctttc cgcgggcctc cgccgggtc accggactgt ccgtgggct ggacgcgttc    3660 acgctgttgc ccgacgggtt caccctcgac accgtgccgg cgaccttcga cggcaccatc    3720
ctcatcggcg atatcccgat cccgatcatc gatgtgccgg cggtgccggg gttcggcaac    3780
accaccacgg ccccatcgtc ggggttcttc aacaccggcg gcggcggtgg atcggggttc    3840
gccaacgtcg gcgcgggcac gtcggggctgg tggaaccagg ggcacgacgt gttagcaggg    3900
gcgggctcgg gagttgccaa tgccggcacg ctgagctcgg gcgtgctgaa cgtcggctcg    3960
gggatctccg ggtggtacaa caccagcacc ctggagcgg gcaccccggc ggtggtctcg    4020
ggcatcggca acctcggcca gcagctgtcg gggttcttgg caaatgggac cgtgctcaac    4080
cggagcccca ttgtcaatat cgggtgggcc gatgtgggcg cgttcaacac cgggttgggc    4140
aatgtggggg acctcaactg gggtgcggcc aacatcggcg cgcagaacct gggcctgggc    4200
aatctcggca gcgggaacgt cgggttcggc aacatcggtg ccggcaacgt cgggttcgcc    4260
aactcgggtc cggcggtggg cctggccggc ctgggcaacg tggggttgag caatgccggc    4320
agcaacaact gggggctggc caacctgggt gtgggcaaca tcgggttggc caacaccggc    4380
acgggcaaca tcgggatcgg gctggtcggc gactaccaga ccggcatcgg cggcctcaac    4440
tcgggtagtg gcaatatcgg attgttcaat tccggcaccg gcaatgtcgg gttcttcaac    4500
accggcaccg gcaacttcgg actgttcaac tccgtagtt tcaacaccgg catcggtaat    4560 agcgaaccg gcagtactgg gctcttcaat gccggcaatt tcaacaccgg catcgccaac    4620
cccgggtcgt acaacacggg cagcttcaat gtcggtgata ccaacaccgg tggtttcaac    4680
ccgggcgaca tcaacaccgg ctggttcaac accggcatta tgaatacggg cacccgcaac    4740
accggcgccc tcatgtcggg gaccgacagc aacggcatgc tgtggcgcgg cgaccacgag    4800
ggcctgttcg gcctgtccta tggcatcacg atcccgcaat tcccgatccg catcaccacg    4860
actggcggta tcgcccccat cgtcatcccg gacaccacga tccttccgcc gctgcacctg    4920
cagatcaccg gcgacgcgga ctacagcttc accgtgcccg acatccccat ccccgccatc    4980
cacatcggca tcaatggcgt cgtcaccgtc ggcttcaccg ccccggaagc caccctgctg    5040
tccgccctga agaataacgg tagcttcatc agcttcggcc ccatcacgct ctcgaatatc    5100
gatattccgc ccatggattt cacgttaggc ctgcccgttc ttggtcctat cacgggccaa    5160
ctcggaccaa ttcatcttga gccaatcgtg gtggccggga tcggtgtgcc cctggagatc    5220
gagcccatcc ccctgatgc gatttcgttg agtgagtcga ttcctatccg catacctgtt    5280
gatattccgg cctcggtcat cgatgggatt tcaatgtcgg aagtggtgcc gatcgatgcg    5340
tccgtggaca tccggcggt cacgatcaca ggcaccacca tttccgcgat cccgctgggc    5400
ttcgacattc gcaccagtgc cggacccctc aacatcccga tcatcgacat cccggcggcg    5460
ccgggcttcg ggaactcgac ccagatgccg tcgtcgggt tcttcaacac cggtgccggc    5520
ggcggatcgg gcatcggcaa cttgggtgcg gcgtgtcgg gcctgctcaa ccaggccggc    5580
gcggggtcac tggtggggac actctcgggg ctgggcaatg ccggcaccct ggcctcgggt    5640
gtgctgaact ccggcaccgc catctccggg ctgttcaacg tgagcacgct ggacgccacc    5700 accccgcgg tgatctcggg gttcagcaac ctcggcgacc atatgtcggg ggtgtccatc    5760
gatggcctga tcgcgatcct caccttccca cctgccgagt ccgtgttcga tcagatcatc    5820
```

```
gacgcggcca tcgccgagct gcagcacctc gacatcggca acgctttggc cttgggcaat    5880
gtcggcgggg tgaacctcgg tttggctaac gtcggtgagt tcaacctggg tgcgggcaac    5940
gtcggcaaca tcaacgtcgg cgccggcaac ctcggcggca gcaacttggg gttgggcaac    6000
gtcgggaccg gcaacctcgg gttcggcaac atcggtgccg gcaatttcgg attcggcaac    6060
gcgggcctga ccgcgggcgc gggggggcctg ggcaatgtgg ggttgggtaa cgccggcagc    6120
ggcagctggg ggttggccaa cgtgggtgtg ggcaatatcg ggttggccaa caccggcacc    6180
ggcaacatcg ggatcgggct gaccggggac tatcggaccg ggatcggcgg cctgaactcg    6240
ggcaccggga acctcgggtt gttcaactcg ggcaccggca acatcgggtt cttcaacacc    6300
gggaccggga acttcgggct gttcaactcg ggcagttaca gcaccggtgt ggggaatgcg    6360
ggcacggcca gcaccgggtt gttcaacgcg ggaacttca acaccggtct ggccaatgcc    6420
ggctcctaca acaccggcag cctcaacgtg ggcagcttca acaccggcgg cgtcaacccg    6480
ggcaccgtca acaccggctg gttcaacacc ggccacacca acaccggcct gttcaacacc    6540
ggcaacgtca acaccggcgc gttcaactcc ggcagcttca acaacggggc gctgtggacc    6600
ggtgactacc acgggctggt cggcttctcc ttcagcatcg acatcgccgg cagcaccctg    6660
ctggacctca acgaaaccct caacctgggc cccatccaca tcgagcagat cgacatcccc    6720
ggcatgtcgc tgttcgacgt ccacgaaatc gtcgagatcg gacccttcac catcccgcag    6780
gtcgatgttc ccgcgatacc gctagagatc cacgaatcga tccacatgga tcccatcgtc    6840
ctggtgcccg ccaccacaat tcccgcacag acgagaacca ttccgctgga catccccgcc    6900
tcacccgggt caaccatgac gcttccgctc atcagcatgc gcttcgaagg cgaggactgg    6960
atcctcgggt cgaccgcggc gattcccaat ttcggagacc ccttcccggc gcccacccag    7020
ggcatcacca ttcacaccgg ccctggcccc ggaacgaccg gcgagctcaa gatatctatt    7080
ccgggtttcg agattccgca aatcgctacc acgagattcc tgttggacgt gaacatcagc    7140
ggtggtctgc cggccttcac cttgttcgcg ggtggcctga cgatccccac gaacgccatc    7200
ccgttaacga tcgatgcgtc cggcgcgctg gatccgatca cgattttccc gggtgggtac    7260
acgatcgacc cgctgccgct gcacctggcg ctgaatctca ccgtgcccga cagcagcatc    7320
ccgatcatcg atgtcccgcc gacgccaggg ttcggcaaca ccacggcgac cccgtcgtcg    7380
gggttcttca actccggcgc cggtggggtg tcggggttcg gaaacgtcgg gtcgaacctg    7440
tcgggctggt ggaaccaggc ggcgagcgcg ctggcggggt cgggatcggg ggtgttgaat    7500
gtcggcacgc tgggctcggg tgtgctcaac gtcggctcgg gtgtctcggg gatctacaac    7560
accagcgtgt tgccgctcgg gacgccggcg gtgctgtcgg gcctcggcaa cgtcggccat    7620
cagctgtcgg gcgtgtctgc ggccgggacc gcgttgaacc agatccccat cctcaacatc    7680
gggttggcgg atgtgggcaa cttcaacgtc gggttcggca acgtcgggga cgttaacctg    7740
ggcgcggcca acctcggtgc gcaaaacctg ggctgggca acgtcggcac cggcaacctc    7800
ggcttcgcca acgtcggcca cggcaatatc ggtttcggca attcgggtct gaccgccggc    7860
gcggccggcc tggcaacac ggggttcggc aatgccggca gcgccaacta tggtttcgcc    7920
aaccagggcg tgcgcaacat cgggttggcc aacaccggca ccgcaacat cgggatcggg    7980 ctggtggggg acaacctcac cggcatcggg ggcctgaact ccggtgccgg caatatcggc    8040
ttgttcaact ccggcaccgg caacatcggg ttcttcaact ccgggaccgg caacttcggc    8100
atcggtaact cgggcagctt caacaccggc atcggcaata gcggaacggg cagcactggg    8160
ctcttcaatg ccggcagctt caacaccggc gtggccaacg ccggcagcta caacaccggc    8220
```

```
agcttcaatg ccggcgacac caacaccggg gggttcaacc cgggcaccat caacaccggc    8280
tggttcaaca ccggccacac caataccggc atcgccaact cgggcaacgt cggcaccggc    8340
gcgttcatgt cgggcaacTT cagcaacggc ctgttgtggc ggggtgatca cgagggcctg    8400
ttcagcctgt tctacagcct cgacgtgccc cggatcacca tcgtgacgc ccacctcgac     8460 ggcggcttcg gacccgtggt cctcccgccc atcccggtgc cggccgttaa tgcgcacctg    8520 accgaaacg tcgcgatggg cgcattcacc attccgcaga tcgacatccc cgcactcacc     8580
ccaaacatca ccggaagcgc cgccttccgc atcgttgtgg ggtccgtgcg cattccgccg    8640
gtgagtgtca ttgtggagca aataatcaac gcctcggttg gggcggagat gaggatagat    8700
cccttcgaaa tgtggactca aggcactaat ggccttggta taaccttcta ttcattcgga    8760
tcggccgacg gttcgcccta cgccaccggc ccactcgttt cggcgccgg cacgagcgac     8820 ggaagccatc tcaccatttc gcgtccagc ggggcgttta ccactccgca gctcgaaact     8880
ggcccgatca cgttgggctt ccaggtgccc ggcagcgtca acgcgatcac cctcttcccc    8940
ggtggtttga cgttcccggc gacctcgctg ctgaacctgg acgtgaccgc cggcgccggc    9000
ggcgtggaca tcccggccat cacctggccc gagatcgcgg cgagcgccga cggctcggtg    9060
tatgtcctcg ccagcagcat cccgctgatc aacatcccgc ccaccccggg cattgggaac    9120
agcaccatca ccccgtcgtc gggcttcttc aacgccggcg cgggcggggg atcgggcttc    9180
ggcaacttcg gcgcgggcac ctcgggctgg tggaaccagg cgcacaccgc gctggcgggg    9240
gcgggctcgg gttttgccaa cgttggcacg ctgcattccg gtgtgctcaa cctgggctcg    9300
ggtgtctcgg ggatctacaa caccagcacg ctgggggtgg ggaccccggc gctggtctca    9360
ggcctgggca acgtcggcca ccaactgtcg gggctgcttt ccggcgggtc cgcggtgaac    9420
ccggtgaccg ttctgaatat cggggttggcc aacgtcggca gccacaacgc cggtttcggc    9480
aatgtcgggg aggtcaacct gggcgcggcc aacctcggcg cgcacaacct gggcttcgga    9540
aatatcggcg ccggcaacct ggggttcggc aatattggcc acggcaatgt cggagtcggc    9600
aactcgggtc tgaccgcggg cgtgccgggc ctgggcaatg tggggttggg caatgccggc    9660
ggcaacaact gggggttggc caacgtgggc gtgggcaata tcgggttggc caacaccggc    9720
accggcaaca ttgggatcgg gctgaccggc gactaccaga ccggcatcgg cggcctaaat    9780
tccggtgccg gcaacctggg gttgttcaac tccggcgccg gcaacgtcgg gttcttcaac    9840
accgggaccg gcaacttcgg gttgttcaac tccggcagct tcaacaccgg cgtcggcaat    9900
agcggaacgg gcagcactgg gctcttcaat gccggcagtt tcaacaccgg tgtgccaac    9960 gccggcagct acaacacggg cagcttcaat gtcggtgaca ccaacaccgg gggcttcaac   10020
ccgggcagca tcaacaccgg ctggctcaac gccggcaacg ccaacaccgg ggtggccaac   10080
gcgggcaatg tcaacaccgg cgccttcgtc accggcaact tcagcaacgg catcctgtgg   10140
cgcggcgact accagggcct ggccggcttc gccgtgggct acaccctccc gctgttcccc   10200
gcggtgggcg ccgacgtcag cggcgggatc ggcccgatta ccgtgctgcc gcccatccac   10260
atcccgccca ttccggtcgg cttcgccgcg gtcggtggca tcggcccgat cgccatcccg   10320
gacatctctg ttccatccat tcacttgggc ctcgaccccg ccgtccatgt cggctccatc   10380
accgtcaacc ccattaccgt caggacccg cccgtgctcg tcagttactc ccaaggagcc    10440
gtcaccagca cgtccggacc aacctcagag atttgggtca agcccagctt cttccccgga   10500
atccggatcg cgccctctag cggcggggggt gcaacgtcca cgcaaggggc atactttgtg   10560
gggcccatct ccatcccctc cggcacggtg accttcccgg gattcaccat ccccctcgac   10620
```

-continued

```
ccgatcgaca tcggcctgcc ggtgtcgctg accatcccgg ggttcaccat cccgggcggc    10680
accctgatcc ccaccctccc gctgggcctc gcgttgtcca atggcatccc gcccgtcgac    10740
atcccggcca tcgttctcga ccggatcttg ctggacctgc acgccgacac cactatcggc    10800
ccgatcaacg tcccgatcgc cgggttcggc ggggcgccgg gtttcgggaa ctcgaccacg    10860
ctgccgtcgt cgggcttctt caacaccgga gctggcggcg ttcgggctt tagcaacacc     10920 ggcgcgggca tgtcgggatt gctcaacgcg atgtcggatc cgctgctcgg gtcggcgtcg    10980
ggcttcgcca acttcggcac ccagctctcc ggcatcctca accgcggcgc cggcatctcg    11040
ggcgtgtaca acaccggcgc gctgggtgtt gtcaccgcgg ccgtcgtctc gggtttcggc    11100
aacgtcggcc agcaactgtc gggcttgctc ttcaccggcg tcgggcccta a             11151
```

<210> SEQ ID NO 26
<211> LENGTH: 10
<212> TYPE: PRT
<213> ORGANISM: Mycobacterium tuberculosis

<400> SEQUENCE: 26

Ala Glu Met Lys Thr Asp Ala Ala Thr Leu
1               5                   10

<210> SEQ ID NO 27
<211> LENGTH: 10
<212> TYPE: PRT
<213> ORGANISM: Mycobacterium tuberculosis

<400> SEQUENCE: 27

Arg Ala Asp Glu Glu Gln Gln Gln Ala Leu
1               5                   10

<210> SEQ ID NO 28
<211> LENGTH: 10
<212> TYPE: PRT
<213> ORGANISM: Mycobacterium tuberculosis

<400> SEQUENCE: 28

Thr Ala Ala Gln Ala Ala Val Val Arg Phe
1               5                   10

<210> SEQ ID NO 29
<211> LENGTH: 8
<212> TYPE: PRT
<213> ORGANISM: Mycobacterium tuberculosis

<400> SEQUENCE: 29

Ala Glu Met Lys Thr Asp Ala Ala
1               5

<210> SEQ ID NO 30
<211> LENGTH: 11
<212> TYPE: PRT
<213> ORGANISM: Mycobacterium tuberculosis

<400> SEQUENCE: 30

Ala Glu Met Lys Thr Asp Ala Ala Thr Leu Ala
1               5                   10

<210> SEQ ID NO 31
<211> LENGTH: 9

```
<212> TYPE: PRT
<213> ORGANISM: Mycobacterium tuberculosis

<400> SEQUENCE: 31

Asn Ile Arg Gln Ala Gly Val Gln Tyr
1               5

<210> SEQ ID NO 32
<211> LENGTH: 9
<212> TYPE: PRT
<213> ORGANISM: Mycobacterium tuberculosis

<400> SEQUENCE: 32

Glu Met Lys Thr Asp Ala Ala Thr Leu
1               5

<210> SEQ ID NO 33
<211> LENGTH: 10
<212> TYPE: PRT
<213> ORGANISM: Mycobacterium tuberculosis

<400> SEQUENCE: 33

Ala Glu Met Lys Thr Asp Ala Ala Thr Leu
1               5                   10

<210> SEQ ID NO 34
<211> LENGTH: 9
<212> TYPE: PRT
<213> ORGANISM: Mycobacterium tuberculosis

<400> SEQUENCE: 34

Leu Leu Asp Ala His Ile Pro Gln Leu
1               5

<210> SEQ ID NO 35
<211> LENGTH: 9
<212> TYPE: PRT
<213> ORGANISM: Mycobacterium tuberculosis

<400> SEQUENCE: 35

Ala Ala His Ala Arg Phe Val Ala Ala
1               5

<210> SEQ ID NO 36
<211> LENGTH: 11
<212> TYPE: PRT
<213> ORGANISM: Mycobacterium tuberculosis

<400> SEQUENCE: 36

Ala Val Ile Asn Thr Thr Cys Asn Tyr Gly Gln
1               5                   10

<210> SEQ ID NO 37
<211> LENGTH: 9
<212> TYPE: PRT
<213> ORGANISM: Mycobacterium tuberculosis

<400> SEQUENCE: 37

Ala Ser Pro Val Ala Gln Ser Tyr Leu
1               5

<210> SEQ ID NO 38
<211> LENGTH: 10
<212> TYPE: PRT
<213> ORGANISM: Mycobacterium tuberculosis
```

```
<400> SEQUENCE: 38

Glu Leu Pro Gln Trp Leu Ser Ala Asn Arg
1               5                   10
```